US008822642B2

(12) United States Patent
Levin et al.

(10) Patent No.: US 8,822,642 B2
(45) Date of Patent: Sep. 2, 2014

(54) DIMERIC FUSION PROTEINS AND RELATED COMPOSITIONS AND METHODS

(75) Inventors: Steven D. Levin, Seattle, WA (US); Margaret D. Moore, Seattle, WA (US); Craig D. Ostrander, Bothell, WA (US); Katherine E. Lewis, Seattle, WA (US); David W. Taft, Kirkland, WA (US); Robert J. Rosler, Lynnwood, WA (US); Anitra Wolf, Puyallup, WA (US); Megan M. Lantry, Redmond, WA (US)

(73) Assignee: ZymoGenetics, Inc., Princeton, NJ (US)

( * ) Notice: Subject to any disclaimer, the term of this patent is extended or adjusted under 35 U.S.C. 154(b) by 0 days.

(21) Appl. No.: 13/701,234

(22) PCT Filed: Jun. 7, 2011

(86) PCT No.: PCT/US2011/039422

§ 371 (c)(1), (2), (4) Date: Nov. 30, 2012

(87) PCT Pub. No.: WO2011/156356

PCT Pub. Date: Dec. 15, 2011

(65) Prior Publication Data

US 2013/0095102 A1 Apr. 18, 2013

Related U.S. Application Data

(60) Provisional application No. 61/352,873, filed on Jun. 9, 2010.

(51) Int. Cl.

| | |
|---|---|
| ***C07K 14/00*** | (2006.01) |
| ***C12N 5/10*** | (2006.01) |
| ***C07H 21/04*** | (2006.01) |
| ***A61K 38/16*** | (2006.01) |

(52) U.S. Cl.

USPC ......... 530/350; 536/23.4; 435/69.1; 514/21.2

(58) Field of Classification Search

None

See application file for complete search history.

(56) References Cited

U.S. PATENT DOCUMENTS

| | | | |
|---|---|---|---|
| 4,486,533 | A | 12/1984 | Lambowitz |
| 4,579,821 | A | 4/1986 | Palmiter et al. |
| 4,599,311 | A | 7/1986 | Kawasaki |
| 4,601,978 | A | 7/1986 | Karin |
| 4,615,974 | A | 10/1986 | Kingsman et al. |
| 4,656,134 | A | 4/1987 | Ringold |
| 4,661,454 | A | 4/1987 | Botstein et al. |
| 4,683,202 | A | 7/1987 | Mullis |
| 4,713,339 | A | 12/1987 | Levinson et al. |
| 4,784,950 | A | 11/1988 | Hagen et al. |
| 4,845,075 | A | 7/1989 | Murray et al. |
| 4,870,008 | A | 9/1989 | Brake |
| 4,882,279 | A | 11/1989 | Cregg |
| 4,931,373 | A | 6/1990 | Kawasaki et al. |
| 4,935,349 | A | 6/1990 | McKnight et al. |
| 4,956,288 | A | 9/1990 | Barsoum |
| 4,977,092 | A | 12/1990 | Bitter |
| 4,990,446 | A | 2/1991 | Oberto et al. |
| 5,037,743 | A | 8/1991 | Welch et al. |
| 5,063,154 | A | 11/1991 | Fink et al. |
| 5,139,936 | A | 8/1992 | Botstein et al. |
| 5,143,830 | A | 9/1992 | Holland et al. |
| 5,155,027 | A | 10/1992 | Sledziewski et al. |
| 5,162,222 | A | 11/1992 | Guarino et al. |
| 5,162,228 | A | 11/1992 | Sumino et al. |
| 5,208,036 | A | 5/1993 | Eppstein et al. |
| 5,223,409 | A | 6/1993 | Ladner et al. |
| 5,264,618 | A | 11/1993 | Felgner et al. |
| 5,279,833 | A | 1/1994 | Rose |
| 5,283,185 | A | 2/1994 | Epand et al. |
| 5,300,435 | A | 4/1994 | Granados |
| 5,399,346 | A | 3/1995 | Anderson et al. |
| 5,567,584 | A | 10/1996 | Sledziewski et al. |
| 5,605,690 | A | 2/1997 | Jacobs et al. |
| 5,641,655 | A | 6/1997 | Foster et al. |
| 5,716,808 | A | 2/1998 | Raymond |
| 5,736,383 | A | 4/1998 | Raymond |
| 5,854,039 | A | 12/1998 | Raymond et al. |
| 5,856,456 | A | 1/1999 | Whitlow et al. |
| 5,888,768 | A | 3/1999 | Raymond |
| 5,914,111 | A | 6/1999 | Wallner et al. |
| 2003/0103986 | A1 | 6/2003 | Rixon et al. |
| 2003/0232414 | A1 | 12/2003 | Moore |
| 2007/0054360 | A1* | 3/2007 | Gao et al. ..................... 435/69.1 |

FOREIGN PATENT DOCUMENTS

| | | |
|---|---|---|
| WO | WO92/06204 | 4/1992 |
| WO | WO94/06463 | 3/1994 |
| WO | WO94/12629 | 6/1994 |
| WO | WO95/05853 | 3/1995 |

(Continued)

OTHER PUBLICATIONS

Arai, K. et al., "Cytokines: Coordinators of Immune and Inflammatory Responses", Annual Rev. Biochemistry, vol. 59, pp. 783-836 (1990).

Ashkenazi, A. et al., "Immunoadhesins as research tools and therapeutic agents", Current Opinion in Immunology, vol. 9, pp. 195-200 (1997).

Edelman, G. et al., "The Covalent Structure of an Entire γG Immunoglobulin Molecule", PNAS, vol. 63, pp. 78-85 (1969).

(Continued)

*Primary Examiner* — Ilia Ouspenski

(74) *Attorney, Agent, or Firm* — Nickki L. Parlet

(57) ABSTRACT

Compositions and methods relating to soluble dimeric proteins are disclosed. The dimeric proteins comprise first and second polypeptide fusions linked via a dimerizing domain, each polypeptide fusion comprising first and second monomer domains corresponding to a cytokine or an extracellular domain of a cell-surface receptor. The monomer domains may be positioned amino terminal and carboxyl terminal to the dimerizing domain. Alternatively, the monomer domains may be positioned in tandem, either carboxyl terminal or amino terminal to the dimerizing domain. The dimeric proteins are useful in methods for therapy, diagnosis, and research.

15 Claims, 10 Drawing Sheets

(56) References Cited

FOREIGN PATENT DOCUMENTS

| | | |
|---|---|---|
| WO | WO97/20078 | 6/1997 |
| WO | WO2006/124667 | 11/2006 |
| WO | WO2007/124283 | 11/2007 |
| WO | WO2009/046407 | 4/2009 |

OTHER PUBLICATIONS

Hafler, J. et al., "CD226 Gly307Ser associatioin with multiple autoimmune diseases", Genes Immun., vol. 10(1), pp. 5-10 (2009).
Iguchi-Manaka, A. et al., "Accelerated tumor growth in mice deficient in DNAM-1 receptor", J. Exp. Medicine, vol. 205(13), pp. 2959-2964 (2008).
Gilfillan, S. et al., "DNAM-1 promotes activation of cytotoxic lymphocytes by nonprofessional antigen-presenting cells and tumors", J. Exp. Medicine, vol. 205(13), pp. 2965-2973 (2008).
Mosmann, Tim R., "Cytokines: is there biological meaning?", Current Opinion in Immunology, vol. 3, pp. 311-314 (1991).
Paul, W. et al., "Lymphocyte Responses and Cytokines" Cell, vol. 76, pp. 241-251 (1994).
Stemmer, Willem P., "DNA shuffling by random fragmentation and reassembly: In vitro recombination for molecular evolution", PNAS, vol. 91, pp. 10747-10751 (1994).
Yu, X. et al., "The surface protein TIGIT suppresses T cell activation by promoting the generation of mature immunoregulatory dendritic cells", Nature Immunology, vol. 10(1), pp. 48-57 (2009).

* cited by examiner

```
                                    Ala Ser Thr Lys Gly Pro Ser Val
                                   |CH1 ->

                                                                140
Phe Pro Leu Ala Pro Ser Ser Lys Ser Thr Ser Gly Gly Thr Ala

                                                                155
Ala Leu Gly Cys Leu Val Lys Asp Tyr Phe Pro Glu Pro Val Thr

                                                                170
Val Ser Trp Asn Ser Gly Ala Leu Thr Ser Gly Val His Thr Phe

                                                                185
Pro Ala Val Leu Gln Ser Ser Gly Leu Tyr Ser Leu Ser Ser Val

                                                                200
Val Thr Val Pro Ser Ser Ser Leu Gly Thr Gln Thr Tyr Ile Cys

                                                                215
Asn Val Asn His Lys Pro Ser Asn Thr Lys Val Asp Lys Lys Val
                                                            <- CH1|

                LC                      HC          HC
                |                       |           |
216             |                       |           |   230
|Glu Pro Lys Ser Cys Asp Lys Thr His Thr Cys Pro Pro Cys Pro|
|                        <- hinge ->                        |

                                                                245
|Ala Pro Glu Leu Leu Gly Gly Pro Ser Val Phe Leu Phe Pro Pro
|CH2 ->

                                                                260
Lys Pro Lys Asp Thr Leu Met Ile Ser Arg Thr Pro Glu Val Thr

                                                                275
Cys Val Val Val Asp Val Ser His Glu Asp Pro Glu Val Lys Phe

                                                                290
Asn Trp Tyr Val Asp Gly Val Glu Val His Asn Ala Lys Thr Lys

                                                                305
Pro Arg Glu Glu Gln Tyr Asn Ser Thr Tyr Arg Val Val Ser Val
```

Figure 1A

```
                                                          320
Leu Thr Val Leu His Gln Asp Trp Leu Asn Gly Lys Glu Tyr Lys

                                                          335
Cys Lys Val Ser Asn Lys Ala Leu Pro Ala Pro Ile Glu Lys Thr

                                                          350
Ile Ser Lys Ala Lys|Gly Gln Pro Arg Glu Pro Gln Val Tyr Thr
            <- CH2|CH3 ->

                                                          365
Leu Pro Pro Ser Arg Asp Glu Leu Thr Lys Asn Gln Val Ser Leu

                                                          380
Thr Cys Leu Val Lys Gly Phe Tyr Pro Ser Asp Ile Ala Val Glu

                                                          395
Trp Glu Ser Asn Gly Gln Pro Glu Asn Asn Tyr Lys Thr Thr Pro

                                                          410
Pro Val Leu Asp Ser Asp Gly Ser Phe Phe Leu Tyr Ser Lys Leu

                                                          425
Thr Val Asp Lys Ser Arg Trp Gln Gln Gly Asn Val Phe Ser Cys

                                                          440
Ser Val Met His Glu Ala Leu His Asn His Tyr Thr Gln Lys Ser

Leu Ser Leu Ser Pro Gly Lys  (SEQ ID NO:27)
```

Figure 1B

| | | | | | | | | | | | | | | | |
|---|---|---|---|---|---|---|---|---|---|---|---|---|---|---|---|
| | | | | | LC | | | | | | HC | | | HC | |
| | | | 218 | | | | 222 | | | | | | | | 230 |
| wt | Glu | Pro | Lys | Ser | Cys | Asp | Lys | Thr | His | Thr | Cys | Pro | Pro | Cys | Pro |
| Fc-488 | . | . | Arg | . | Ser | . | . | . | . | . | . | . | . | . | . |
| Fc4 | . | . | Arg | . | Ser | . | . | . | . | . | . | . | . | . | . |
| Fc5 | . | . | . | . | Ser | . | . | . | . | . | . | . | . | . | . |
| Fc6 | . | . | . | . | Ser | . | . | . | . | . | . | . | . | . | . |
| Fc7 | . | . | . | . | . | . | . | . | . | . | . | . | . | . | . |
| | | | | | | | <- hinge -> | | | | | | | | |

| | | | | | | | | | | | | | | | |
|---|---|---|---|---|---|---|---|---|---|---|---|---|---|---|---|
| | | | | 234 | 235 | | 237 | | | | | | | | 245 |
| wt | Ala | Pro | Glu | Leu | Leu | Gly | Gly | Pro | Ser | Val | Phe | Leu | Phe | Pro | Pro |
| Fc-488 | . | . | . | . | . | . | . | . | . | . | . | . | . | . | . |
| Fc4 | . | . | . | Ala | Glu | . | Ala | . | . | . | . | . | . | . | . |
| Fc5 | . | . | . | Ala | Glu | . | Ala | . | . | . | . | . | . | . | . |
| Fc6 | . | . | . | Ala | Glu | . | Ala | . | . | . | . | . | . | . | . |
| Fc7 | . | . | . | . | . | . | . | . | . | . | . | . | . | . | . |
| | CH2 -> | | | | | | | | | | | | | | |

| | | | | | | | | | | | | | | | |
|---|---|---|---|---|---|---|---|---|---|---|---|---|---|---|---|
| | | | | | | | | | | | | | | | 260 |
| wt | Lys | Pro | Lys | Asp | Thr | Leu | Met | Ile | Ser | Arg | Thr | Pro | Glu | Val | Thr |
| Fc-488 | . | . | . | . | . | . | . | . | . | . | . | . | . | . | . |
| Fc4 | . | . | . | . | . | . | . | . | . | . | . | . | . | . | . |
| Fc5 | . | . | . | . | . | . | . | . | . | . | . | . | . | . | . |
| Fc6 | . | . | . | . | . | . | . | . | . | . | . | . | . | . | . |
| Fc7 | . | . | . | . | . | . | . | . | . | . | . | . | . | . | . |

| | | | | | | | | | | | | | | | |
|---|---|---|---|---|---|---|---|---|---|---|---|---|---|---|---|
| | | | | | | | | | | | | | | | 275 |
| wt | Cys | Val | Val | Val | Asp | Val | Ser | His | Glu | Asp | Pro | Glu | Val | Lys | Phe |
| Fc-488 | . | . | . | . | . | . | . | . | . | . | . | . | . | . | . |
| Fc4 | . | . | . | . | . | . | . | . | . | . | . | . | . | . | . |
| Fc5 | . | . | . | . | . | . | . | . | . | . | . | . | . | . | . |
| Fc6 | . | . | . | . | . | . | . | . | . | . | . | . | . | . | . |
| Fc7 | . | . | . | . | . | . | . | . | . | . | . | . | . | . | . |

| | | | | | | | | | | | | | | | |
|---|---|---|---|---|---|---|---|---|---|---|---|---|---|---|---|
| | | | | | | | | | | | | | | | 290 |
| wt | Asn | Trp | Tyr | Val | Asp | Gly | Val | Glu | Val | His | Asn | Ala | Lys | Thr | Lys |
| Fc-488 | . | . | . | . | . | . | . | . | . | . | . | . | . | . | . |
| Fc4 | . | . | . | . | . | . | . | . | . | . | . | . | . | . | . |
| Fc5 | . | . | . | . | . | . | . | . | . | . | . | . | . | . | . |
| Fc6 | . | . | . | . | . | . | . | . | . | . | . | . | . | . | . |
| Fc7 | . | . | . | . | . | . | . | . | . | . | . | . | . | . | . |

| | | | | | | | | | | | | | | | |
|---|---|---|---|---|---|---|---|---|---|---|---|---|---|---|---|
| | | | | | | | 297 | | | | | | | | 305 |
| wt | Pro | Arg | Glu | Glu | Gln | Tyr | Asn | Ser | Thr | Tyr | Arg | Val | Val | Ser | Val |
| Fc-488 | . | . | . | . | . | . | . | . | . | . | . | . | . | . | . |
| Fc4 | . | . | . | . | . | . | . | . | . | . | . | . | . | . | . |
| Fc5 | . | . | . | . | . | . | . | . | . | . | . | . | . | . | . |
| Fc6 | . | . | . | . | . | . | . | . | . | . | . | . | . | . | . |
| Fc7 | . | . | . | . | . | . | Gln | . | . | . | . | . | . | . | . |

Figure 2A

| | | | | | | | | | | | | | | | 320 |
|---|---|---|---|---|---|---|---|---|---|---|---|---|---|---|---|
| wt | Leu | Thr | Val | Leu | His | Gln | Asp | Trp | Leu | Asn | Gly | Lys | Glu | Tyr | Lys |
| Fc-488 | . | . | . | . | . | . | . | . | . | . | . | . | . | . | . |
| Fc4 | . | . | . | . | . | . | . | . | . | . | . | . | . | . | . |
| Fc5 | . | . | . | . | . | . | . | . | . | . | . | . | . | . | . |
| Fc6 | . | . | . | . | . | . | . | . | . | . | . | . | . | . | . |
| Fc7 | . | . | . | . | . | . | . | . | . | . | . | . | . | . | . |

| | | | | | | | | | | 330 | 331 | | | | 335 |
|---|---|---|---|---|---|---|---|---|---|---|---|---|---|---|---|
| wt | Cys | Lys | Val | Ser | Asn | Lys | Ala | Leu | Pro | Ala | Pro | Ile | Glu | Lys | Thr |
| Fc-488 | . | . | . | . | . | . | . | . | . | . | . | . | . | . | . |
| Fc4 | . | . | . | . | . | . | . | . | . | Ser | Ser | . | . | . | . |
| Fc5 | . | . | . | . | . | . | . | . | . | Ser | Ser | . | . | . | . |
| Fc6 | . | . | . | . | . | . | . | . | . | Ser | Ser | . | . | . | . |
| Fc7 | . | . | . | . | . | . | . | . | . | . | . | . | . | . | . |

| | | | | | | | | | | | | | | | 350 |
|---|---|---|---|---|---|---|---|---|---|---|---|---|---|---|---|
| wt | Ile | Ser | Lys | Ala | Lys | \|Gly | Gln | Pro | Arg | Glu | Pro | Gln | Val | Tyr | Thr |
| Fc-488 | . | . | . | . | . | \| . | . | . | . | . | . | . | . | . | . |
| Fc4 | . | . | . | . | . | \| . | . | . | . | . | . | . | . | . | . |
| Fc5 | . | . | . | . | . | \| . | . | . | . | . | . | . | . | . | . |
| Fc6 | . | . | . | . | . | \| . | . | . | . | . | . | . | . | . | . |
| Fc7 | . | . | . | . | . | \| . | . | . | . | . | . | . | . | . | . |

<- CH2|CH3 ->

| | | | | | | 356 | | 358 | | | | | | | 365 |
|---|---|---|---|---|---|---|---|---|---|---|---|---|---|---|---|
| wt | Leu | Pro | Pro | Ser | Arg | Asp | Glu | Leu | Thr | Lys | Asn | Gln | Val | Ser | Leu |
| Fc-488 | . | . | . | . | . | . | . | . | . | . | . | . | . | . | . |
| Fc4 | . | . | . | . | . | . | . | . | . | . | . | . | . | . | . |
| Fc5 | . | . | . | . | . | . | . | . | . | . | . | . | . | . | . |
| Fc6 | . | . | . | . | . | . | . | . | . | . | . | . | . | . | . |
| Fc7 | . | . | . | . | . | . | . | . | . | . | . | . | . | . | . |

| | | | | | | | | | | | | | | | 380 |
|---|---|---|---|---|---|---|---|---|---|---|---|---|---|---|---|
| wt | Thr | Cys | Leu | Val | Lys | Gly | Phe | Tyr | Pro | Ser | Asp | Ile | Ala | Val | Glu |
| Fc-488 | . | . | . | . | . | . | . | . | . | . | . | . | . | . | . |
| Fc4 | . | . | . | . | . | . | . | . | . | . | . | . | . | . | . |
| Fc5 | . | . | . | . | . | . | . | . | . | . | . | . | . | . | . |
| Fc6 | . | . | . | . | . | . | . | . | . | . | . | . | . | . | . |
| Fc7 | . | . | . | . | . | . | . | . | . | . | . | . | . | . | . |

| | | | | | | | | | | | | | | | 395 |
|---|---|---|---|---|---|---|---|---|---|---|---|---|---|---|---|
| wt | Trp | Glu | Ser | Asn | Gly | Gln | Pro | Glu | Asn | Asn | Tyr | Lys | Thr | Thr | Pro |
| Fc-488 | . | . | . | . | . | . | . | . | . | . | . | . | . | . | . |
| Fc4 | . | . | . | . | . | . | . | . | . | . | . | . | . | . | . |
| Fc5 | . | . | . | . | . | . | . | . | . | . | . | . | . | . | . |
| Fc6 | . | . | . | . | . | . | . | . | . | . | . | . | . | . | . |
| Fc7 | . | . | . | . | . | . | . | . | . | . | . | . | . | . | . |

Figure 2B

| | | | | | | | | | | | | | | | |
|---|---|---|---|---|---|---|---|---|---|---|---|---|---|---|---|
| | | | | | | | | | | | | | | | **410** |
| wt | Pro | Val | Leu | Asp | Ser | Asp | Gly | Ser | Phe | Phe | Leu | Tyr | Ser | Lys | Leu |
| Fc-488 | . | . | . | . | . | . | . | . | . | . | . | . | . | . | . |
| Fc4 | . | . | . | . | . | . | . | . | . | . | . | . | . | . | . |
| Fc5 | . | . | . | . | . | . | . | . | . | . | . | . | . | . | . |
| Fc6 | . | . | . | . | . | . | . | . | . | . | . | . | . | . | . |
| Fc7 | . | . | . | . | . | . | . | . | . | . | . | . | . | . | . |

| | | | | | | | | | | | | | | | |
|---|---|---|---|---|---|---|---|---|---|---|---|---|---|---|---|
| | | | | | | | | | | | | | | | **425** |
| wt | Thr | Val | Asp | Lys | Ser | Arg | Trp | Gln | Gln | Gly | Asn | Val | Phe | Ser | Cys |
| Fc-488 | . | . | . | . | . | . | . | . | . | . | . | . | . | . | . |
| Fc4 | . | . | . | . | . | . | . | . | . | . | . | . | . | . | . |
| Fc5 | . | . | . | . | . | . | . | . | . | . | . | . | . | . | . |
| Fc6 | . | . | . | . | . | . | . | . | . | . | . | . | . | . | . |
| Fc7 | . | . | . | . | . | . | . | . | . | . | . | . | . | . | . |

| | | | | | | | | | | | | | | | |
|---|---|---|---|---|---|---|---|---|---|---|---|---|---|---|---|
| | | | | | | **431** | | | | | | | | | **440** |
| wt | Ser | Val | Met | His | Glu | Ala | Leu | His | Asn | His | Tyr | Thr | Gln | Lys | Ser |
| Fc-488 | . | . | . | . | . | . | . | . | . | . | . | . | . | . | . |
| Fc4 | . | . | . | . | . | . | . | . | . | . | . | . | . | . | . |
| Fc5 | . | . | . | . | . | . | . | . | . | . | . | . | . | . | . |
| Fc6 | . | . | . | . | . | . | . | . | . | . | . | . | . | . | . |
| Fc7 | . | . | . | . | . | . | . | . | . | . | . | . | . | . | . |

| | | | | | | | | | |
|---|---|---|---|---|---|---|---|---|---|
| | | | | | | **446** | | | |
| wt | Leu | Ser | Leu | Ser | Pro | Gly | Lys | *** | (SEQ ID NO:28) |
| Fc-488 | . | . | . | . | . | . | . | . | (SEQ ID NO:29) |
| Fc4 | . | . | . | . | . | . | . | . | (SEQ ID NO:30) |
| Fc5 | . | . | . | . | . | . | . | . | (SEQ ID NO:31) |
| Fc6 | . | . | . | . | . | . | *** | | (SEQ ID NO:32) |
| Fc7 | . | . | . | . | . | . | . | . | (SEQ ID NO:33) |

Figure 2C

** $p < 0.05$ vs PBS via repeated-measures ANOVA

Mean +/- SEM

DIMERIC FUSION PROTEINS AND RELATED COMPOSITIONS AND METHODS

CROSS-REFERENCE TO RELATED APPLICATIONS

This application claims the benefit of U.S. Provisional Application Ser. No. 61/352,873 filed Jun. 9, 2010.

BACKGROUND OF THE INVENTION

Cell-surface receptors mediate a variety of biological effects through binding their cognate ligands. Receptors are typically composed of one or more integral membrane proteins that bind the ligand, such as a cytokine or counter-receptor, with high affinity and transduce this binding event to the cell through the cytoplasmic portions of the certain receptor subunits. Cell-surface receptors have been grouped into several classes on the basis of similarities in their extracellular ligand binding domains.

The physiological importance of cell-surface receptors is exemplified by the role of co-stimulatory receptors in mediating immune cell function. T cells are normally activated by T cell antigen receptor (TCR) engagement by MHC molecules plus foreign peptides presented by antigen presenting cells (APCs). Professional APCs also express a number of co-stimulatory molecules that engage other receptors on the T cells and contribute to activation. A proven means of inhibiting T cell activation is interference with engagement of these co-stimulatory molecules. Most notably, CTLA4-Ig can be used to prevent the critical co-stimulatory signals through the CD28 molecule, thereby interfering with T cell responses.

Other co-stimulatory molecules have been identified and these tend to be important in specialized situations where their counter-structures are expressed. One such molecule whose contribution has only recently been appreciated is the co-stimulatory receptor CD226. The counter-structures for CD226 are the nectin-family proteins PVR (CD155) and Nectin-2 (CD112), which are widely expressed in tissues typically infiltrated by lymphocytes in auto-immune or auto-inflammatory diseases including epithelium, endothelium, synoviocytes, and cells of the CNS. Importantly, signals through CD226 have been shown to be critical to T cell activation in situations where T cells are being stimulated by non-professional APC's (see Gilfillan et al., *J. Exp. Med.* 205:2965-2973, 2008; Iguchi-Manaka et al., *J. Exp. Med.* 205:2959-2964, 2008), which would include autoimmune diseases where T cells are being activated and causing damage in inflamed tissues. Moreover, a polymorphism in CD226 has recently been linked to risk of developing a number of autoimmune conditions including multiple sclerosis (MS), type I diabetes, Grave's disease, and Wegener's granulomatosis. (See International Multiple Sclerosis Genetics Consortium (IMSGC), *Genes Immun.* 10:11-14, 2009; Hafler et al., *Genes Immun.* 10:5-10, 2009; Maier and Hafler, *Immunol. Rev.* 229:322-336, 2009; Mait et al., "Non-synonymous variant (Gly307Ser) in CD226 is associated with susceptibility to multiple autoimmune diseases," *Rheumatology* (Oxford) (Mar. 24, 2010 [Epub ahead of print]).) Hence, there is sound rationale for interfering with CD226-mediated signals in immune cell function.

VSTM3 (also referred to as B7R1 in International PCT Publication No. WO 06/124667) is an inhibitory member of the CD28 family that has been shown to also bind to PVR and Nectin-2, the same counter-structures as CD226. In fact, VSTM3 and CD226 cross-compete for binding to PVR and Nectin-2, indicating that they bind overlapping if not identical regions, although VSTM3 seems to bind with somewhat higher affinity.

Soluble forms of many cell-surface receptors are known. These soluble receptors correspond to the ligand-binding domains of their cell-surface counterparts. For example, naturally occurring soluble cytokine receptors inhibit cytokine responses and act as transport proteins. (See, e.g., Aggarwal and Puri, "Common and Uncommon Features of Cytokines and Cytokine Receptors: An Overview," in Aggarwal and Puri, eds., *Human Cytokines: Their Role in Disease and Therapy*, Blackwell Science, 1995, 3-24.) In addition, it has been found that dimerization of soluble receptor polypeptides through the use of fusion proteins may enhance the binding properties of these soluble receptors so that they become therapeutically useful antagonists of their cognate ligands. Typical of such dimeric fusions are immunoglobulin fusions. (See, e.g., Sledziewski et al., U.S. Pat. Nos. 5,155,027 and 5,567,584; Jacobs et al., U.S. Pat. No. 5,605,690; Wallner et al., U.S. Pat. No. 5,914,111; and Ashkenazi and Chamow, *Curr. Opin. Immunol.* 9:195-200, 1997.)

For example, soluble VSTM3 has been shown to be therapeutically efficacious in animal models of T-cell-mediated disease. In particular, it has been shown that soluble VSTM3-Fc dimers, in a conventional bivalent format, inhibit T cell responses in vivo, as measured by a Delayed Type Hypersensitivity (DTH) reaction, and that such dimers decrease disease incidence and progression in a Collagen Induced Arthritis (CIA) model. (See International PCT Publication No. WO 06/124667.) A soluble VSTM3-VASP tetramer has also been shown to be efficacious in the CIA model. (See id.)

A variety of biological effects, including the growth and differentiation of many cell types, are also mediated by small, soluble proteins collectively referred to as cytokines (see, e.g., Arai et al., *Annu. Rev. Biochem.* 59:783, 1990; Mosmann, *Curr. Opin. Immunol.* 3:311, 1991; Paul and Seder, *Cell* 76:241, 1994). Proteins that constitute the cytokine group include interleukins, interferons, colony stimulating factors, tumor necrosis factors, and other regulatory molecules.

The demonstrated in vivo activities of cell-surface receptors and cytokines illustrate the clinical potential of, and need for, molecules that mediate the biological activities of receptors and cytokines. For example, demonstrated in vivo activities of pro-inflammatory receptors and cytokines, including the activities of co-stimulatory receptors in mediating immune cell responses, illustrate the enormous clinical potential of, and need for, antagonists of pro-inflammatory molecules. There is particularly a need for soluble fusions of such cell-surface receptors and cytokines having improved activity relative to known fusion protein formats. The present invention, as set forth herein, meets these and other needs.

BRIEF SUMMARY OF THE INVENTION

In one aspect, the present invention provides a soluble polypeptide fusion comprising, from amino terminus to carboxyl terminus, P1-L1-D-L2-P2 or P2-L2-P1-L1-D, where P1 is (i) an extracellular domain of a first cell-surface receptor or a functional variant or fragment thereof, or (ii) a first cytokine or a functional variant or fragment thereof; L1 is a first polypeptide linker; D is a dimerizing domain; L2 is a second polypeptide linker; and P2 is (i) an extracellular domain of a second cell-surface receptor or a functional variant or fragment thereof, or (ii) a second cytokine or a functional variant or fragment thereof. In a related aspect, the present invention provides a dimeric protein comprising a first soluble polypeptide fusion and a second soluble polypeptide fusion, where each of the first and second soluble polypeptide fusions comprises the formula P1-L1-D1-L2-P2 or P2-L2-P1-L1-D above.

In certain embodiments of a soluble polypeptide fusion or dimeric protein as above, where P1 is the extracellular domain of the first cell-surface receptor or functional variant or fragment thereof and/or P2 is the extracellular domain of the second cell-surface receptor or functional variant or fragment thereof, the first cell-surface receptor and/or the second cell-surface receptor are individually selected from the group consisting of 4-1BB; ACTH Receptor; Activin Receptors; BLTR (the Leukotriene B4 Receptor); BMP Receptor; C3a Receptor; C5a Receptor; CCR1; CCR2; CCR3; CCR4; CCR5; CCR6; CCR7; CCR8; CCR9; CD19; CD22; CD27; CD28; CD30; CD40; CD70; CD80; CD86; CTLA-4; CD226; VSTM3 (B7R1); CD112; CD155; B7H6; NKp30; ICAM; VLA-4; VCAM; CT-1 Receptor; CX3CR1; CXCR1; CXCR2; CXCR3; CXCR4; CXCR5; D6; DARC; DcR3; DR4; DR5; DcR1; DcR2; ECRF3; Fas; fMLP Receptors; G-CSF Receptor; GIT Receptor; GM-CSF Receptor; Growth Hormone Receptor; HVEM; BTLA; Interferon-α Receptor; Interferon-β Receptor; Interferon-γ Receptor; IL-1 Receptor Type I; IL-1 Receptor Type II; IL-10 Receptor; IL-11 Receptor; IL-12 Receptor; IL-13 Receptor; IL-15 Receptor; IL-16 Receptor (CD4); IL-17 Receptor A; IL-17 Receptor B; IL-17 Receptor C; IL-17 Receptor D; IL-17 Receptor E; IL-18 Receptor; IL-2 Receptor; IL-3 Receptor; IL-4 Receptor; IL-5 Receptor; IL-6 Receptor; IL-7 Receptor; IL-9 Receptor; IL-20 Receptor A; IL-20 Receptor B; IL-21 Receptor; IL-22 Receptor A; IL-22 Receptor B; IL-28 Receptor A; IL-27 Receptor A; IL-31-Receptor A; BCMA; TACI; BAFF receptor; Immunoregulatory Semaphorin Receptor CD72; Kaposi's Sarcoma-associated Herpesvirus GPCR; Lipoxin A4 Receptor; Lymphotoxin β Receptor; Lysophospholipid Growth Factor Receptors; Neurokinin 1; Opioid μ, δ, and κ Receptors for Endorphins; Oncostatin M Receptor; Osteopontin Receptor; Osteoprotegerin; Ox40; PACAP and VIP Receptors; PAF Receptors; Poxvirus; IFNα/β Receptor Homologs; Poxvirus IFNγ Receptor Homologs; Poxvirus IL-1β Receptor Homologs; Poxvirus Membrane-bound G Protein-coupled Receptor Homologs; Poxvirus Secreted Chemokine-binding Proteins; Poxvirus TNF Receptor Homologs; Prolactin Receptor; RANK; RON Receptor; SCF Receptor; Somatostatin Receptors; T1/ST2; TGF-beta Receptors; TNF Receptors (e.g., p60 and p80); TNFRSF19; TPO Receptor; US28; XCR1; Erythropoietin receptor; growth hormone receptor; Leukemia inhibitory factor receptor; and C-kit receptor. Where both P1 and P2 are an extracellular domain of a cell-surface receptor or functional variant or fragment thereof, the first and second cell-surface receptors can be the same or different.

In other embodiments, where P1 is the first cytokine or functional variant or fragment thereof and/or P2 is the second cytokine or functional variant or fragment thereof, the first cytokine and/or the second cytokine are individually selected from the group consisting of α-MSH; 9E3/cCAF; ACTH; Activin; AK155; Angiostatin; Apo2L/TRAIL; APRIL; BAFF (BLys); BLR1Ligand/BCA-1/BLC/CXCL13; BMP Family; BRAK; Calcitonin Gene-related Peptide (CGRP); CC Chemokine of Molluscum Contagiosum Virus; CCL27; CCL28; CD100/Sema4D; CD27 Ligand; CD30 Ligand; CD40 Ligand; CK138-1/MPIF-1/CCL23; CLF/CLC; CSF-1; CT-1; CTAP-III, βTG, and NAP-2//CXCL7; CXCL16; Defensins; ELC/MIP-3β/Exodus-3/CCL19; ENA-78/CXCL5; Endorphins; Endostatin; Eotaxin 2/MPIF-2/CCL24; Eotaxin/CCL11; Erythropoietin; Exodus-1/LARC/MIP-3α (SCYA 20); Fas Ligand; Flt-3 Ligand; fMLP; Fractalkine/CX3CL1; G-CSF; GCP-2/CXCL6; GM-CSF; Growth Hormone; HCC-1/CCL14; HCC-4/CCL16; High Mobility Group Box 1 (HMGB1); Human Cathelicidin Antimicrobial Peptide LL-37; I-309/CCL1; IFNα, IFNβ, and IFNω Ligands; IFNγ; IL-1α; IL-1β; IL-10; IL-11; IL-12; IL-13; IL-15; IL-16; IL-17A; IL-17B; IL-17C; IL-17D; IL-17E; IL-17F; IL-18; IL-1Ra; IL-2; IL-27; IL-3; IL-4; IL-5; IL-6; IL-7; IL-8/CXCL8; IL-9; IP-10/CXCL10; IL-19; IL-20; IL-21; IL-22; IL-23; IL-24; IL-26; IL-31; Keratinocyte Growth Factor; KSHV-related IL-6 Ligand; Leptin; Leukotactin 1/HCC-2/MIP-1δ/CCL15; Leukotriene B4; LIGHT; Lipoxin; Lymphotactin/XCL1; Lymphotoxin α and β; Lysophospholipid Growth Factors; Macrophage-derived Chemokine; Macrophage-Stimulating Protein (MSP); MCP-1/CCL2, MCP-2/CCL8, MCP-3/CCL7, MCP-4/CCL13, and MCP-5/CCL12; Methoxyestradiol; MGSA/GRO/CXCL1, CXCL2, CXCL3; MIF; MIG/CXCL9; MIP-1α/CCL3, MIP-1β/CCL4; MIP-1γ/MRP-2/CCF18/CCL9/10; Mu C10/CCL6; Oncostatin M; Osteopontin; Parapoxvirus (Orf Virus) IL-10 Homolog; PARC/DC-CCK1/AMAC-1/CCL18; PDGF-A; PDGF-B; PDGF-C; PDGF-D; Platelet-Activating Factor; Platelet Factor 4/CXCL4; Poxvirus Growth Factors Related to Epidermal Growth Factor; Poxvirus Secreted Complement Control Proteins; Poxvirus Vascular Endothelial Growth Factor (VEGF) Homologs of Orf Virus; Prolactin; RANK Ligand; RANTES/CCL5; S100A12; SDF-1/CXCL12; SERP-1, a Secreted Poxyiral Serpin; SLC (6Ckine)/Exodus-2/TCA-4/CCL21; Somatostatin; Stem Cell Factor; Substance P; TARC/CCL17; TCA3/Mouse CCL1; TECK/CCL25; TGFβ; Thrombopoietin; TNFα; TSG-6; TWEAK; Vaccinia Virus Semaphorin; vCXC-1 and vCXC-2; VEGF; VIP and PACAP; and Viral IL-10 Variants. Where both P1 and P2 are a cytokine or functional variant or fragment thereof, the first and second cytokines can be the same or different.

In certain embodiments, each of P1 and P2 is an extracellular domain of VSTM3 (B7R1), or a functional variant or fragment thereof. For example, in particular variations of a soluble polypeptide fusion having the formula P1-L1-D-L2-P2 or P2-L2-P1-L1-D as above, P1 is a first polypeptide having at least 95% identity with amino acid residues 25-141 of SEQ ID NO:2, and P2 is a second polypeptide having at least 95% identity with amino acid residues 25-141 of SEQ ID NO:2; where the polypeptide fusion is capable of specifically binding to the extracellular domain of CD155 (amino acid residues 28-343 of SEQ ID NO:22). In some embodiments, at least one of P1 and P2 has 100% identity with amino acid residues 25-141 of SEQ ID NO:2. In other variations, at least one of P1 and P2 includes a non-cysteine residue, such as tyrosine, at the amino acid position corresponding to residue 69 of SEQ ID NO:2. For example, in specific embodiments, at least one of P1 and P2 has the amino acid sequence shown in residues 23-139 of SEQ ID NO:18.

Particularly suitable dimerizing domains for use in accordance with a polypeptide fusion or dimeric protein as above include immunoglobulin heavy chain constant regions. For example, in specific variations, the dimerizing domain D is an Fc fragment, such as a human γ1 Fc fragment.

In some embodiments of a polypeptide fusion or dimeric protein as above, the linker L1 consists of from 15 to 32 amino acid residues, where from 1 to 8 (e.g., two) of these residues are cysteine residues. In particular variations, L1 comprises an immunoglobulin hinge region or variant thereof. For example, in a specific embodiment, L1 comprises an immunoglobulin hinge variant (e.g., a human γ1 hinge variant) wherein the cysteine residue corresponding to Eu residue 220 is replaced by serine.

Particularly suitable L2 linkers for use in accordance with a polypeptide fusion or dimeric protein as above include linkers comprising a plurality of glycine residues and optionally comprising at least one serine residue. For example, in a specific embodiment of a polypeptide fusion comprising the formula P1-L1-D-L2-P2, or a dimeric protein comprising first and second such polypeptide fusions, L2 comprises the amino acid sequence shown in SEQ ID NO:25. In a specific embodiment of a polypeptide fusion comprising the formula P2-L2-P1-L1-D, or a dimeric protein protein comprising first and second such polypeptide fusions, L2 comprises the formula [Gly-Gly-Gly-Ser]n (SEQ ID NO:26), wherein n is an integer from 3 to 5, inclusive.

In specific variations of a polypeptide fusion comprising the formula P1-L1-D-L2-P2 or P2-L2-P1-L1-D and in which each of P1 and P2 is an extracellular domain of VSTM3 or a functional variant or fragment thereof, the polypeptide fusion comprises an amino acid sequence selected from (a) the amino acid sequence shown in residues 23-493 of SEQ ID NO:18 and (b) the amino acid sequence shown in residues 23-508 or 23-507 of SEQ ID NO:20. Similarly, in specific variations of a dimeric protein in accordance with the present invention, each of the first and second polypeptide fusions comprises an amino acid sequence selected from (a) the amino acid sequence shown in residues 23-493 of SEQ ID NO:18 and (b) the amino acid sequence shown in residues 23-508 or 23-507 of SEQ ID NO:20.

In another aspect, the present invention provides a polynucleotide encoding a polypeptide fusion as above. In a related aspect, the present invention provides a vector comprising such a polynucleotide. For example, in some embodiments, the present invention provides an expression vector comprising the following operably linked elements: a transcription promoter; a DNA segment encoding a polypeptide fusion as above; and a transcription terminator.

In yet other related aspects, the present invention provides cultured cells comprising such vectors, as well as methods for producing a polypeptide or dimeric protein as disclosed above. For example, in some embodiments, a cultured cell in accordance with the present invention comprises an expression vector comprising the following operably linked elements: a transcription promoter; a DNA segment encoding a polypeptide fusion as above; and a transcription terminator; and where the cell expresses the polypeptide fusion encoded by the DNA segment. In certain variations of a method of making the polypeptide fusion, the method includes (i) culturing a cell comprising an expression vector as disclosed above, where the cell expresses the polypeptide fusion encoded by the DNA segment and the encoded polypeptide fusion is produced; and (ii) recovering the soluble polypeptide fusion. Similarly, in certain variations of a method of making the dimeric protein, the method includes (i) culturing a cell comprising an expression vector as disclosed above, where the cell expresses the polypeptide fusion encoded by the DNA segment and the encoded polypeptide fusion is produced as a dimeric protein; and (ii) recovering the dimeric protein.

The present invention further includes a composition comprising a polypeptide fusion or dimeric protein as above and at least one pharmaceutically acceptable carrier.

In still another aspect, the present invention provides a method of treating a T-cell mediated immune disorder using a dimeric VSTM3 protein as disclosed above. The method generally includes administering to a subject having the T-cell mediated immune disorder an effective amount of the dimeric VSTM3 protein. T-cell mediated immune disorders amenable to treatment with a dimerc VSTM3 protein as disclosed herein include, for example, autoimmune diseases, graft-versus-host disease (GVHD), and transplant rejection. In specific variations, the method is a method for treating an autoimmune disease selected from rheumatoid arthritis, multiple sclerosis (MS) (e.g., spino-optical MS, primary progressive MS (PPMS), and relapsing remitting MS (RRMS)), insulin dependent diabetes mellitus (IDDM), systemic lupus erythematosus (SLE), coeliac disease, neuritis, polymyositis, psoriasis, psoriatic arthritis, vitiligo, Sjogren's syndrome, autoimmune pancreatitis, an inflammatory bowel disease (e.g., Crohn's disease, ulcerative colitis), active chronic hepatitis, glomerulonephritis, scleroderma, sarcoidosis, an autoimmune thyroid disease, Hashimoto's thyroiditis, Graves disease, Wegener's granulomatosis, myasthenia gravis, asthma, Addison's disease, autoimmune uveoretinitis, pemphigus vulgaris, primary biliary cirrhosis, pernicious anemia, sympathetic opthalmia, uveitis, autoimmune hemolytic anemia, pulmonary fibrosis, chronic beryllium disease, and idiopathic pulmonary fibrosis.

These and other aspects of the invention will become evident upon reference to the following detailed description of the invention and the attached drawings.

DEFINITIONS

Unless defined otherwise, all technical and scientific terms used herein have the same meaning as commonly understood by one of ordinary skill in the art pertinent to the methods and compositions described. As used herein, the following terms and phrases have the meanings ascribed to them unless specified otherwise.

The terms "a," "an," and "the" include plural referents, unless the context clearly indicates otherwise.

A "polypeptide" is a polymer of amino acid residues joined by peptide bonds, whether produced naturally or synthetically. Polypeptides of less than about 10 amino acid residues are commonly referred to as "peptides."

A "protein" is a macromolecule comprising one or more polypeptide chains. A protein may also comprise non-peptidic components, such as carbohydrate groups. Carbohydrates and other non-peptidic substituents may be added to a protein by the cell in which the protein is produced, and will vary with the type of cell. Proteins are defined herein in terms of their amino acid backbone structures; substituents such as carbohydrate groups are generally not specified, but may be present nonetheless.

The terms "amino-terminal" (or "N-terminal") and "carboxyl-terminal" (or "C-terminal") are used herein to denote positions within polypeptides. Where the context allows, these terms are used with reference to a particular sequence or portion of a polypeptide to denote proximity or relative position. For example, a certain sequence positioned carboxyl-terminal to a reference sequence within a polypeptide is located proximal to the carboxyl terminus of the reference sequence, but is not necessarily at the carboxyl terminus of the complete polypeptide.

The term "corresponding to," when applied to positions of amino acid residues in sequences, means corresponding positions in a plurality of sequences when the sequences are optimally aligned.

"Non-covalent associations" between polypeptides or proteins include hydrogen bonding, steric interactions, hydrophobic interactions, and ionic interactions.

The terms "polynucleotide" and "nucleic acid" are used synonymously herein and refer to a single- or double-stranded polymer of deoxyribonucleotide or ribonucleotide bases read from the 5' to the 3' end. Polynucleotides include RNA and DNA, and may be isolated from natural sources, synthesized in vitro, or prepared from a combination of natural and synthetic molecules. Sizes of polynucleotides are expressed as base pairs (abbreviated "bp"), nucleotides ("nt"), or kilobases ("kb"). Where the context allows, the latter two terms may describe polynucleotides that are single-stranded or double-stranded. When the term is applied to double-stranded molecules it is used to denote overall length and will be understood to be equivalent to the term "base pairs." It will be recognized by those skilled in the art that the two strands of a double-stranded polynucleotide may differ slightly in length and that the ends thereof may be staggered as a result of enzymatic cleavage; thus all nucleotides within a double-stranded polynucleotide molecule may not be paired. Such unpaired ends will in general not exceed 20 nt in length.

A "segment" is a portion of a larger molecule (e.g., polynucleotide or polypeptide) having specified attributes. For example, a DNA segment encoding a specified polypeptide is a portion of a longer DNA molecule, such as a plasmid or plasmid fragment that, when read from the 5' to the 3' direction, encodes the sequence of amino acids of the specified polypeptide. Also, in the context of a polypeptide fusion in accordance with the present invention, a polypeptide segment corresponding to a cytokine or an extracellular domain of a cell-surface receptor is a portion of the longer polypeptide fusion molecule that, in addition to the polypeptide segment corresponding to the cytokine or extracellular domain of the cell-surface receptor, includes other polypeptide segments (e.g., linkers, dimerizing domain) as described herein.

A "monomer" or "monomer domain" as used herein means a polypeptide segment corresponding to a cytokine or an extracellular domain of a cell-surface receptor.

The term "expression vector" is used to denote a DNA molecule, linear or circular, that comprises a segment encoding a polypeptide of interest operably linked to additional segments that provide for its transcription. Such additional segments include promoter and terminator sequences, and may also include one or more origins of replication, one or more selectable markers, an enhancer, a polyadenylation signal, etc. Expression vectors are generally derived from plasmid or viral DNA, or may contain elements of both.

The term "promoter" is used herein for its art-recognized meaning to denote a portion of a gene containing DNA sequences that provide for the binding of RNA polymerase and initiation of transcription. Promoter sequences are commonly, but not always, found in the 5' non-coding regions of genes.

A "secretory signal sequence" is a DNA sequence that encodes a polypeptide (a "secretory peptide") that, as a component of a larger polypeptide, directs the larger polypeptide through a secretory pathway of a cell in which it is synthesized. The larger polypeptide is commonly cleaved to remove the secretory peptide during transit through the secretory pathway.

"Operably linked" means that two or more entities are joined together such that they function in concert for their intended purposes. When referring to DNA segments, the phrase indicates, for example, that coding sequences are joined in the correct reading frame, and transcription initiates in the promoter and proceeds through the coding segment(s) to the terminator. When referring to polypeptides, "operably linked" includes both covalently (e.g., by disulfide bonding) and non-covalently (e.g., by hydrogen bonding, hydrophobic interactions, or salt-bridge interactions) linked sequences, wherein the desired function(s) of the sequences are retained.

An "isolated polypeptide" is a polypeptide that is essentially free from contaminating cellular components, such as carbohydrate, lipid, or other proteinaceous impurities associated with the polypeptide in nature. Typically, a preparation of isolated polypeptide contains the polypeptide in a highly purified form, i.e., at least about 80% pure, at least about 90% pure, at least about 95% pure, greater than 95% pure, such as 96%, 97%, or 98% or more pure, or greater than 99% pure. One way to show that a particular protein preparation contains an isolated polypeptide is by the appearance of a single band following sodium dodecyl sulfate (SDS)-polyacrylamide gel electrophoresis of the protein preparation and Coomassie Brilliant Blue staining of the gel. However, the term "isolated" does not exclude the presence of the same polypeptide in alternative physical forms, such as dimers or alternatively glycosylated or derivatized forms.

An "immunoglobulin" is a serum protein which functions as an antibody in a vertebrate organism. Five classes of "immunoglobulin," or antibody, protein (IgG, IgA, IgM, IgD, and IgE) have been identified in higher vertebrates. IgG comprises the major class; it normally exists as the second most abundant protein found in plasma. In humans, IgG consists of four subclasses, designated IgG1, IgG2, IgG3, and IgG4. The heavy chain constant regions of the IgG class are identified with the Greek symbol γ. For example, immunoglobulins of the IgG1 subclass contain a γ1 heavy chain constant region. Each immunoglobulin heavy chain possesses a constant region that consists of constant region protein domains (CH1, hinge, CH2, and CH3) that are essentially invariant for a given subclass in a species. DNA sequences encoding human and non-human immunoglobulin chains are known in the art. See, e.g., Ellison et al., DNA 1:11-18, 1981; Ellison et al., Nuc. Acids Res. 10:4071-4079, 1982; Kenten et al., Proc. Natl. Acad. Sci. USA 79:6661-6665, 1982; Seno et al., Nuc. Acids Res. 11:719-726, 1983; Riechmann et al., Nature 332:323-327, 1988; Amster et al., Nuc. Acids Res. 8:2055-2065, 1980; Rusconi and Kohler, Nature 314:330-334, 1985; Boss et al., Nuc. Acids Res. 12:3791-3806, 1984; Bothwell et al., Nature 298:380-382, 1982; van der Loo et al., Immunogenetics 42:333-341, 1995; Karlin et al., J. Mol. Evol. 22:195-208, 1985; Kindsvogel et al., DNA 1:335-343, 1982; Breiner et al., Gene 18:165-174, 1982; Kondo et al., Eur. J. Immunol. 23:245-249, 1993; and GenBank Accession No. J00228. For a review of immunoglobulin structure and function, see Putnam, The Plasma Proteins, Vol V, Academic Press, Inc., 49-140, 1987; and Padlan, Mol. Immunol. 31:169-217, 1994.

An "immunoglobulin hinge" is that portion of an immunoglobulin heavy chain connecting the variable and CH1 domains. Within SEQ ID NO:27, the hinge is approximately residues 99 to 113 (Eu residues 216-230 as shown in FIG. 1A).

The terms "Fc fragment," "Fc region," or "Fc domain," as used herein, are synonymous and refer to the portion of an antibody that is responsible for binding to antibody receptors on cells and the C1q component of complement. Fc stands for "fragment crystalline," the fragment of an antibody that will readily form a protein crystal. Distinct protein fragments, which were originally described by proteolytic digestion, can define the overall general structure of an immunoglobulin protein. As originally defined in the literature, the Fc fragment consists of the disulfide-linked heavy chain hinge regions, CH2, and CH3 domains. However, more recently the term has been applied to a single chain consisting of CH3, CH2, and at least a portion of the hinge sufficient to form a disulfide-linked dimer with a second such chain. As used herein, the term Fc includes variants of naturally occurring sequences.

"Dimerizing domain," as used herein, refers to a polypeptide having affinity for a second polypeptide, such that the two polypeptides associate under physiological conditions to form a dimer. The second polypeptide may be the same or a different polypeptide. The polypeptides may interact with each other through covalent and/or non-covalent association(s). Examples of dimerizing domains include an Fc region; a hinge region; a CH3 domain; a CH4 domain; a CH1 or CL domain; a leucine zipper domain (e.g., a jun/fos leucine zipper domain, see, e.g., Kostelney et al., J. Immunol., 148: 1547-1553, 1992; or a yeast GCN4 leucine zipper domain); an isoleucine zipper domain; a dimerizing region of a dimerizing cell-surface receptor (e.g., interleukin-8 receptor (IL-8R); or an integrin heterodimer such as LFA-1 or GPIIIb/IIIa); a dimerizing region of a secreted, dimerizing ligand (e.g., nerve growth factor (NGF), neurotrophin-3 (NT-3), interleukin-8 (IL-8), vascular endothelial growth factor (VEGF), or brain-derived neurotrophic factor (BDNF); see, e.g., Arakawa et al., J. Biol. Chem. 269:27833-27839, 1994, and Radziejewski et al., Biochem. 32:1350, 1993); and a polypeptide comprising at least one cysteine residue (e.g., from about one, two, or three to about ten cysteine residues) such that disulfide bond(s) can form between the polypeptide and a second polypeptide comprising at least one cysteine residue (hereinafter "a synthetic hinge"). A preferred dimerizing domain in accordance with the present invention is an Fc region.

The term "linker" or "polypeptide linker" is used herein to indicate two or more amino acids joined by peptide bond(s) and linking two discrete, separate polypeptide regions. The linker is typically designed to allow the separate polypeptide regions to perform their separate functions (such as, e.g., where a dimerizing domain, linked to other polypeptide regions, associates with another, corresponding dimerization domain to form a dimer). The linker can be a portion of a native sequence, a variant thereof, or a synthetic sequence. Linkers are also referred to herein using the abbreviation "L." The use of a subscript (e.g., "1" or "2") with "L" is used herein to differentiate among multiple linkers within a polypeptide chain, which linkers may be the same or different with respect to amino acid sequence.

The term "variant VSTM3 gene" or "variant B7R1 gene" refers to nucleic acid molecules that encode a polypeptide having an amino acid sequence that is a modification of SEQ ID NO:2. Such variants include naturally-occurring polymorphisms of VSTM3 (B7R1) genes, as well as synthetic genes that contain conservative amino acid substitutions of the amino acid sequence of SEQ ID NO:2. Additional variant forms of VSTM3 genes are nucleic acid molecules that contain insertions or deletions of the nucleotide sequences described herein. A variant VSTM3 gene can be identified, for example, by determining whether the gene hybridizes with a nucleic acid molecule having the nucleotide sequence of SEQ ID NO:1, or its complement, under stringent conditions.

Alternatively, variant VSTM3 genes can be identified by sequence comparison. Two amino acid sequences have "100% amino acid sequence identity" if the amino acid residues of the two amino acid sequences are the same when aligned for maximal correspondence. Similarly, two nucleotide sequences have "100% nucleotide sequence identity" if the nucleotide residues of the two nucleotide sequences are the same when aligned for maximal correspondence. Sequence comparisons can be performed using standard software programs such as those included in the LASERGENE bioinformatics computing suite, which is produced by DNASTAR (Madison, Wis.). Other methods for comparing two nucleotide or amino acid sequences by determining optimal alignment are well-known to those of skill in the art. (See, e.g., Peruski and Peruski, The Internet and the New Biology: Tools for Genomic and Molecular Research (ASM Press, Inc. 1997); Wu et al. (eds.), "Information Superhighway and Computer Databases of Nucleic Acids and Proteins," in Methods in Gene Biotechnology 123-151 (CRC Press, Inc. 1997); Bishop (ed.), Guide to Human Genome Computing (2nd ed., Academic Press, Inc. 1998).) Two nucleotide or amino acid sequences are considered to have "substantially similar sequence identity" or "substantial sequence identity" if the two sequences have at least 80%, at least 90%, or at least 95% sequence identity relative to each other. Particular methods for determining sequence identity are described below.

Regardless of the particular method used to identify a variant VSTM3 gene or variant VSTM3 polypeptide, a variant gene or polypeptide encoded by a variant gene may be functionally characterized the ability to bind specifically to an anti-VSTM3 antibody. A variant VSTM3 gene or variant VSTM3 polypeptide may also be functionally characterized by the ability of the polypeptide to bind to CD155, using a biological or biochemical assay such as described herein.

The term "allelic variant" is used herein to denote any of two or more alternative forms of a gene occupying the same chromosomal locus. Allelic variation arises naturally through mutation, and may result in phenotypic polymorphism within populations. Gene mutations can be silent (no change in the encoded polypeptide) or may encode polypeptides having altered amino acid sequence. The term allelic variant is also used herein to denote a protein encoded by an allelic variant of a gene.

The term "ortholog" denotes a polypeptide or protein obtained from one species that is the functional counterpart of a polypeptide or protein from a different species. Sequence differences among orthologs are the result of speciation.

The term "T-cell-mediated immune disorder," as used herein, refers to any disease or disorder having a pathology that is mediated, at least in part, by T cell activity. T-cell-mediated immune disorders include, for example, autoimmune diseases (e.g., rheumatoid arthritis, multiple sclerosis), graft-versus-host disease (GVHD), and transplant rejection. In addition to diseases characterized predominantly by T-cell immune responses, T-cell-mediated immune disorders further include, e.g., T-cell-dependent B-cell mediated indications such as, for example, antibody-mediated autoimmunity. Such diseases or disorders are particularly amenable to treatment methods using dimeric VSTM3 (B7R1) proteins of the present invention, as described further herein.

The term "effective amount," in the context of treatment of a disease by administration of a soluble dimeric protein to a subject as described herein, refers to an amount of such molecule that is sufficient to inhibit the occurrence or ameliorate one or more symptoms of the disease. For example, in the specific context of treatment of a T-cell-mediated immune disorder by administration of a soluble dimeric VSTM3 (B7R1) protein to a subject as described herein, the term "effective amount" refers to an amount of such molecule that is sufficient to modulate a T-cell-mediated response in the subject so as to inhibit the occurrence or ameliorate one or more symptoms of the T-cell-mediated immune disorder. An effective amount of an agent is administered according to the methods of the present invention in an "effective regime." The term "effective regime" refers to a combination of amount of the agent being administered and dosage frequency adequate to accomplish treatment or prevention of the disease.

Due to the imprecision of standard analytical methods, molecular weights and lengths of polymers are understood to be approximate values. When such a value is expressed as "about" X or "approximately" X, the stated value of X will be understood to be accurate to ±10%.

BRIEF DESCRIPTION OF THE DRAWINGS

FIGS. 1A-1B illustrate the amino acid sequence of a portion of a representative human immunoglobulin γ1 heavy chain (SEQ ID NO:27) (based on Ellison et al., *Nucl. Acids Res.* 10:4071, 1982). Amino acid sequence numbers are based on the Eu index (Edelman et al., *Proc. Natl. Acad. Sci. USA* 63:78-85, 1969; Kabat et al., *Sequences of Proteins of Immunological Interest*, US Department of Health and Human Services, NIH, Bethesda, Md., 1991). The Cys residues normally involved in disulfide bonding to the light chain constant region (LC) and heavy chain constant region (HC) are indicated. Boundaries of the CHL hinge, CH2, and CH3 domains are shown.

FIGS. 2A-2C illustrate the amino acid sequences of certain immunoglobulin Fc polypeptides. Amino acid sequence numbers are based on the EU index (Kabat et al., *Sequences of Proteins of Immunological Interest*, US Department of Health and Human Services, NIH, Bethesda, 1991). The illustrated sequences include a wild-type human sequence ("wt"; SEQ ID NO:28) and five variant sequences, designated Fc-488 (SEQ ID NO:29), Fc4 (SEQ ID NO:30), Fc5 (SEQ ID NO:31), Fc6 (SEQ ID NO:32), and Fc7 (SEQ ID NO:33). The Cys residues normally involved in disulfide bonding to the light chain constant region (LC) and heavy chain constant region (HC) are indicated. A "." indicates identity to wild-type at that position. ***indicates the stop codon; the C-terminal Lys residue has been removed from Fc6. Boundaries of the hinge, $C_H2$, and $C_H3$ domains are shown.

DETAILED DESCRIPTION OF THE INVENTION

I. Overview

Figure 3A:
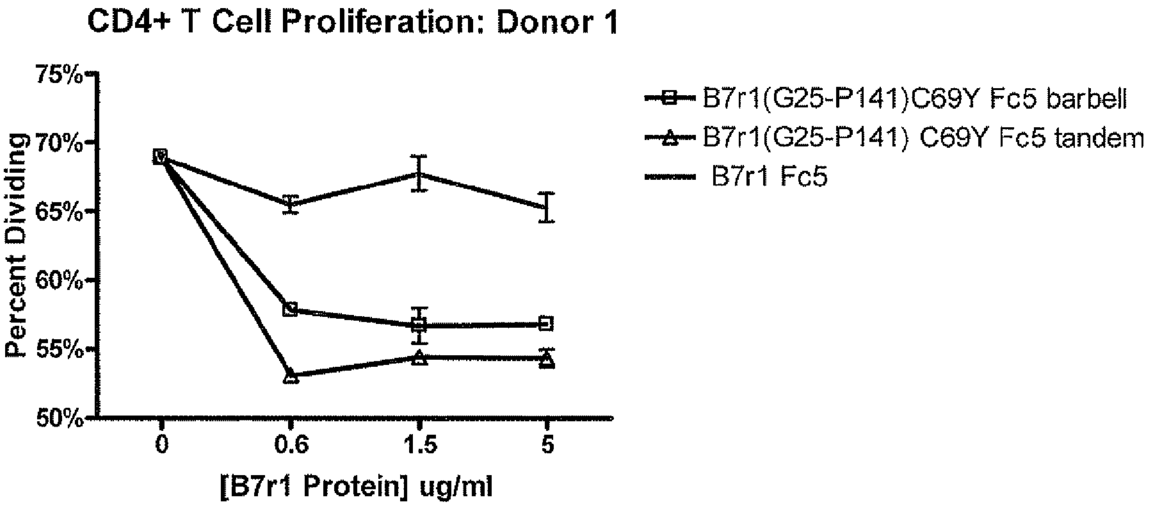
FIGS. 3A-3F depict T cell inhibition induced by soluble B7R1 (VSTM3) proteins as measured by reduced proliferative activity in vitro. Human T cells from three donors were incubated in the presence of anti-CD3 antibody and P815 cells expressing PVR either in the absence or presence of soluble B7R1 (VSTM3), as described in Example 13. Three different soluble B7R1 proteins were tested for their ability to inhibit proliferation of CD4+ (FIG. 3A-3C) or CD8+ (FIGS. 3D-3F) T cells. Three different soluble B7R1 proteins were tested: B7r1(G25-P141) C69Y Fc5 barbell, B7r1(G25-P141) C69Y Fc5 tandem, and B7r1-Fc5.
Figure 3B:
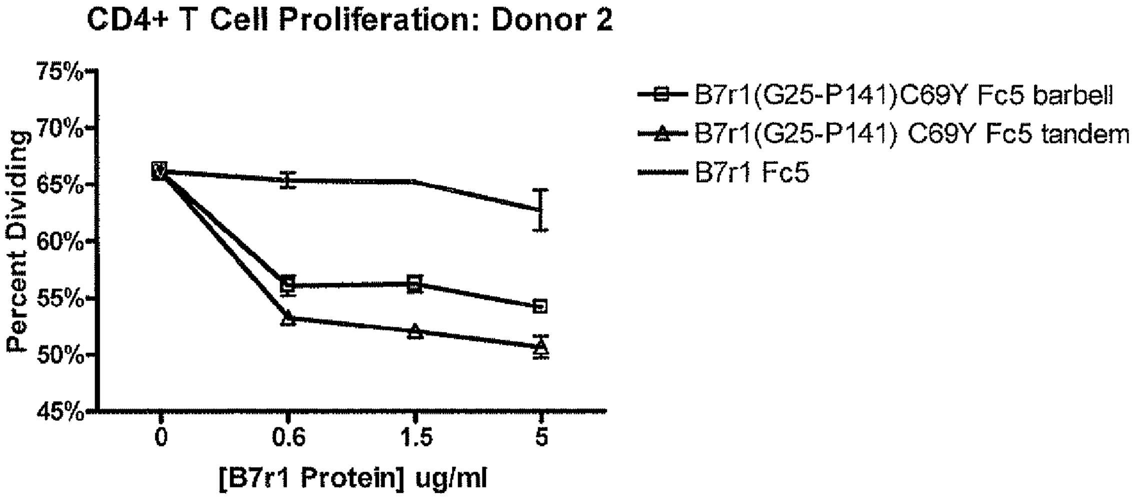
Figure 3C:
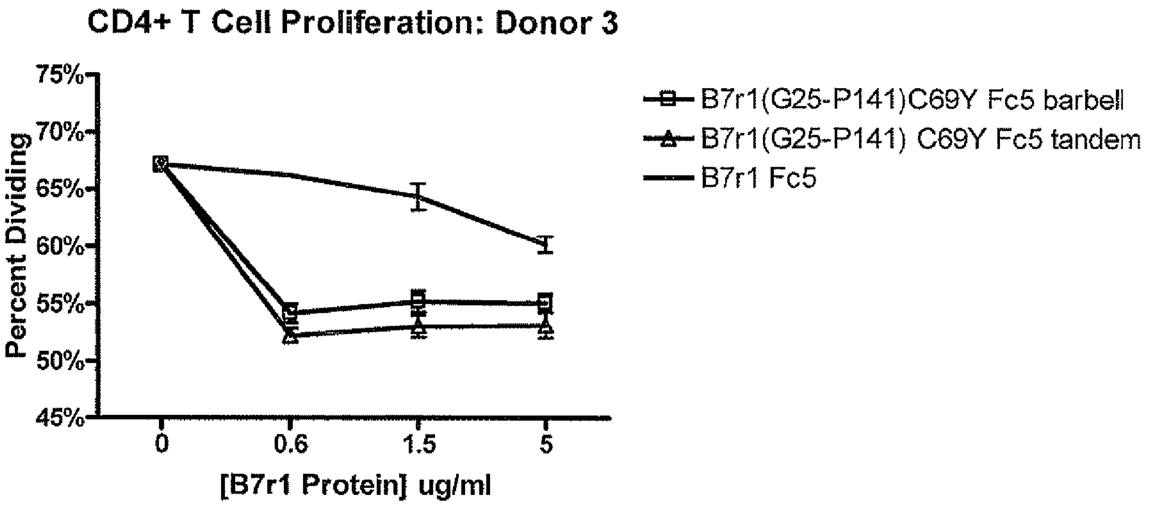
Figure 3D:
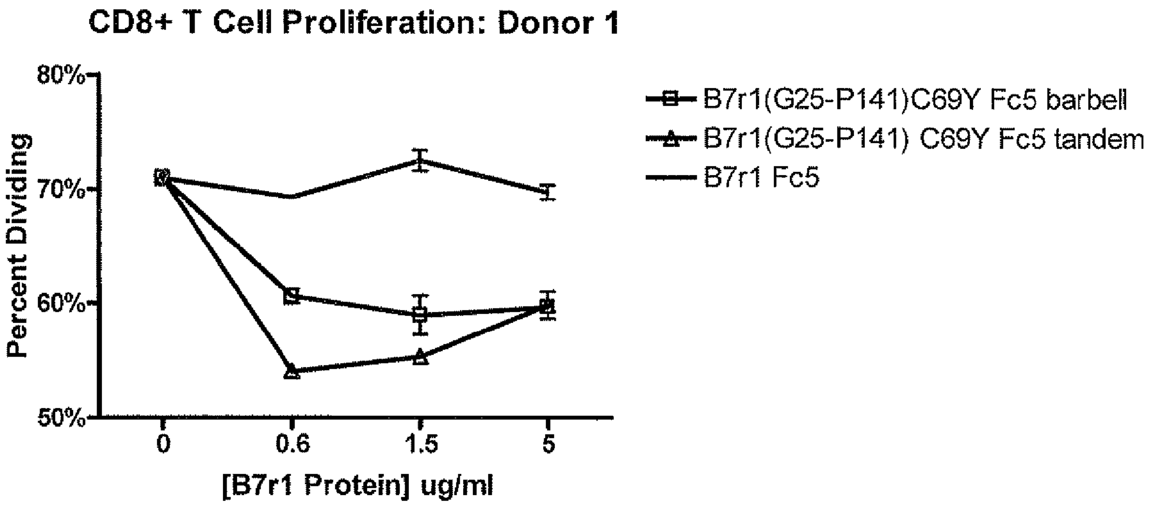
Figure 3E:
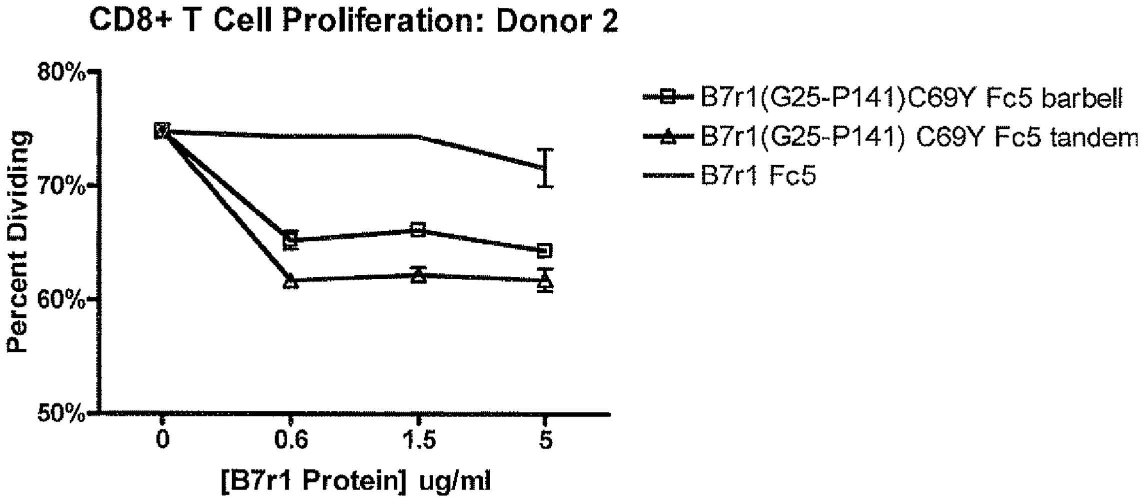
Figure 3F:
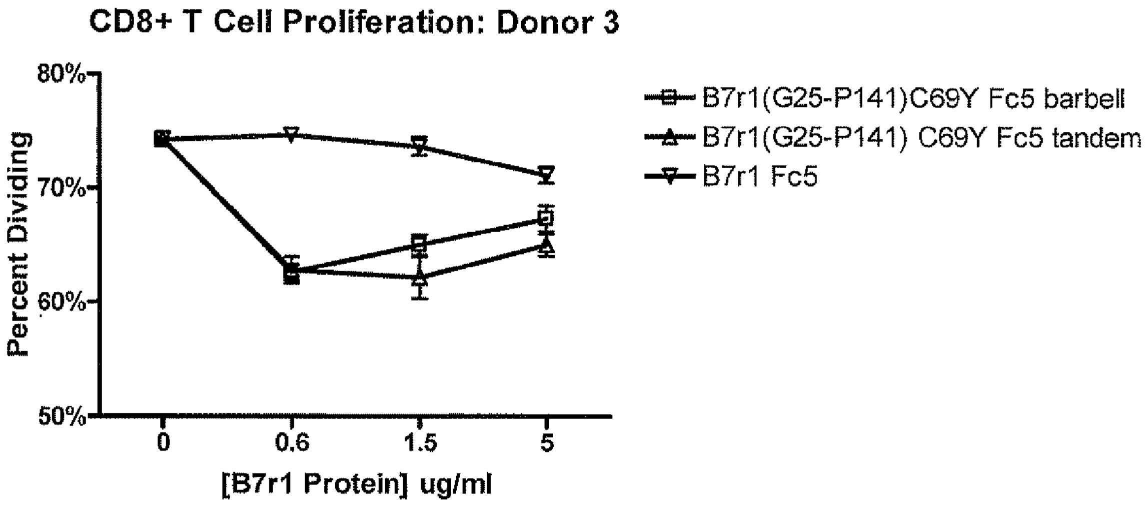

The present invention provides compositions and methods relating to soluble dimeric fusion proteins. Generally, dimeric fusion proteins of the present invention comprise first and second polypeptide chains linked via a dimerizing domain, each polypeptide chain comprising first and second polypeptide segments corresponding to a cytokine or an extracellular domain of a cell-surface receptor (also referred to herein as "monomers" or "monomer domains"). The dimeric fusion proteins are therefore generally tetravalent with respect to the monomer domains. The first and second monomer domains of each polypeptide chain may be the same or different. In certain embodiments, the monomer domains of the dimeric fusion protein are the same, providing a molecule that is tetravalent with respect to a particular monomer domain. The first and second monomer domains may be positioned, respectively, amino terminal and carboxyl terminal to the dimerizing domain (also referred to herein as a "barbell" format). Alternatively, the first and second monomer domains may both be positioned, in tandem, either carboxyl terminal or amino terminal to the dimerizing domain (also referred to herein as a "tandem" format).

In particular aspects, the present invention provides compositions and methods relating to soluble dimeric VSTM3 (B7R1) fusion proteins and their use for the treatment of T cell-mediated immune disorders, particularly T-cell-mediated autoimmune diseases. In accordance with the present invention, the dimeric VSTM3 fusions comprise first and second polypeptide chains linked via a dimerizing domain, each polypeptide chain comprising first and second monomer domains corresponding to the extracellular domain of VSTM3. The dimeric VSTM3 fusions are therefore generally tetravalent with respect to binding sites for the VSTM3 counter-receptor, CD155. The first and second monomer domains corresponding to the VSTM3 extracellular domain may be positioned in either a barbell or tandem format, as summarized above. As described further herein, dimeric VSTM3 fusion proteins in accordance with the present invention are particularly efficacious for suppression of T-cell-mediated responses in vivo.

II. Polypeptide Fusions and Dimeric Proteins

Accordingly, in one aspect, the present invention provides a soluble polypeptide fusion comprising, from amino terminus to carboxyl terminus, a formula selected from the P1-L1-D-L2-P2 and P2-L2-P1-L1-D, wherein P1 is (i) an extracellular domain of a first cell-surface receptor or a functional variant or fragment thereof, or (ii) a first cytokine or a functional variant or fragment thereof; L1 is a first polypeptide linker; D is a dimerizing domain; L2 is a second polypeptide linker; and P2 is (i) an extracellular domain of a second cell-surface receptor or a functional variant or fragment thereof, or (ii) a second cytokine or a functional variant or fragment thereof.

Within certain embodiments of the invention, P1 and P2 are the same (or derived from the same cell-surface receptor or cytokine), such that upon homodimerization of the polypeptide fusion, a protein that is tetrameric with respect to the P1/P2 monomer is provided.

In some alternative embodiments, P1 and P2 are derived from different cell-surface receptors and/or cytokines, such that upon homodimerization of the polypeptide fusion, a protein that is dimeric with respect to two different monomer domains (P1 and P2) is provided. For example, in some variations, P1 corresponds to an extracellular domain of a first cell-surface receptor and P2 corresponds to an extracellular domain of a second cell-surface receptor that is different from the first, such that homodimerization of the fusion results in a protein that is homodimeric with respect to two different cell-surface receptors, or variants or fragments thereof. Similarly, in other variations, P1 corresponds to a first cytokine and P2 corresponds to a second cytokine that is different from the first, such that homodimerization of the fusion results in a protein that is homodimeric with respect to two different cytokines, or variants or fragments thereof. In yet other variations, P1 corresponds to an extracellular domain of a cell-surface receptor and P2 corresponds to a cytokine, or vice verse, such that homodimerization of the fusion results in a protein that is homodimeric with respect to both the cell-surface receptor and the cytokine, or variants or fragments thereof.

In yet other embodiments, P1 and P2 correspond to the extracellular domains from two different subunits of a heterodimeric cell-surface receptor or, alternatively, to two different subunits of a heterodimeric cytokine. In such embodiments, polypeptide linkers L1 and L2 are designed to provide sufficient space and flexibility between monomer domains P1 and P2 within a single polypeptide fusion to allow these monomer domains to associate with each other non-covalently to form a single, functional heterodimeric unit, such that homodimerization of the fusion results in a protein having two such functional heterodimeric units.

Examples of cell-surface receptors from which P1 and/or P2 may be derived include, for example, 4-1BB; ACTH Receptor; Activin Receptors; BLTR (the Leukotriene B4 Receptor); BMP Receptor; C3a Receptor; C5a Receptor; CCR1; CCR2; CCR3; CCR4; CCR5; CCR6; CCR7; CCR8; CCR9; CD19; CD22; CD27; CD28; CD30; CD40; CD70; CD80; CD86; CTLA-4; CD226; VSTM3 (B7R1); CD112; CD155; B7H6; NKp30; ICAM; VLA-4; VCAM; CT-1 Receptor; CX3CR1; CXCR1; CXCR2; CXCR3; CXCR4; CXCR5; D6; DARC; DcR3; DR4; DR5; DcR1; DcR2; ECRF3; Fas; fMLP Receptors; G-CSF Receptor; GIT Receptor; GM-CSF Receptor; Growth Hormone Receptor; HVEM; BTLA; Interferon-α Receptor; Interferon-β Receptor; Interferon-γ Receptor; IL-1 Receptor Type I; IL-1 Receptor Type II; IL-10 Receptor; IL-11 Receptor; IL-12 Receptor; IL-13 Receptor; IL-15 Receptor; IL-16 Receptor (CD4); IL-17 Receptor A (IL-17RA); IL-17 Receptor B (IL-17RB); IL-17 Receptor C (IL-17RC); IL-17 Receptor D (IL-17RD); IL-17 Receptor E (IL-17RE); IL-18 Receptor; IL-2 Receptor; IL-3 Receptor; IL-4 Receptor; IL-5 Receptor; IL-6 Receptor; IL-7 Receptor; IL-9 Receptor; IL-20 Receptor A (IL-20RA); IL-20 Receptor B (IL-20RB); IL-21 Receptor; IL-22 Receptor A (IL-22RA); IL-22 Receptor B (IL-22RB); IL-28 Receptor A (IL-28RA); IL-27 Receptor A (IL-27RA); IL-31-Receptor A (IL-28RA); BCMA; TACI; BAFF receptor; Immunoregulatory Semaphorin Receptor CD72; Kaposi's Sarcoma-associated Herpesvirus GPCR; Lipoxin A4 Receptor; Lymphotoxin β Receptor; Lysophospholipid Growth Factor Receptors; Neurokinin 1; Opioid μ, δ, and κ Receptors for Endorphins; Oncostatin M Receptor; Osteopontin Receptor; Osteoprotegerin; Ox40; PACAP and VIP Receptors; PAF Receptors; Poxvirus; IFNα/β Receptor Homologs; Poxvirus IFNγReceptor Homologs; Poxvirus IL-1β Receptor Homologs; Poxvirus Membrane-bound G Protein-coupled Receptor Homologs; Poxvirus Secreted Chemokine-binding Proteins; Poxvirus TNF Receptor Homologs; Prolactin Receptor; RANK; RON Receptor; SCF Receptor; Somatostatin Receptors; T1/ST2; TGF-beta Receptors; TNF Receptors (e.g., p60 and p80); TNFRSF19; TPO Receptor; US28; XCR1; Erythropoietin receptor; growth hormone receptor; Leukemia inhibitory factor receptor; and C-kit receptor.

Examples of cytokines from which P1 and/or P2 may be derived include, for example, α-MSH; 9E3/cCAF; ACTH; Activin; AK155; Angiostatin; Apo2L/TRAIL; APRIL; BAFF (BLys); BLR1 Ligand/BCA-1/BLC/CXCL13; BMP Family; BRAK; Calcitonin Gene-related Peptide (CGRP); CC Chemokine of Molluscum Contagiosum Virus; CCL27; CCL28; CD100/Sema4D; CD27 Ligand; CD30 Ligand; CD40 Ligand; CKβ8-1/MPIF-1/CCL23; CLF/CLC; CSF-1; CT-1; CTAP-III, βTG, and NAP-2//CXCL7; CXCL16; Defensins; ELC/MIP-3β/Exodus-3/CCL19; ENA-78/CXCL5; Endorphins; Endostatin; Eotaxin 2/MPIF-2/CCL24; Eotaxin/CCL11; Erythropoietin; Exodus-1/LARC/MIP-3α (SCYA 20); Fas Ligand; Flt-3 Ligand; fMLP; Fractalkine/CX3CL1; G-CSF; GCP-2/CXCL6; GM-CSF; Growth Hormone; HCC-1/CCL14; HCC-4/CCL16; High Mobility Group Box 1 (HMGB1); Human Cathelicidin Antimicrobial Peptide LL-37; I-309/CCL1; IFNα, IFNβ, and IFNω Ligands; IL-1α; IL-1β; IL-10; IL-11; IL-12; IL-13; IL-15; IL-16; IL-17A; IL-17B; IL-17C; IL-17D; IL-17E; IL-17F; IL-18; IL-1Ra; IL-2; IL-27; IL-3; IL-4; IL-5; IL-6; IL-7; IL-8/CXCL8; IL-9; IP-10/CXCL10; IL-19; IL-20; IL-21; IL-22; IL-23; IL-24; IL-26; IL-31; Keratinocyte Growth Factor; KSHV-related IL-6 Ligand; Leptin; Leukotactin 1/HCC-2/MIP-1δ/CCL15; Leukotriene B4; LIGHT; Lipoxin; Lymphotactin/XCL1; Lymphotoxin α and β; Lysophospholipid Growth Factors; Macrophage-derived Chemokine; Macrophage-Stimulating Protein (MSP); MCP-1/CCL2, MCP-2/CCL8, MCP-3/CCL7, MCP-4/CCL13, and MCP-5/CCL12; Methoxyestradiol; MGSA/GRO/CXCL1, CXCL2, CXCL3; MIF; MIG/CXCL9; MIP-1α/CCL3, MIP-1β/CCL4; MIP-1γ/MRP-2/CCF18/CCL9/10; Mu C10/CCL6; Oncostatin M; Osteopontin; Parapoxvirus (Orf Virus) IL-10 Homolog; PARC/DC-CCK1/AMAC-1/CCL18; PDGF-A; PDGF-B; PDGF-C; PDGF-D; Platelet-Activating Factor; Platelet Factor 4/CXCL4; Poxvirus Growth Factors Related to Epidermal Growth Factor; Poxvirus Secreted Complement Control Proteins; Poxvirus Vascular Endothelial Growth Factor (VEGF) Homologs of Orf Virus; Prolactin; RANK Ligand; RANTES/CCL5; S100A12; SDF-1/CXCL12; SERP-1, a Secreted Poxyiral Serpin; SLC (6Ckine)/Exodus-2/TCA-4/CCL21; Somatostatin; Stem Cell Factor; Substance P; TARC/CCL17; TCA3/Mouse CCL1; TECK/CCL25; TGFβ; Thrombopoietin; TNFα; TSG-6; TWEAK; Vaccinia Virus Semaphorin; vCXC-1 and vCXC-2; VEGF; VIP and PACAP; and Viral IL-10 Variants.

Functional variants or fragments of a particular extracellular domain of a cell-surface receptor can be readily identified using routine biological or biochemical assays for assessing the ability of the variant or fragment to specifically bind to a cognate ligand or counter-receptor of the cell-surface receptor. Similarly, functional variants or fragments of a particular cytokine can be readily identified using routine biological or biochemical assays for assessing the ability of the variant or fragment to specifically bind to a cognate receptor of the cytokine.

Functional variants of a particular reference polypeptide (e.g., a wild-type cytokine or an extracellular domain of a wild-type cell-surface receptor such as, for example, an extracellular domain of VSTM3 (B7R1)) are generally characterized as having one or more amino acid substitutions, deletions or additions relative to the reference polypeptide. These changes are preferably of a minor nature, that is conservative amino acid substitutions (see, e.g., Table 1, infra, which lists some exemplary conservative amino acid substitutions) and other substitutions that do not significantly affect the folding or activity of the protein or polypeptide; small deletions, typically of one to about 30 amino acids; and small amino- or carboxyl-terminal extensions, such as an amino-terminal methionine residue, a small linker peptide of up to about 20-25 residues, or a small extension that facilitates purification (an affinity tag), such as a poly-histidine tract, protein A (Nilsson et al., *EMBO J.* 4:1075, 1985; Nilsson et al., *Methods Enzymol.* 198:3, 1991), glutathione S transferase (Smith and Johnson, Gene 67:31, 1988), or other antigenic epitope or binding domain. (See generally Ford et al., *Protein Expression and Purification* 2:95-107, 1991.) DNAs encoding affinity tags are available from commercial suppliers (e.g., Pharmacia Biotech, Piscataway, N.J.).

TABLE 1

Conservative amino acid substitutions

| Basic | Acidic | Polar | Hydrophobic | Aromatic | Small |
|---|---|---|---|---|---|
| Arginine | Glutamate | Glutamine | Leucine | phenylalanine | glycine |
| Lysine | Aspartate | Asparagines | Isoleucine | tryptophan | alanine |
| histidine | | | Valine | tyrosine | serine |
| | | | Methionine | | threionine |
| | | | | | methionine |

Essential amino acids in a receptor or cytokine polypeptide can be identified according to procedures known in the art, such as site-directed mutagenesis or alanine-scanning mutagenesis (Cunningham and Wells, *Science* 244:1081-1085, 1989; Bass et al., *Proc. Natl. Acad. Sci. USA* 88:4498-4502, 1991). In the latter technique, single alanine mutations are introduced at every residue in the molecule, and the resultant mutant molecules are tested for biological activity (e.g., ligand binding and signal transduction) to identify amino acid residues that are critical to the activity of the molecule. Sites of ligand-receptor interaction can also be determined by analysis of crystal structure as determined by such techniques as nuclear magnetic resonance, crystallography or photoaffinity labeling. (See, e.g., de Vos et al., *Science* 255:306-312, 1992; Smith et al., *J. Mol. Biol.* 224:899-904, 1992; Wlodaver et al., *FEBS Lett.* 309:59-64, 1992.) The identities of essential amino acids can also be inferred from analysis of homologies with related receptors or cytokines.

Multiple amino acid substitutions can be made and tested using known methods of mutagenesis and screening, such as those disclosed by Reidhaar-Olson and Sauer *Science* 241: 53-57, 1988 or Bowie and Sauer *Proc. Natl. Acad. Sci. USA* 86:2152-2156, 1989. Briefly, these authors disclose methods for simultaneously randomizing two or more positions in a polypeptide, selecting for functional polypeptide, and then sequencing the mutagenized polypeptides to determine the spectrum of allowable substitutions at each position. Other methods that can be used include phage display e.g., Lowman et al., *Biochem.* 30:10832-10837, 1991; Ladner et al., U.S. Pat. No. 5,223,409; Huse, WIPO Publication WO 92/06204) and region-directed mutagenesis (Derbyshire et al., *Gene* 46:145, 1986; Ner et al., *DNA* 7:127, 1988).

Variant nucleotide and polypeptide sequences can also be generated through DNA shuffling. (See, e.g., Stemmer, *Nature* 370:389, 1994; Stemmer, *Proc. Nat'l Acad. Sci. USA* 91:10747, 1994; International Publication No. WO 97/20078.) Briefly, variant DNA molecules are generated by in vitro homologous recombination by random fragmentation of a parent DNA followed by reassembly using PCR, resulting in randomly introduced point mutations. This technique can be modified by using a family of parent DNA molecules, such as allelic variants or DNA molecules from different species, to introduce additional variability into the process. Selection or screening for the desired activity, followed by additional iterations of mutagenesis and assay provides for rapid "evolution" of sequences by selecting for desirable mutations while simultaneously selecting against detrimental changes.

Mutagenesis methods as disclosed above can be combined with high-throughput screening methods to detect activity of cloned, mutagenized receptors in host cells. Preferred assays in this regard include cell proliferation assays and biosensor-based ligand-binding assays, which are described below. Mutagenized DNA molecules that encode active receptor or cytokine variants can be recovered from the host cells and rapidly sequenced using modern equipment. These methods allow the rapid determination of the importance of individual amino acid residues in a polypeptide of interest, and can be applied to polypeptides of unknown structure.

As previously discussed, a polypeptide fusion in accordance with the present invention can include a polypeptide segment corresponding to a "functional fragment" of a particular cytokine or extracellular domain of a cell-surface receptor. Routine deletion analyses of nucleic acid molecules can be performed to obtain functional fragments of a nucleic acid molecule encoding a given cytokine or extracellular domain of a cell-surface receptor. As an illustration, VSTM3-encoding DNA molecules having the nucleotide sequence of residues 73-423 of SEQ ID NO:1 can be digested with Bal31 nuclease to obtain a series of nested deletions. The fragments are then inserted into expression vectors in proper reading frame, and the expressed polypeptides are isolated and tested for the ability to bind CD155 or CD112. One alternative to exonuclease digestion is to use oligonucleotide-directed mutagenesis to introduce deletions or stop codons to specify production of a desired fragment. Alternatively, particular fragments of a gene encoding a cytokine or receptor can be synthesized using the polymerase chain reaction.

This general approach is exemplified by studies on the truncation at either or both termini of interferons. (See Horisberger and Di Marco, *Pharmac. Ther.* 66:507, 1995.) Moreover, standard techniques for functional analysis of proteins are described by, for example, Treuter et al., *Molec. Gen. Genet.* 240:113, 1993; Content et al., "Expression and preliminary deletion analysis of the 42 kDa 2-5A synthetase induced by human interferon," in *Biological Interferon Systems, Proceedings of ISIR-TNO Meeting on Interferon Systems* 65-72 (Cantell, ed., Nijhoff 1987); Herschman, "The EGF Receptor," in *Control of Animal Cell Proliferation, Vol.* 1 169-199 (Boynton et al., eds., Academic Press 1985); Coumailleau et al., *J. Biol. Chem.* 270:29270, 1995; Fukunaga et al., *J. Biol. Chem.* 270:25291, 1995; Yamaguchi et al., *Biochem. Pharmacol.* 50:1295, 1995; and Meisel et al., *Plant Molec. Biol.* 30:1, 1996.

Using the methods discussed above, one of ordinary skill in the art can prepare a variety of polypeptides that (i) are substantially identical to a reference polypeptide corresponding to a soluble cytokine or extracellular domain of a cell-surface receptor and (ii) retains the functional binding properties of the reference polypeptide. Assay systems for determining receptor- or ligand-binding properties of cytokine or receptor polypeptides are generally known in the art and are readily adaptable for use in determining the functional binding properties of a soluble polypeptide fusion of the formula P1-L1-D-L2-P2 and P2-L2-P1-L1-D, where P1 and/or P2 corresponds to a cytokine or cell-surface receptor variant. Exemplary assays are further described herein.

For example, a preferred assay system employs a commercially available biosensor instrument (BIAcore™, Pharmacia Biosensor, Piscataway, N.J.), wherein a receptor polypeptide is immobilized onto the surface of a receptor chip. Use of this instrument is disclosed by Karlsson (*J. Immunol. Methods* 145:229-240, 1991) and Cunningham and Wells (*J. Mol. Biol.* 234:554-563, 1993). For use in accordance with the present invention, a soluble polypeptide fusion (e.g., a soluble VSTM3 polypeptide fusion) in accordance with the invention is covalently attached, using amine or sulfhydryl chemistry, to dextran fibers that are attached to gold film within the flow cell. A test sample is passed through the cell. If ligand (e.g., in the case of a soluble VSTM3 polypeptide fusion, soluble CD155 or CD112) is present in the sample, it will bind to the immobilized polypeptide fusion, causing a change in the refractive index of the medium, which is detected as a change in surface plasmon resonance of the gold film. This system allows the determination of on- and off-rates, from which binding affinity can be calculated, and assessment of stoichiometry of binding.

The soluble polypeptide fusions can also be used within other assay systems known in the art. Such systems include Scatchard analysis for determination of binding affinity (see Scatchard, *Ann. NY Acad. Sci.* 51: 660-672, 1949) and calorimetric assays (see Cunningham et al., *Science* 253:545-548, 1991; Cunningham et al., *Science* 254:821-825, 1991).

In certain embodiments, P1 and P2 are derived from the extracellular domain of the cell-surface receptor VSTM3 (B7R1). Accordingly, in some embodiments, a soluble polypeptide fusion in accordance with the present invention comprises, from amino terminus to carboxyl terminus, a formula selected from P1-L1-D-L2-P2 and P2-L2-P1-L1-D, wherein P1 is a first polypeptide having at least 80% sequence identity with the extracellular domain of a VSTM3 polypeptide, or at least 80% sequence identity with a functional fragment of the VSTM3 extracellular domain; L1 is a first polypeptide linker; D is a dimerizing domain; L2 is a second polypeptide linker; and P2 is a second polypeptide having at least 80% sequence identity with the extracellular domain of a VSTM3 polypeptide, or at least 80% sequence identity with a functional fragment of the VSTM3 extracellular domain; wherein the polypeptide fusion is capable of specifically binding to the extracellular domain of a CD155 polypeptide (e.g., amino acid residues 28-343 of SEQ ID NO:22 or amino acid residues 29-345 of SEQ ID NO:24). In certain embodiments, P1 and/or P2 have at least 90% or at least 95% sequence identity with the extracellular domain of the VSTM3 polypeptide or functional fragment thereof. For example, in some variations, P1 and/or P2 have 100% sequence identity with the extracellular domain of the VSTM3 polypeptide or functional fragment thereof P1 and/or P2 may be derived, for example, from the extracellular domain of a human or murine VSTM3 polypeptide (e.g., residues 22-141 or SEQ ID NO:2 or residues 26-138 of SEQ ID NO:4), or from a functional fragment thereof.

For example, in certain embodiments, P1 and/or P2 have at least 80%, at least 90%, or at least 95% identity with amino acid residues 25-141 of SEQ ID NO:2; or P1 and/or P2 have at least 80%, at least 90%, or at least 95% identity with amino acid residues 26-138 of SEQ ID NO:4. In some such variations, one or both of P1 and P2 has 100% identity with amino acid residues 25-141 of SEQ ID NO:2, or one or both of P1 and P2 has 100% identity with amino acid residues 26-138 of SEQ ID NO:4. In other variations, one or both of P1 and P2 comprises a non-cysteine residue (e.g., tyrosine) at the amino acid position corresponding to residue 69 of SEQ ID NO:2. Particularly suitable P1 and/or P2 polypeptides have the amino acid sequence shown in residues 23-139 of SEQ ID NO:18 (residues 23-139 of SEQ ID NO:20).

In other embodiments, P1 and/or P2 have at least 80%, at least 90%, or at least 95% identity with amino acid residues 23-139 of SEQ ID NO:18 (residues 23-139 of SEQ ID NO:20). In some such variations, P1 and/or P2 has a non-cysteine residue at the amino acid position corresponding to residue 67 of SEQ ID NO:18. For example, in particular variations, the P1 and/or P2 polypeptide having at least 80%, at least 90%, or at least 95% identity with amino acid residues 23-139 of SEQ ID NO:18 retains the tyrosine residue corresponding to tyrosine 67 of SEQ ID NO:18.

Percent sequence identity is determined by conventional methods. See, e.g., Altschul et al., *Bull. Math. Bio.* 48:603, 1986, and Henikoff and Henikoff, *Proc. Natl. Acad. Sci. USA* 89:10915, 1992. For example, two amino acid sequences can be aligned to optimize the alignment scores using a gap opening penalty of 10, a gap extension penalty of 1, and the "BLOSUM62" scoring matrix of Henikoff and Henikoff, supra, as shown in Table 2 (amino acids are indicated by the standard one-letter codes). The percent identity is then calculated as: ([Total number of identical matches]/[length of the longer sequence plus the number of gaps introduced into the longer sequence in order to align the two sequences])(100).

TABLE 2

BLOSUM62 Scoring Matrix

| | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | 4 | | | | | | | | | | | | | | | | | | | |
| R | −1 | 5 | | | | | | | | | | | | | | | | | | |
| N | −2 | 0 | 6 | | | | | | | | | | | | | | | | | |
| D | −2 | −2 | 1 | 6 | | | | | | | | | | | | | | | | |
| C | 0 | −3 | −3 | −3 | 9 | | | | | | | | | | | | | | | |
| Q | −1 | 1 | 0 | 0 | −3 | 5 | | | | | | | | | | | | | | |
| E | −1 | 0 | 0 | 2 | −4 | 2 | 5 | | | | | | | | | | | | | |
| G | 0 | −2 | 0 | −1 | −3 | −2 | −2 | 6 | | | | | | | | | | | | |

TABLE 2-continued

| BLOSUM62 Scoring Matrix | | | | | | | | | | | | | | | | | | | | |
|---|---|---|---|---|---|---|---|---|---|---|---|---|---|---|---|---|---|---|---|---|
| | A | R | N | D | C | Q | E | G | H | I | L | K | M | F | P | S | T | W | Y | V |
| H | -2 | 0 | 1 | -1 | -3 | 0 | 0 | -2 | 8 | | | | | | | | | | | |
| I | -1 | -3 | -3 | -3 | -1 | -3 | -3 | -4 | -3 | 4 | | | | | | | | | | |
| L | -1 | -2 | -3 | -4 | -1 | -2 | -3 | -4 | -3 | 2 | 4 | | | | | | | | | |
| K | -1 | 2 | 0 | -1 | -3 | 1 | 1 | -2 | -1 | -3 | -2 | 5 | | | | | | | | |
| M | -1 | -1 | -2 | -3 | -1 | 0 | -2 | -3 | -2 | 1 | 2 | -1 | 5 | | | | | | | |
| F | -2 | -3 | -3 | -3 | -2 | -3 | -3 | -3 | -1 | 0 | 0 | -3 | 0 | 6 | | | | | | |
| P | -1 | -2 | -2 | -1 | -3 | -1 | -1 | -2 | -2 | -3 | -3 | -1 | -2 | -4 | 7 | | | | | |
| S | 1 | -1 | 1 | 0 | -1 | 0 | 0 | 0 | -1 | -2 | -2 | 0 | -1 | -2 | -1 | 4 | | | | |
| T | 0 | -1 | 0 | -1 | -1 | -1 | -1 | -2 | -2 | -1 | -1 | -1 | -1 | -2 | -1 | 1 | 5 | | | |
| W | -3 | -3 | -4 | -4 | -2 | -2 | -3 | -3 | -2 | -2 | -3 | -2 | -3 | -1 | 1 | -4 | -3 | 2 | 11 | |
| Y | -2 | -2 | -2 | -3 | -2 | -1 | -2 | -3 | 2 | -1 | -1 | -2 | -1 | 3 | -3 | -2 | -2 | 2 | 7 | |
| V | 0 | -3 | -3 | -3 | -1 | -2 | -2 | -3 | -3 | 3 | 1 | -2 | 1 | -1 | -2 | -2 | 0 | -3 | -1 | 4 |

Those skilled in the art appreciate that there are many established algorithms available to align two amino acid sequences. The "FASTA" similarity search algorithm of Pearson and Lipman is a suitable protein alignment method for examining the level of identity shared by an amino acid sequence disclosed herein and the amino acid sequence of a putative variant thereof. The FASTA algorithm is described by Pearson and Lipman, Proc. Nat'l Acad. Sci. USA 85:2444, 1988, and by Pearson, Meth. Enzymol. 183:63, 1990. Briefly, FastA first characterizes sequence similarity by identifying regions shared by the query sequence (e.g., residues 25-141 of SEQ ID NO:2 or residues 23-139 of SEQ ID NO:18) and a test sequence that have either the highest density of identities (if the ktup variable is 1) or pairs of identities (if ktup=2), without considering conservative amino acid substitutions, insertions, or deletions. The ten regions with the highest density of identities are then rescored by comparing the similarity of all paired amino acids using an amino acid substitution matrix, and the ends of the regions are "trimmed" to include only those residues that contribute to the highest score. If there are several regions with scores greater than the "cutoff" value (calculated by a predetermined formula based upon the length of the sequence and the ktup value), then the trimmed initial regions are examined to determine whether the regions can be joined to form an approximate alignment with gaps. Finally, the highest scoring regions of the two amino acid sequences are aligned using a modification of the Needleman-Wunsch-Sellers algorithm (Needleman and Wunsch, J. Mol. Biol. 48:444, 1970; Sellers, SIAM J. Appl. Math. 26:787, 1974), which allows for amino acid insertions and deletions. Illustrative parameters for FASTA analysis are: ktup=1, gap opening penalty=10, gap extension penalty=1, and substitution matrix=blosum62. These parameters can be introduced into a FASTA program by modifying the scoring matrix file ("SMATRIX"), as explained in Appendix 2 of Pearson, Meth. Enzymol. 183:63, 1990.

FASTA can also be used to determine the sequence identity of nucleic acid molecules using a ratio as disclosed above. For nucleotide sequence comparisons, the ktup value can range between one to six, preferably from three to six, most preferably three, with other parameters set as described above.

The present invention includes soluble VSTM3 polypeptide fusions having a conservative amino acid change compared with the amino acid sequence of SEQ ID NO:2 residues 25-141 or SEQ ID NO:18 residues 23-139 (SEQ ID NO:20 residues 23-139). For example, VSTM3 variants can be obtained that contain one or more amino acid substitutions of SEQ ID NO:2 residues 25-141 or SEQ ID NO:18 residues 23-139 in which an alkyl amino acid is substituted for an alkyl amino acid in a VSTM3 amino acid sequence, an aromatic amino acid is substituted for an aromatic amino acid in a VSTM3 amino acid sequence, a sulfur-containing amino acid is substituted for a sulfur-containing amino acid in a VSTM3 amino acid sequence, a hydroxy-containing amino acid is substituted for a hydroxy-containing amino acid in a VSTM3 amino acid sequence, an acidic amino acid is substituted for an acidic amino acid in a VSTM3 amino acid sequence, a basic amino acid is substituted for a basic amino acid in a VSTM3 amino acid sequence, or a dibasic monocarboxylic amino acid is substituted for a dibasic monocarboxylic amino acid in a VSTM3 amino acid sequence. Among the common amino acids, a "conservative amino acid substitution" is illustrated by, for example, a substitution among amino acids within each of the following groups: (1) glycine, alanine, valine, leucine, and isoleucine, (2) phenylalanine, tyrosine, and tryptophan, (3) serine and threonine, (4) aspartate and glutamate, (5) glutamine and asparagine, and (6) lysine, arginine and histidine. Exemplary groups of conservative amino acid changes are further shown in Table 1, supra.

The BLOSUM62 table (see Table 2) is an amino acid substitution matrix derived from about 2,000 local multiple alignments of protein sequence segments, representing highly conserved regions of more than 500 groups of related proteins (Henikoff and Henikoff, Proc. Nat'l Acad. Sci. USA 89:10915, 1992). Accordingly, the BLOSUM62 substitution frequencies can be used to define conservative amino acid substitutions that may be introduced into the amino acid sequences of the present invention. Although it is possible to design amino acid substitutions based solely upon chemical properties (as discussed above), the language "conservative amino acid substitution" preferably refers to a substitution represented by a BLOSUM62 value of greater than −1. For example, an amino acid substitution is conservative if the substitution is characterized by a BLOSUM62 value of 0, 1, 2, or 3. According to this system, preferred conservative amino acid substitutions are characterized by a BLOSUM62 value of at least 1 (e.g., 1, 2 or 3), while more preferred conservative amino acid substitutions are characterized by a BLOSUM62 value of at least 2 (e.g., 2 or 3). Particular variants of a cytokine or receptor polypeptide (e.g., VSTM3) are characterized by having at least 80%, at least 90%, at least 95%, at least 96%, at least 97%, at least 98%, or at least 99% sequence identity to the corresponding amino acid sequence (e.g., residues 25-141 of SEQ ID NO:2 or residues 23-139 of SEQ ID NO:18), wherein the variation in amino acid sequence is due to one or more conservative amino acid substitutions.

Various dimerization domains are suitable for use in accordance with the dimeric fusion proteins as described herein. In certain embodiments, the dimerizing domain is an immunoglobulin heavy chain constant region, such as an Fc region.

The Fc region may be a native sequence Fc region or a variant Fc region. In some embodiments, the Fc region lacks one or more effector functions (e.g., one or both of ADCC and CDC effector functions). Exemplary Fc regions lacking one or more effector functions include, for example, Fc-488, Fc4, Fc5, Fc6, and Fc7 (see FIGS. 2A-2C; SEQ ID NOs:29-33, respectively, from amino acid residue 16).

Polypeptide linkers for use in accordance with the present invention can be naturally-occurring, synthetic, or a combination of both. The linker joins two separate polypeptide regions (e.g., a dimerizing domain and a polypeptide corresponding to the extracellular domain of VSTM3 (B7R1)) and maintains the linked polypeptide regions as separate and discrete domains of a longer polypeptide. The linker can allow the separate, discrete domains to cooperate yet maintain separate properties (e.g., in the case of an Fc region dimerizing domain linked to a polypeptide corresponding to the extracellular domain of VSTM3, Fc receptor (e.g., FcRn) binding may be maintained for the Fc region, while CD155-binding properties of the VSTM3 extracellular domain will be maintained). The use of naturally occurring as well as artificial peptide linkers to connect polypeptides into novel linked fusion polypeptides is well-known in the art. (See, e.g., Hallewell et al., *J. Biol. Chem.* 264, 5260-5268, 1989; Alfthan et al., *Protein Eng.* 8, 725-731, 1995; Robinson and Sauer, *Biochemistry* 35, 109-116, 1996; Khandekar et al., *J. Biol. Chem.* 272, 32190-32197, 1997; Fares et al., *Endocrinology* 139, 2459-2464, 1998; Smallshaw et al., *Protein Eng.* 12, 623-630, 1999; U.S. Pat. No. 5,856,456.)

Typically, residues within the linker polypeptide are selected to provide an overall hydrophilic character and to be non-immunogenic and flexible. As used herein, a "flexible" linker is one that lacks a substantially stable higher-order conformation in solution, although regions of local stability are permissible. In general, small, polar, and hydrophilic residues are preferred, and bulky and hydrophobic residues are undesirable. Areas of local charge are to be avoided; if the linker polypeptide includes charged residues, they will ordinarily be positioned so as to provide a net neutral charge within a small region of the polypeptide. It is therefore preferred to place a charged residue adjacent to a residue of opposite charge. In general, preferred residues for inclusion within the linker polypeptide include Gly, Ser, Ala, Thr, Asn, and Gln; more preferred residues include Gly, Ser, Ala, and Thr; and the most preferred residues are Gly and Ser. In general, Phe, Tyr, Trp, Pro, Leu, Ile, Lys, and Arg residues will be avoided (unless present within an immunoglobulin hinge region of the linker), Pro residues due to their hydrophobicity and lack of flexibility, and Lys and Arg residues due to potential immunogenicity. Cys residues will be included, as disclosed herein, so as to provide for disulfide bonding. The sequence of the linker will also be designed to avoid unwanted proteolysis.

In some embodiments, the polypeptide linker L1 comprises or consists of from 15 to 32 amino acid residues, wherein from 1 to 8 of said residues are cysteine residues. Within a preferred embodiment of the invention, each linker contains exactly two cysteine residues. The linker is designed to provide sufficient space and flexibility between the dimerizing domain and the P1 polypeptide (e.g., a P1 polypeptide corresponding to the VSTM3 extracellular domain) to allow the domains to perform their intended functions within the polypeptide. The linker length and composition are selected to provide the desired spacing and degree of flexibility, while also providing for one or more interchain disulfide bonds to stabilize the desired conformation.

In particular variations, L1 is an immunoglobulin hinge region, or a fragment or variant of an immunoglobulin hinge region. Within one embodiment of the invention, the N-terminal most cysteine residue (Eu residue 220; residue 103 of SEQ ID NO:27), which in an assembled, native antibody forms a disulfide bond with an immunoglobulin light chain, is omitted from the hinge, either by replacement with another amino acid residue (e.g., Ser) or by deletion or truncation. Other changes in the hinge sequence can also be made. For example the Lys residue (Eu 218; residue 101 of SEQ ID NO:27) can be changed to Arg. The polypeptide linker can thus comprise an immunoglobulin hinge region, or a fragment or variant thereof, that contains at least two cysteine residues that form disulfide bonds with the polypeptide linker on the other chain. An immunoglobulin hinge region can be obtained from any immunoglobulin heavy chain. Gamma (IgG) hinge regions, such as the γ1 hinge, have been well characterized and are conveniently used within the present invention.

Exemplary L2 polypeptide linkers comprise a plurality of glycine resides. For example, in some embodiments, an L2 polypeptide linker comprises a plurality of glycine residues and optionally at least one serine residue. In particular variations of a polypeptide comprising the formula P1-L1-D-L2-P2, L2 comprises the formula Gly-Gly-Gly-Ser-Gly (SEQ ID NO:21). In particular variations of a polypeptide comprising the formula P2-L2-P1-L1-D, an L2 polypeptide linker comprises comprises the formula [Gly-Gly-Gly-Ser]n (SEQ ID NO:22), wherein n is an integer from 3 to 5. In a specific variation of an L2 linker comprising the formula [Gly-Gly-Gly-Ser]n, n is 4.

Polypeptide segments used within the present invention (e.g., polypeptide segments corresponding to a VSTM3 extracellular domain, linkers comprising an immunoglobulin hinge region, and dimerizing domains such as Fc fragments) can be obtained from a variety of species. If the dimeric protein is to be used therapeutically in humans, it is preferred that human polypeptide sequences be employed. However, non-human sequences can be used, as can variant sequences. For other uses, including in vitro diagnostic uses and veterinary uses, polypeptide sequences from humans or non-human animals can be employed, although sequences from the same species as the patient may be preferred for in vivo veterinary use or for in vitro uses where species specificity of intermolecular reactions is present. Thus, polypeptide segments for use within the present invention can be, without limitation, human, non-human primate, rodent, canine, feline, equine, bovine, ovine, porcine, lagomorph, and avian polypeptides, as well as variants thereof.

In specific embodiments of a polypeptide fusion comprising the formula P1-L1-D-L2-P2 and in which each of P1 and P2 are derived from the extracellular domain of VSTM3 (B7R1), the polypeptide fusion comprises the amino acid sequence shown in residues 23-493 or 1-493 of SEQ ID NO:18; residues 22-498 or 1-498 of SEQ ID NO:6; residues 26-489 or 1-489 of SEQ ID NO:10, residues 36-506 or 1-506 of SEQ ID NO:14, residues 36-506 or 1-506 of SEQ ID NO:16, or residues 23-493 or 1-493 of SEQ ID NO:18. In specific embodiments of a polypeptide fusion comprising the formula P2-L2-P1-L1-D and in which each of P1 and P2 are derived from the extracellular domain of VSTM3, the polypeptide fusion comprises the amino acid sequence shown in residues 23-508, 23-507, 1-508, or 1-507 of SEQ ID NO:20; residues 22-513, 22-512, 1-513, or 1-512 of SEQ ID NO:8; residues 26-504, 26-503, 1-504, or 1-503 of SEQ ID NO:12; or residues 23-508, 23-507, 1-508, or 1-507 or SEQ ID NO:20.

The present invention also provides dimeric proteins comprising first and second polypeptide fusions as described above. Accordingly, in another aspect, the present invention provides a dimeric protein comprising a first polypeptide fusion and a second polypeptide fusion, where each of the first and second polypeptide fusions comprises, from amino terminus to carboxyl terminus, P1-L1-D1-L2-P2 or P2-L2-P1-L1-D as described herein. For example, in particular embodiments, a dimeric VSTM3 (B7R1) protein in accordance with the present invention comprises a first polypeptide fusion and a second polypeptide fusion, where each of the first and second polypeptide fusions comprises, from amino terminus to carboxyl terminus, P1-L1-D1-L2-P2, where each of P1 and P2 is derived from the extracellular domain of VSTM3, and where the dimeric protein is capable of specifically binding to the extracellular domain of CD155 (e.g., amino acid residues 28-343 of SEQ ID NO:22). In other embodiments, a dimeric VSTM3 protein in accordance with the present invention comprises a first polypeptide fusion and a second polypeptide fusion, where each of the first and second polypeptide fusions comprises, from amino terminus to carboxyl terminus, P2-L2-P1-L1-D, where each of P1 and P2 is derived from the extracellular domain of VSTM3, and where the dimeric protein is capable of specifically binding to the extracellular domain of CD155.

III. Materials and Methods for Making Polypeptide Fusions and Dimeric Proteins The present invention also provides polynucleotide molecules, including DNA and RNA molecules, that encode the fusion polypeptides disclosed above. The polynucleotides of the present invention include both single-stranded and double-stranded molecules. Polynucleotides encoding various segments of a polypeptide fusion (e.g., a dimerizing domain such as an Fc fragment; P1 and P2 polypeptide segments) can be generated and linked together to form a polynucleotide encoding a polypeptide fusion as described herein using known methods for recombinant manipulation of nucleic acids.

DNA sequences encoding cytokines and cell-surface receptors (e.g., VSTM3 (B7R1)), including polypeptide segments corresponding to extracellular domains of such receptors, are known in the art. DNA sequences encoding various dimerizing domains (e.g., immunoglobulin heavy chain constant regions such as Fc fragments) are also known. Additional DNA sequences encoding cytokine, cell-surface receptor, and dimerizing domain polypeptides can be readily generated by those of ordinary skill in the art based on the genetic code. Counterpart RNA sequences can be generated by substitution of U for T. Those skilled in the art will readily recognize that, in view of the degeneracy of the genetic code, considerable sequence variation is possible among polynucleotide molecules encoding a given polypeptide. DNA and RNA encoding functional variants and fragments of such polypeptides can also be obtained using known recombinant methods to introduce variation into a polynucleotide sequence, followed by expression of the encoded polypeptide and determination of functional activity (e.g., binding to a cognate receptor or ligand) using an appropriate screening assay.

Methods for preparing DNA and RNA are well known in the art. For example, complementary DNA (cDNA) clones can be prepared from RNA that is isolated from a tissue or cell that produces large amounts of RNA encoding a polypeptide of interest. Total RNA can be prepared using guanidine HCl extraction followed by isolation by centrifugation in a CsCl gradient (Chirgwin et al., *Biochemistry* 18:52-94, 1979). Poly $(A)^+$ RNA is prepared from total RNA using the method of Aviv and Leder (*Proc. Natl. Acad. Sci. USA* 69:1408-1412, 1972). Complementary DNA is prepared from poly$(A)^+$ RNA using known methods. In the alternative, genomic DNA can be isolated. For some applications (e.g., expression in transgenic animals) it may be advantageous to use a genomic clone, or to modify a cDNA clone to include at least one genomic intron. Methods for identifying and isolating cDNA and genomic clones are well known and within the level of ordinary skill in the art, and include the use of the sequences disclosed herein, or parts thereof, for probing or priming a library. Polynucleotides encoding polypeptides of interest are identified and isolated by, for example, hybridization or polymerase chain reaction ("PCR," Mullis, U.S. Pat. No. 4,683,202). Expression libraries can be probed with antibodies to the polypeptide of interest, receptor fragments, or other specific binding partners.

The polynucleotides of the present invention can also be prepared by automated synthesis. The production of short, double-stranded segments (60 to 80 bp) is technically straightforward and can be accomplished by synthesizing the complementary strands and then annealing them. Longer segments (typically >300 bp) are assembled in modular form from single-stranded fragments that are from 20 to 100 nucleotides in length. Automated synthesis of polynucleotides is within the level of ordinary skill in the art, and suitable equipment and reagents are available from commercial suppliers. See generally Glick and Pasternak, *Molecular Biotechnology, Principles & Applications of Recombinant DNA*, ASM Press, Washington, D.C., 1994; Itakura et al., *Ann. Rev. Biochem.* 53:323-356, 1984; and Climie et al., *Proc. Natl. Acad. Sci. USA* 87:633-637, 1990.

In another aspect, materials and methods are provided for producing the polypeptide fusions of the present invention, including dimeric proteins comprising the polypeptide fusions. The polypeptide fusions can be produced in genetically engineered host cells according to conventional techniques. Suitable host cells are those cell types that can be transformed or transfected with exogenous DNA and grown in culture, and include bacteria, fungal cells, and cultured higher eukaryotic cells (including cultured cells of multicellular organisms), particularly cultured mammalian cells. Techniques for manipulating cloned DNA molecules and introducing exogenous DNA into a variety of host cells are disclosed by Sambrook et al., *Molecular Cloning: A Laboratory Manual,* 2nd ed., Cold Spring Harbor Laboratory Press, Cold Spring Harbor, N.Y., 1989, and Ausubel et al., eds., *Current Protocols in Molecular Biology*, Green and Wiley and Sons, NY, 1993.

In general, a DNA sequence encoding a polypeptide fusion is operably linked to other genetic elements required for its expression, generally including a transcription promoter and terminator, within an expression vector. The vector will also commonly contain one or more selectable markers and one or more origins of replication, although those skilled in the art will recognize that within certain systems selectable markers may be provided on separate vectors, and replication of the exogenous DNA may be provided by integration into the host cell genome. Selection of promoters, terminators, selectable markers, vectors and other elements is a matter of routine design within the level of ordinary skill in the art. Many such elements are described in the literature and are available through commercial suppliers.

To direct a polypeptide fusion into the secretory pathway of a host cell, a secretory signal sequence is provided in the expression vector. The secretory signal sequence may be that of the native non-immunoglobulin polypeptide, or may be derived from another secreted protein (e.g., t-PA; see U.S. Pat. No. 5,641,655) or synthesized de novo. An engineered cleavage site may be included at the junction between the secretory peptide and the remainder of the polypeptide fusion to optimize proteolytic processing in the host cell. The secretory signal sequence is operably linked to the DNA sequence encoding the polypeptide fusion, i.e., the two sequences are joined in the correct reading frame and positioned to direct the newly synthesized polypeptide fusion into the secretory pathway of the host cell. Secretory signal sequences are commonly positioned 5' to the DNA sequence encoding the polypeptide of interest, although certain signal sequences may be positioned elsewhere in the DNA sequence of interest (see, e.g., Welch et al., U.S. Pat. No. 5,037,743; Holland et al., U.S. Pat. No. 5,143,830). Secretory signal sequences suitable for use in accordance with the present invention include, for example, polynucleotides encoding amino acid residues 1-35 of SEQ ID NO:14 or amino acid residues 1-22 of SEQ ID NO:18.

Expression of polypeptide fusions via a host cell secretory pathway is expected to result in the production of dimeric proteins. Accordingly, in another aspect, the present invention provides dimeric proteins comprising first and second polypeptide fusions as described above (e.g., a dimeric protein comprising a first polypeptide fusion and a second polypeptide fusion, where each of the first and second polypeptide fusions comprises, from amino terminus to carboxyl terminus, P1-L1-D1-L2-P2, or where each of the first and second polypeptide fusions comprises, from amino terminus to carboxyl terminus, P2-L2-P1-L1-D, and where the dimeric protein is capable of specifically binding to the extracellular domain of CD155 (e.g., amino acid residues 28-343 of SEQ ID NO:22)). Dimers may also be assembled in vitro upon incubation of component polypeptides under suitable conditions. In general, in vitro assembly will include incubating the protein mixture under denaturing and reducing conditions followed by refolding and reoxidation of the polypeptides to form dimers. Recovery and assembly of proteins expressed in bacterial cells is disclosed below.

Cultured mammalian cells are suitable hosts for use within the present invention. Methods for introducing exogenous DNA into mammalian host cells include calcium phosphate-mediated transfection (Wigler et al., *Cell* 14:725, 1978; Corsaro and Pearson, *Somatic Cell Genetics* 7:603, 1981: Graham and Van der Eb, *Virology* 52:456, 1973), electroporation (Neumann et al., *EMBO J.* 1:841-845, 1982), DEAE-dextran mediated transfection (Ausubel et al., supra), and liposome-mediated transfection (Hawley-Nelson et al., *Focus* 15:73, 1993; Ciccarone et al., *Focus* 15:80, 1993). The production of recombinant polypeptides in cultured mammalian cells is disclosed by, for example, Levinson et al., U.S. Pat. No. 4,713,339; Hagen et al., U.S. Pat. No. 4,784,950; Palmiter et al., U.S. Pat. No. 4,579,821; and Ringold, U.S. Pat. No. 4,656,134. Suitable cultured mammalian cells include the COS-1 (ATCC No. CRL 1650), COS-7 (ATCC No. CRL 1651), BHK (ATCC No. CRL 1632), BHK 570 (ATCC No. CRL 10314), 293 (ATCC No. CRL 1573; Graham et al., *J. Gen. Virol.* 36:59-72, 1977) and Chinese hamster ovary (e.g., CHO-K1, ATCC No. CCL 61; CHO-DG44, Urlaub et al., *Proc. Natl. Acad. Sci. USA* 77:4216-4220, 1980) cell lines. Additional suitable cell lines are known in the art and available from public depositories such as the American Type Culture Collection, Manassas, Va. Strong transcription promoters can be used, such as promoters from SV-40, cytomegalovirus, or myeloproliferative sarcoma virus. See, e.g., U.S. Pat. No. 4,956,288 and U.S. Patent Application Publication No. 20030103986. Other suitable promoters include those from metallothionein genes (U.S. Pat. Nos. 4,579,821 and 4,601,978) and the adenovirus major late promoter. Expression vectors for use in mammalian cells include pZP-1, pZP-9, and pZMP21, which have been deposited with the American Type Culture Collection, University Blvd., Manassas, Va. USA under accession numbers 98669, 98668, and PTA-5266, respectively, and derivatives of these vectors.

Drug selection is generally used to select for cultured mammalian cells into which foreign DNA has been inserted. Such cells are commonly referred to as "transfectants." Cells that have been cultured in the presence of the selective agent and are able to pass the gene of interest to their progeny are referred to as "stable transfectants." An exemplary selectable marker is a gene encoding resistance to the antibiotic neomycin. Selection is carried out in the presence of a neomycin-type drug, such as G-418 or the like. Selection systems can also be used to increase the expression level of the gene of interest, a process referred to as "amplification." Amplification is carried out by culturing transfectants in the presence of a low level of the selective agent and then increasing the amount of selective agent to select for cells that produce high levels of the products of the introduced genes. An exemplary amplifiable selectable marker is dihydrofolate reductase, which confers resistance to methotrexate. Other drug resistance genes (e.g., hygromycin resistance, multi-drug resistance, puromycin acetyltransferase) can also be used. Cell-surface markers and other phenotypic selection markers can be used to facilitate identification of transfected cells (e.g., by fluorescence-activated cell sorting), and include, for example, CD8, CD4, nerve growth factor receptor, green fluorescent protein, and the like.

Other higher eukaryotic cells can also be used as hosts, including insect cells, plant cells and avian cells. The use of *Agrobacterium rhizogenes* as a vector for expressing genes in plant cells has been reviewed by Sinkar et al., *J. Biosci.* (Bangalore) 11:47-58, 1987. Transformation of insect cells and production of foreign polypeptides therein is disclosed by Guarino et al., U.S. Pat. No. 5,162,222 and WIPO publication WO 94/06463.

Insect cells can be infected with recombinant baculovirus, commonly derived from *Autographa californica* nuclear polyhedrosis virus (AcNPV). See King and Possee, *The Baculovirus Expression System: A Laboratory Guide*, Chapman & Hall, London; O'Reilly et al., *Baculovirus Expression Vectors: A Laboratory Manual*, Oxford University Press., New York, 1994; and Richardson, Ed., *Baculovirus Expression Protocols. Methods in Molecular Biology*, Humana Press, Totowa, N.J., 1995. Recombinant baculovirus can also be produced through the use of a transposon-based system described by Luckow et al. (*J. Virol.* 67:4566-4579, 1993). This system, which utilizes transfer vectors, is commercially available in kit form (BAC-TO-BAC kit; Life Technologies, Gaithersburg, Md.). The transfer vector (e.g., PFASTBAC1; Life Technologies) contains a Tn7 transposon to move the DNA encoding the protein of interest into a baculovirus genome maintained in *E. coli* as a large plasmid called a "bacmid." See Hill-Perkins and Possee, *J. Gen. Virol.* 71:971-976, 1990; Bonning et al., *J. Gen. Virol.* 75:1551-1556, 1994; and Chazenbalk and Rapoport, *J. Biol. Chem.* 270:1543-1549, 1995. Using techniques known in the art, a transfer vector encoding a polypeptide fusion is transformed into *E. coli* host cells, and the cells are screened for bacmids which contain an interrupted lacZ gene indicative of recombinant baculovirus. The bacmid DNA containing the recombinant baculovirus genome is isolated, using common techniques, and used to transfect *Spodoptera frugiperda* cells, such as Sf9 cells. Recombinant virus that expresses the polypeptide fusion is subsequently produced. Recombinant viral stocks are made by methods commonly used the art.

For protein production, the recombinant virus is used to infect host cells, typically a cell line derived from the fall armyworm, *Spodoptera frugiperda* (e.g., Sf9 or Sf21 cells) or *Trichoplusia ni* (e.g., HIGH FIVE cells; Invitrogen, Carlsbad, Calif.). See generally Glick and Pasternak, supra. See also U.S. Pat. No. 5,300,435. Serum-free media are used to grow and maintain the cells. Suitable media formulations are known in the art and can be obtained from commercial suppliers. The cells are grown up from an inoculation density of approximately $2-5\times10^5$ cells to a density of $1-2\times10^6$ cells, at which time a recombinant viral stock is added at a multiplicity of infection (MOI) of 0.1 to 10, more typically near 3. Procedures used are generally described in available laboratory manuals (e.g., King and Possee, supra; O'Reilly et al., supra.; Richardson, supra).

Fungal cells, including yeast cells, can also be used within the present invention. Yeast species of particular interest in this regard include *Saccharomyces cerevisiae, Pichia pastoris*, and *Pichia methanolica*. Methods for transforming *S. cerevisiae* cells with exogenous DNA and producing recombinant polypeptides therefrom are disclosed by, for example, Kawasaki, U.S. Pat. No. 4,599,311; Kawasaki et al., U.S. Pat. No. 4,931,373; Brake, U.S. Pat. No. 4,870,008; Welch et al., U.S. Pat. No. 5,037,743; and Murray et al., U.S. Pat. No. 4,845,075. Transformed cells are selected by phenotype determined by the selectable marker, commonly drug resistance or the ability to grow in the absence of a particular nutrient (e.g., leucine). An exemplary vector system for use in *Saccharomyces cerevisiae* is the POT1 vector system disclosed by Kawasaki et al. (U.S. Pat. No. 4,931,373), which allows transformed cells to be selected by growth in glucose-containing media. Suitable promoters and terminators for use in yeast include those from glycolytic enzyme genes (see, e.g., Kawasaki, U.S. Pat. No. 4,599,311; Kingsman et al., U.S. Pat. No. 4,615,974; and Bitter, U.S. Pat. No. 4,977,092) and alcohol dehydrogenase genes. See also U.S. Pat. Nos. 4,990,446; 5,063,154; 5,139,936; and 4,661,454. Transformation systems for other yeasts, including *Hansenula polymorpha, Schizosaccharomyces pombe, Kluyveromyces lactis, Kluyveromyces fragilis, Ustilago maydis, Pichia pastoris, Pichia methanolica, Pichia guillermondii*, and *Candida maltosa* are known in the art. See, e.g., Gleeson et al., *J. Gen. Microbiol.* 132:3459-3465, 1986; Cregg, U.S. Pat. No. 4,882,279; and Raymond et al., *Yeast* 14:11-23, 1998. *Aspergillus* cells may be utilized according to the methods of McKnight et al., U.S. Pat. No. 4,935,349. Methods for transforming *Acremonium chrysogenum* are disclosed by Sumino et al., U.S. Pat. No. 5,162,228. Methods for transforming *Neurospora* are disclosed by Lambowitz, U.S. Pat. No. 4,486,533. Production of recombinant proteins in *Pichia methanolica* is disclosed in U.S. Pat. Nos. 5,716,808; 5,736,383; 5,854,039; and 5,888,768.

Prokaryotic host cells, including strains of the bacteria *Escherichia coli, Bacillus* and other genera are also useful host cells within the present invention. Techniques for transforming these hosts and expressing foreign DNA sequences cloned therein are well known in the art (see, e.g., Sambrook et al., supra). When expressing a polypeptide fusion in bacteria such as *E. coli*, the polypeptide may be retained in the cytoplasm, typically as insoluble granules, or may be directed to the periplasmic space by a bacterial secretion sequence. In the former case, the cells are lysed, and the granules are recovered and denatured using, for example, guanidine HCl or urea. The denatured polypeptide can then be refolded and dimerized by diluting the denaturant, such as by dialysis against a solution of urea and a combination of reduced and oxidized glutathione, followed by dialysis against a buffered saline solution. In the alternative, the protein may be recovered from the cytoplasm in soluble form and isolated without the use of denaturants. The protein is recovered from the cell as an aqueous extract in, for example, phosphate buffered saline. To capture the protein of interest, the extract is applied directly to a chromatographic medium, such as an immobilized antibody or heparin-Sepharose column. Secreted polypeptides can be recovered from the periplasmic space in a soluble and functional form by disrupting the cells (by, for example, sonication or osmotic shock) and recovering the protein, thereby obviating the need for denaturation and refolding. See, e.g., Lu et al., *J. Immunol. Meth.* 267:213-226, 2002.

Transformed or transfected host cells are cultured according to conventional procedures in a culture medium containing nutrients and other components required for the growth of the chosen host cells. A variety of suitable media, including defined media and complex media, are known in the art and generally include a carbon source, a nitrogen source, essential amino acids, vitamins and minerals. Media may also contain such components as growth factors or serum, as required. The growth medium will generally select for cells containing the exogenously added DNA by, for example, drug selection or deficiency in an essential nutrient which is complemented by the selectable marker carried on the expression vector or co-transfected into the host cell.

Proteins of the present invention are purified by conventional protein purification methods, typically by a combination of chromatographic techniques. See generally *Affinity Chromatography: Principles & Methods*, Pharmacia LKB Biotechnology, Uppsala, Sweden, 1988; and Scopes, *Protein Purification: Principles and Practice*, Springer-Verlag, New York, 1994. Proteins comprising an immunoglobulin heavy chain polypeptide can be purified by affinity chromatography on immobilized protein A. Additional purification steps, such as gel filtration, can be used to obtain the desired level of purity or to provide for desalting, buffer exchange, and the like.

For example, fractionation and/or conventional purification methods can be used to obtain polypeptide fusions and dimeric proteins of the present invention purified from recombinant host cells. In general, ammonium sulfate precipitation and acid or chaotrope extraction may be used for fractionation of samples. Exemplary purification steps may include hydroxyapatite, size exclusion, FPLC and reverse-phase high performance liquid chromatography. Suitable chromatographic media include derivatized dextrans, agarose, cellulose, polyacrylamide, specialty silicas, and the like. PEI, DEAE, QAE and Q derivatives are suitable. Exemplary chromatographic media include those media derivatized with phenyl, butyl, or octyl groups, such as Phenyl-Sepharose FF (Pharmacia), Toyopearl butyl 650 (Toso Haas, Montgomeryville, Pa.), Octyl-Sepharose (Pharmacia) and the like; or polyacrylic resins, such as Amberchrom CG 71 (Toso Haas) and the like. Suitable solid supports include glass beads, silica-based resins, cellulosic resins, agarose beads, cross-linked agarose beads, polystyrene beads, cross-linked polyacrylamide resins and the like that are insoluble under the conditions in which they are to be used. These supports may be modified with reactive groups that allow attachment of proteins by amino groups, carboxyl groups, sulfhydryl groups, hydroxyl groups and/or carbohydrate moieties.

Examples of coupling chemistries include cyanogen bromide activation, N-hydroxysuccinimide activation, epoxide activation, sulfhydryl activation, hydrazide activation, and carboxyl and amino derivatives for carbodiimide coupling chemistries. These and other solid media are well known and widely used in the art, and are available from commercial suppliers. Selection of a particular method for polypeptide isolation and purification is a matter of routine design and is determined in part by the properties of the chosen support. See, e.g., *Affinity Chromatography: Principles & Methods* (Pharmacia LKB Biotechnology 1988); and Doonan, *Protein Purification Protocols* (The Humana Press 1996).

Additional variations in protein isolation and purification can be devised by those of skill in the art. For example, antibodies that specifically bind a polypeptide fusion or dimeric protein as described herein (e.g., an antibody that specifically binds a polypeptide segment corresponding to a cytokine or extracellular domain of a cell-surface receptor) can be used to isolate large quantities of protein by immunoaffinity purification.

The proteins of the present invention can also be isolated by exploitation of particular properties. For example, immobilized metal ion adsorption (IMAC) chromatography can be used to purify histidine-rich proteins, including those comprising polyhistidine tags. Briefly, a gel is first charged with divalent metal ions to form a chelate (Sulkowski, *Trends in Biochem.* 3:1, 1985). Histidine-rich proteins will be adsorbed to this matrix with differing affinities, depending upon the metal ion used, and will be eluted by competitive elution, lowering the pH, or use of strong chelating agents. Other methods of purification include purification of glycosylated proteins by lectin affinity chromatography and ion exchange chromatography (see, e.g., M. Deutscher, (ed.), *Meth. Enzymol.* 182:529, 1990). Within additional embodiments of the invention, a fusion of the polypeptide of interest and an affinity tag (e.g., maltose-binding protein, an immunoglobulin domain) may be constructed to facilitate purification. Moreover, receptor- or ligand-binding properties of a dimer protein can be exploited for purification. For example, a dimeric VSTM3 protein may be isolated by using affinity chromatography wherein CD155 is bound to a column and the dimeric VSTM3 protein is bound and subsequently eluted using standard chromatography methods.

The polypeptides of the present invention are typically purified to at least about 80% purity, more typically to at least about 90% purity and preferably to at least about 95%, at least about 96%, at least about 97%, at least about 98%, or at least about 99% purity with respect to contaminating macromolecules, particularly other proteins and nucleic acids, and free of infectious and pyrogenic agents. The polypeptides of the present invention may also be purified to a pharmaceutically pure state, which is greater than 99.9% pure. In certain preparations, purified polypeptide is substantially free of other polypeptides, particularly other polypeptides of animal origin.

IV. Methods of Use and Pharmaceutical Compositions

The dimeric proteins of the present invention can be used for diagnosis, therapy, or research to provide one or more activities associated with the P1 and P2 polypeptides. Such activities include, without limitation, receptor binding, receptor activation, and ligand binding. Those skilled in the art will readily envision a range of uses for the proteins. Therapeutic uses include, for example, use as cytokine antagonists, such as for the treatment of cancers or immunological disorders, and as growth factor agonists, such as to promote tissue growth or healing or to promote development of vasculature or other tissue. Diagnostic uses include, for example, use as targeting agents for radioisotopes or other labels, for detecting the presence of molecules on cell surfaces or in biological fluids or extracts, or as controls in in vitro assays. Within research the proteins of the present invention can be used, for example, for labeling cells, assaying for the presence of cell-surface receptors or soluble molecules, and to study the biology of cytokiner or receptor polypeptides or their binding partners.

In a particular aspect, the present invention provides methods of treating a T-cell-mediated immune disorder. The methods generally include administering to a subject having a T-cell-mediated immune disorder an effective amount of a dimeric VSTM3 (B7R1) protein as described herein. T-cell-mediated immune disorders amenable to treatment in accordance with the present invention include, for example, autoimmune diseases, graft-versus-host disease (GVHD), and transplant rejection. Examples of T-cell mediated autoimmune diseases include rheumatoid arthritis, multiple sclerosis (MS) (e.g., spino-optical MS, primary progressive MS (PPMS), and relapsing remitting MS (RRMS)), insulin dependent diabetes mellitus (IDDM), systemic lupus erythematosus (SLE), coeliac disease, neuritis, polymyositis, psoriasis, psoriatic arthritis, vitiligo, Sjogren's syndrome, autoimmune pancreatitis, inflammatory bowel diseases (e.g., Crohn's disease, ulcerative colitis), active chronic hepatitis, glomerulonephritis, scleroderma, sarcoidosis, autoimmune thyroid diseases, Hashimoto's thyroiditis, Graves disease, Wegener's granulomatosis, myasthenia gravis, asthma, Addison's disease, autoimmune uveoretinitis, pemphigus vulgaris, primary biliary cirrhosis, pernicious anemia, sympathetic opthalmia, uveitis, autoimmune hemolytic anemia, pulmonary fibrosis, chronic beryllium disease, and idiopathic pulmonary fibrosis, to name a few.

For therapeutic use, a dimeric protein as described herein is delivered in a manner consistent with conventional methodologies associated with management of the disease or disorder for which treatment is sought. In accordance with the disclosure herein, an effective amount of the dimeric protein is administered to a subject in need of such treatment for a time and under conditions sufficient to prevent or treat the disease or disorder.

Subjects for administration of dimeric proteins as described herein include patients at high risk for developing a particular disease or disorder as well as patients presenting with an existing disease or disorder. In certain embodiments, the subject has been diagnosed as having the disease or disorder for which treatment is sought. Further, subjects can be monitored during the course of treatment for any change in the disease or disorder (e.g., for an increase or decrease in clinical symptoms of the disease or disorder). Also, in some variations, the subject does not suffer from another disease or disorder requiring treatment that involves administration of a cytokine or receptor polypeptide corresponding to the P1 or P2 polypeptide segment of the dimeric protein.

In prophylactic applications, pharmaceutical compositions or medicants are administered to a patient susceptible to, or otherwise at risk of, a particular disease in an amount sufficient to eliminate or reduce the risk or delay the outset of the disease. In therapeutic applications, compositions or medicants are administered to a patient suspected of, or already suffering from such a disease in an amount sufficient to cure, or at least partially arrest, the symptoms of the disease and its complications. An amount adequate to accomplish this is referred to as a therapeutically- or pharmaceutically-effective dose or amount. In both prophylactic and therapeutic regimes, agents are usually administered in several dosages until a sufficient response (e.g., inhibition of inappropriate T cell responses) has been achieved. Typically, the response is monitored and repeated dosages are given if the desired response starts to fade.

To identify subject patients for treatment according to the methods of the invention, accepted screening methods may be employed to determine risk factors associated with a specific disease or to determine the status of an existing disease identified in a subject. Such methods can include, for example, determining whether an individual has relatives who have been diagnosed with a particular disease. Screening methods can also include, for example, conventional work-ups to determine familial status for a particular disease known to have a heritable component. Toward this end, nucleotide probes can be routinely employed to identify individuals carrying genetic markers associated with a particular disease of interest. In addition, a wide variety of immunological methods are known in the art that are useful to identify markers for specific diseases. Screening may be implemented as indicated by known patient symptomology, age factors, related risk factors, etc. These methods allow the clinician to routinely select patients in need of the methods described herein for treatment. In accordance with these methods, treatment using a dimeric protein of the present invention (e.g., treatment using a dimeric VSTM3 protein to inhibit inappropriate T-cell responses) may be implemented as an independent treatment program or as a follow-up, adjunct, or coordinate treatment regimen to other treatments.

For administration, a dimeric protein in accordance with the present invention is formulated as a pharmaceutical composition. A pharmaceutical composition comprising a dimeric protein can be formulated according to known methods to prepare pharmaceutically useful compositions, whereby the therapeutic molecule is combined in a mixture with a pharmaceutically acceptable carrier. A composition is said to be a "pharmaceutically acceptable carrier" if its administration can be tolerated by a recipient patient. Sterile phosphate-buffered saline is one example of a pharmaceutically acceptable carrier. Other suitable carriers are well-known to those in the art. (See, e.g., Gennaro (ed.), *Remington's Pharmaceutical Sciences* (Mack Publishing Company, 19th ed. 1995).) Formulations may further include one or more excipients, preservatives, solubilizers, buffering agents, albumin to prevent protein loss on vial surfaces, etc.

A pharmaceutical composition comprising a dimeric protein of the present invention is administered to a subject in an effective amount. The dimeric protein may be administered to subjects by a variety of administration modes, including, for example, by intramuscular, subcutaneous, intravenous, intra-atrial, intra-articular, parenteral, intranasal, intrapulmonary, transdermal, intrapleural, intrathecal, and oral routes of administration. For prevention and treatment purposes, the dimeric protein may be administered to a subject in a single bolus delivery, via continuous delivery (e.g., continuous transdermal delivery) over an extended time period, or in a repeated administration protocol (e.g., on an hourly, daily, or weekly basis).

Determination of effective dosages in this context is typically based on animal model studies followed up by human clinical trials and is guided by determining effective dosages and administration protocols that significantly reduce the occurrence or severity of the subject disease or disorder in model subjects. Effective doses of the compositions of the present invention vary depending upon many different factors, including means of administration, target site, physiological state of the patient, whether the patient is human or an animal, other medications administered, whether treatment is prophylactic or therapeutic, as well as the specific activity of the composition itself and its ability to elicit the desired response in the individual. Usually, the patient is a human, but in some diseases, the patient can be a nonhuman mammal. Typically, dosage regimens are adjusted to provide an optimum therapeutic response, i.e., to optimize safety and efficacy. Accordingly, a therapeutically or prophylactically effective amount is also one in which any undesired collateral effects are outweighed by beneficial effects (e.g., in the case of a dimeric VSTM3 protein, where any undesired collateral effects are outweighted by beneficial effects of inhibiting T-cell-mediated immune responses with the dimeric VSTM3 protein). For administration of a dimeric protein of the invention, such as, for example, a dimeric VSTM3 protein, a dosage typically ranges from about 0.1 g to 100 mg/kg or 1 g/kg to about 50 mg/kg, and more usually 10 g to 5 mg/kg of the subject's body weight. In more specific embodiments, an effective amount of the agent is between about 1 g/kg and about 20 mg/kg, between about 10 g/kg and about 10 mg/kg, or between about 0.1 mg/kg and about 5 mg/kg. Dosages within this range can be achieved by single or multiple administrations, including, e.g., multiple administrations per day or daily, weekly, bi-weekly, or monthly administrations. For example, in certain variations, a regimen consists of an initial administration followed by multiple, subsequent administrations at weekly or bi-weekly intervals. Another regimen consists of an initial administration followed by multiple, subsequent administrations at monthly or bi-monthly intervals. Alternatively, administrations can be on an irregular basis as indicated by monitoring of clinical symptoms of the disease or disorder and/or monitoring of disease biomarkers or other disease correlates (e.g., T cell activity in the case of a T-cell-mediated immune disorder).

Dosage of the pharmaceutical composition may be varied by the attending clinician to maintain a desired concentration at a target site. For example, if an intravenous mode of delivery is selected, local concentration of the agent in the bloodstream at the target tissue may be between about 1-50 nanomoles of the composition per liter, sometimes between about 1.0 nanomole per liter and 10, 15, or 25 nanomoles per liter depending on the subject's status and projected measured response. Higher or lower concentrations may be selected based on the mode of delivery, e.g., trans-epidermal delivery versus delivery to a mucosal surface. Dosage should also be adjusted based on the release rate of the administered formulation, e.g., nasal spray versus powder, sustained release oral or injected particles, transdermal formulations, etc. To achieve the same serum concentration level, for example, slow-release particles with a release rate of 5 nanomolar (under standard conditions) would be administered at about twice the dosage of particles with a release rate of 10 nanomolar.

A pharmaceutical composition comprising a dimeric protein as described herein (e.g., a dimeric VSTM3 protein) can be furnished in liquid form, in an aerosol, or in solid form. Liquid forms, are illustrated by injectable solutions, aerosols, droplets, topological solutions and oral suspensions. Exemplary solid forms include capsules, tablets, and controlled-release forms. The latter form is illustrated by miniosmotic pumps and implants. (See, e.g., Bremer et al., *Pharm. Biotechnol.* 10:239, 1997; Ranade, "Implants in Drug Delivery," in *Drug Delivery Systems* 95-123 (Ranade and Hollinger, eds., CRC Press 1995); Bremer et al., "Protein Delivery with Infusion Pumps," in *Protein Delivery: Physical Systems* 239-254 (Sanders and Hendren, eds., Plenum Press 1997); Yewey et al., "Delivery of Proteins from a Controlled Release Injectable Implant," in *Protein Delivery: Physical Systems* 93-117

(Sanders and Hendren, eds., Plenum Press 1997).) Other solid forms include creams, pastes, other topological applications, and the like.

Liposomes provide one means to deliver therapeutic polypeptides to a subject, e.g., intravenously, intraperitoneally, intrathecally, intramuscularly, subcutaneously, or via oral administration, inhalation, or intranasal administration. Liposomes are microscopic vesicles that consist of one or more lipid bilayers surrounding aqueous compartments. (See, generally, Bakker-Woudenberg et al., *Eur. J. Clin. Microbiol. Infect. Dis.* 12 (*Suppl.* 1):561, 1993; Kim, Drugs 46:618, 1993; Ranade, "Site-Specific Drug Delivery Using Liposomes as Carriers," in *Drug Delivery Systems* 3-24 (Ranade and Hollinger, eds., CRC Press 1995).) Liposomes are similar in composition to cellular membranes and as a result, liposomes can be administered safely and are biodegradable. Depending on the method of preparation, liposomes may be unilamellar or multilamellar, and liposomes can vary in size with diameters ranging from 0.02 μm to greater than 10 μm. A variety of agents can be encapsulated in liposomes: hydrophobic agents partition in the bilayers and hydrophilic agents partition within the inner aqueous space(s). (See, e.g., Machy et al., *Liposomes In Cell Biology And Pharmacology* (John Libbey 1987); Ostro et al., *American J. Hosp. Pharm.* 46:1576, 1989.) Moreover, it is possible to control the therapeutic availability of the encapsulated agent by varying liposome size, the number of bilayers, lipid composition, as well as the charge and surface characteristics of the liposomes.

Liposomes can adsorb to virtually any type of cell and then slowly release the encapsulated agent. Alternatively, an absorbed liposome may be endocytosed by cells that are phagocytic. Endocytosis is followed by intralysosomal degradation of liposomal lipids and release of the encapsulated agents (see Scherphof et al., *Ann. N.Y. Acad. Sci.* 446:368, 1985). After intravenous administration, small liposomes (0.1 to 1.0 μm) are typically taken up by cells of the reticuloendothelial system, located principally in the liver and spleen, whereas liposomes larger than 3.0 μm are deposited in the lung. This preferential uptake of smaller liposomes by the cells of the reticuloendothelial system has been used to deliver chemotherapeutic agents to macrophages and to tumors of the liver.

The reticuloendothelial system can be circumvented by several methods including saturation with large doses of liposome particles, or selective macrophage inactivation by pharmacological means (see Claassen et al., *Biochim. Biophys. Acta* 802:428, 1984). In addition, incorporation of glycolipid- or polyethelene glycol-derivatized phospholipids into liposome membranes has been shown to result in a significantly reduced uptake by the reticuloendothelial system (see Allen et al., *Biochim. Biophys. Acta* 1068:133, 1991; Allen et al., *Biochim. Biophys. Acta* 1150:9, 1993).

Liposomes can also be prepared to target particular cells or organs by varying phospholipid composition or by inserting receptors or counter-receptors into the liposomes. For example, liposomes, prepared with a high content of a nonionic surfactant, have been used to target the liver. (See, e.g., Japanese Patent 04-244,018 to Hayakawa et al.; Kato et al., *Biol. Pharm. Bull.* 16:960, 1993.) These formulations were prepared by mixing soybean phospatidylcholine, α-tocopherol, and ethoxylated hydrogenated castor oil (HCO-60) in methanol, concentrating the mixture under vacuum, and then reconstituting the mixture with water. A liposomal formulation of dipalmitoylphosphatidylcholine (DPPC) with a soybean-derived sterylglucoside mixture (SG) and cholesterol (Ch) has also been shown to target the liver. (See Shimizu et al., *Biol. Pharm. Bull.* 20:881, 1997.)

Alternatively, various targeting counter-receptors can be bound to the surface of the liposome, such as antibodies, antibody fragments, carbohydrates, vitamins, and transport proteins. For example, for targeting to the liver, liposomes can be modified with branched type galactosyllipid derivatives to target asialoglycoprotein (galactose) receptors, which are exclusively expressed on the surface of liver cells. (See Kato and Sugiyama, *Crit. Rev. Ther. Drug Carrier Syst.* 14:287, 1997; Murahashi et al., *Biol. Pharm. Bull.* 20:259, 1997.) In a more general approach to tissue targeting, target cells are prelabeled with biotinylated antibodies specific for a counter-receptor expressed by the target cell. (See Harasym et al., *Adv. Drug Deliv. Rev.* 32:99, 1998.) After plasma elimination of free antibody, streptavidin-conjugated liposomes are administered. In another approach, targeting antibodies are directly attached to liposomes. (See Harasym et al., supra.)

Polypeptides can be encapsulated within liposomes using standard techniques of protein microencapsulation. (See, e.g., Anderson et al., *Infect. Immun.* 31:1099, 1981; Anderson et al., *Cancer Res.* 50:1853, 1990; Cohen et al., *Biochim. Biophys. Acta* 1063:95, 1991; Alving et al. "Preparation and Use of Liposomes in Immunological Studies," in *Liposome Technology* (Vol. III) 317 (Gregoriadis, ed., CRC Press, 2nd ed. 1993); Wassef et al., *Meth. Enzymol.* 149:124, 1987.) As noted above, therapeutically useful liposomes may contain a variety of components. For example, liposomes may comprise lipid derivatives of poly(ethylene glycol). (See Allen et al., *Biochim. Biophys. Acta* 1150:9, 1993.)

Degradable polymer micro spheres have been designed to maintain high systemic levels of therapeutic proteins. Micro spheres are prepared from degradable polymers such as poly (lactide-co-glycolide) (PLG), polyanhydrides, poly (ortho esters), nonbiodegradable ethylvinyl acetate polymers, in which proteins are entrapped in the polymer. (See, e.g., Gombotz and Pettit, *Bioconjugate Chem.* 6:332, 1995; Ranade, "Role of Polymers in Drug Delivery," in *Drug Delivery Systems* 51-93 (Ranade and Hollinger, eds., CRC Press 1995); Roskos and Maskiewicz, "Degradable Controlled Release Systems Useful for Protein Delivery," in *Protein Delivery: Physical Systems* 45-92 (Sanders and Hendren, eds., Plenum Press 1997); Bartus et al., *Science* 281:1161, 1998; Putney and Burke, *Nature Biotechnology* 16:153, 1998; Putney, *Curr. Opin. Chem. Biol.* 2:548, 1998.) Polyethylene glycol (PEG)-coated nanospheres can also provide carriers for intravenous administration of therapeutic proteins. (See, e.g., Gref et al., *Pharm. Biotechnol.* 10:167, 1997.)

Other dosage forms can be devised by those skilled in the art, as shown by, e.g., Ansel and Popovich, *Pharmaceutical Dosage Forms and Drug Delivery Systems* (Lea & Febiger, 5th ed. 1990); Gennaro (ed.), *Remington's Pharmaceutical Sciences* (Mack Publishing Company, 19th ed. 1995), and Ranade and Hollinger, *Drug Delivery Systems* (CRC Press 1996).

Dimeric proteins as described herein, including, e.g., dimeric VSTM3 (B7R1) proteins, can be used in the context of gene therapy. Gene therapy can be broadly defined as the transfer of genetic material into a cell to transiently or permanently alter the cellular phenotype. Numerous methods are being developed for delivery of cytokines, tumor antigens, and additional co-stimulatory molecules via gene therapy to specific locations within tumor patients (see generally Rosenberg (ed.), *Principles and practice of the biologic therapy of cancer* (Lippincott Williams & Wilkins, Philadelphia, Pa., 3rd ed. 2000)). These methodologies can be adapted to use DNA or RNA encoding polypeptide fusions of the present invention.

Accordingly, in some embodiments, a disease or disorder in a subject is treated by administration of a nucleic acid encoding a polypeptide fusion as described herein. For example, in certain embodiments, T-cell-mediated responses in a subject are inhibited by administration of a nucleic acid encoding a VSTM3 (B7R1) polypeptide fusion as described herein; using such VSTM3-encoding nucleic acids, T-cell-mediated immune disorders can be treated as generally discussed above. In the case of nucleic acid therapy, a polypeptide fusion as described herein is expressed and is secreted from cells to form a dimeric protein, which exerts a therapeutic effect in a manner similar to a dimeric protein of the present invention that is directly administered to a subject as described above (e.g., in the case of a VSTM3-encoding nucleic acid, a VSTM3 polypeptide fusion as described herein is expressed and secreted to form a dimeric VSTM3 protein, which inhibits T-cell-mediated effects in a manner similar to a dimeric VSTM3 protein that is directly administered to a subject). Alternatively, a polypeptide fusion of the present invention may be expressed in a form that maintains association with the surface of the cell in which the protein is expressed (e.g., with a functional transmembrane domain or a GPI linkage); such embodiments are particularly useful for facilitating targeting to particular cells or tissues to maintain localized therapeutic effects (such as, for example, localized inhibition of T-cell-mediated responses via expression of a dimeric VSTM3 protein).

Polypeptide-encoding nucleic acids for use in therapeutic methods can be DNA or RNA. A nucleic acid segment encoding a polypeptide fusion as described herein is typically linked to regulatory elements, such as a promoter and enhancer, that allow expression of the DNA segment in the intended target cells of a patient. For example, for expression in blood cells, as is desirable for inhibition of T-cell-mediated responses via expression of VSTM3 polypeptides, promoter and enhancer elements from light or heavy chain immunoglobulin genes or the CMV major intermediate early promoter and enhancer are suitable to direct expression. The linked regulatory elements and coding sequences are often cloned into a vector.

A number of viral vector systems are available including retroviral systems (see, e.g., Lawrie and Tumin, Cur. Opin. Genet. Develop. 3, 102-109, 1993); adenoviral vectors (see, e.g., Bett et al., J. Virol. 67, 5911, 1993); adeno-associated virus vectors (see, e.g., Zhou et al., J. Exp. Med. 179, 1867, 1994), viral vectors from the pox family including vaccinia virus and the avian pox viruses, viral vectors from the alpha virus genus such as those derived from Sindbis and Semliki Forest Viruses (see, e.g., Dubensky et al., J. Virol. 70, 508-519, 1996), and papillomaviruses (Ohe et al., Human Gene Therapy 6, 325-333, 1995; WO 94/12629 (Woo et al.); Xiao & Brandsma, Nucleic Acids. Res. 24, 2630-2622, 1996).

DNA encoding a polypeptide fusion of the present invention, or a vector containing the same, can be packaged into liposomes. Suitable lipids and related analogs are described by U.S. Pat. Nos. 5,208,036, 5,264,618, 5,279,833 and 5,283,185. Vectors and DNA encoding the polypeptide fusion can also be adsorbed to or associated with particulate carriers, examples of which include polymethyl methacrylate polymers and polylactides and poly(lactide-co-glycolides) (see, e.g., McGee et al., *J. Micro Encap.,* 1996).

Gene therapy vectors or naked DNA can be delivered in vivo by administration to an individual patient, typically by systemic administration (e.g., intravenous, intraperitoneal, nasal, gastric, intradermal, intramuscular, subdermal, or intracranial infusion) or topical application (see e.g., U.S. Pat. No. 5,399,346). DNA can also be administered using a gene gun. (See Xiao & Brandsma, supra.) The DNA encoding a polypeptide is precipitated onto the surface of microscopic metal beads. The microprojectiles are accelerated with a shock wave or expanding helium gas, and penetrate tissues to a depth of several cell layers. For example, The Accel™ Gene Delivery Device manufactured by Agacetus, Inc. Middleton Wis. is suitable. Alternatively, naked DNA can pass through skin into the blood stream simply by spotting the DNA onto skin with chemical or mechanical irritation (see, e.g., WO 95/05853).

Pharmaceutical compositions as described herein may also be used in the context of combination therapy. The term "combination therapy" is used herein to denote that a subject is administered at least one therapeutically effective dose of a dimeric protein as described herein and another therapeutic agent.

Pharmaceutical compositions may be supplied as a kit comprising a container that comprises a polypeptide fusion, dimeric protein, or polynucleotide as described herein. A therapeutic molecule can be provided, for example, in the form of an injectable solution for single or multiple doses, or as a sterile powder that will be reconstituted before injection. Alternatively, such a kit can include a dry-powder disperser, liquid aerosol generator, or nebulizer for administration of a therapeutic protein or polynucleotide. Such a kit may further comprise written information on indications and usage of the pharmaceutical composition. For example, in particular embodiments of a kit comprising a VSTM3 (B7R1) composition, such information may include a statement that the VSTM3 composition is contraindicated in patients with known hypersensitivity to VSTM3.

The invention is further illustrated by the following non-limiting examples.

Example 1

Construction and Expression of Murine B7R1Barbell (mB7R1-Barbell)

An expression plasmid containing mB7R1-mFc2-mB7R1 (mB7R1-Barbell with the native mB7R1 leader sequence; polynucleotide sequence shown in SEQ ID NO:9; encoded polypeptide sequence shown in SEQ ID NO:10) was constructed via homologous recombination using a two step process.

Step 1

First, a DNA fragment containing the sequence for the fusion protein mB7R1-mFc2 (mouse B7R1 extracellular domain (ECD) fused to a mouse Fc fragment (mFc2)) was generated by PCR amplification using a previously generated clone as template. The mB7R1-mFc2 fragment had sequence overlap into pZMP42 and was generated using primers zc60639 (SEQ ID NO:36), zc60643 (SEQ ID NO:37), and zc60645 (SEQ ID NO:38). This fragment was created with the following PCR conditions: 1 cycle, 94° C., 5 minutes; 35 cycles, 94° C., 1 minute, followed by 58° C., 2 minutes, followed by 72° C., 3 minutes; 1 cycle, 72° C., 10 minutes.

The PCR reaction mixture was run on a 1% agarose gel and a band corresponding to the sizes of the inserts were gel-extracted using a QIAQUICK™ Gel Extraction Kit (Qiagen, Cat. No. 28704).

Plasmid pZMP42 is a mammalian expression vector containing an expression cassette having the MPSV promoter, multiple restriction sites for insertion of coding sequences, and an otPA signal peptide sequence; an internal ribosome entry site (IRES) element from Hepatitis C virus, and the extracellular domain of CD8 truncated at the C-terminal end of the transmembrane domain; an internal ribosome entry site (IRES) element from poliovirus, a DHFR gene, and the SV40 terminator; an *E. coli* origin of replication; and URA3 and CEN-ARS sequences required for selection and replication in *S. cerevisiae*. It was constructed from pZMP21 (US Patent Application Publication No. US 2003/0232414 A1) (deposited at the American Type Culture Collection, 10801 University Boulevard, Manassas, Va. 20110-2209, designated as ATCC# PTA-5266).

The plasmid pZMP42 was cut with BglII prior to recombination in yeast with the PCR fragment. One hundred microliters of competent yeast (*S. cerevisiae*) cells were independently combined with 10 μl of the insert DNA and 100 ng of cut pZMP42 vector, and the mix was transferred to a 0.2-cm electroporation cuvette. The yeast/DNA mixture was electropulsed using power supply (BioRad Laboratories, Hercules, Calif.) settings of 0.75 kV (5 kV/cm), ∞ ohms, and 25 μF. Six hundred μl of 1.2 M sorbitol was added to the cuvette, and the yeast was plated in a 100-μl and 300 μl aliquot onto two URA-D plates and incubated at 30° C. After about 72 hours, the Ura+ yeast transformants from a single plate were resuspended in 1 ml H2O and spun briefly to pellet the yeast cells. The cell pellet was resuspended by vortex in 0.1 ml of lysis buffer (2% Triton X-100, 1% SDS, 100 mM NaCl, 10 mM Tris, pH 8.0, 1 mM EDTA), and 0.1 mL of P1 (from QIAPREP® Spin Miniprep Kit, Qiagen, cat#27106) with 10 units of Zymolyase added (Zymo Research, cat# E1002). The yeast suspension was incubated for 10 minutes in a 37° C. waterbath. DNA from the yeast was isolated using the standard QIAPREP® Spin Miniprep Kit protocol (Qiagen, cat#27106), starting at the step of adding reagent P2.

Transformation of electrocompetent *E. coli* host cells (DH12S) was done using 5 μl of the yeast DNA prep and 50 μl of cells. The cells were electropulsed at 2.0 kV, 25 μF, and 400 ohms. Following electroporation, 1 ml SOC (2% BACTO™ Tryptone (Difco, Detroit, Mich.), 0.5% yeast extract (Difco), 10 mM NaCl, 2.5 mM KCl, 10 mM $MgCl_2$, 10 mM $MgSO_4$, 20 mM glucose) was added and then the cells were plated in a 50 μl and a 200 μl aliquot on two LB AMP plates (LB broth (Lennox), 1.8% BACTO™ Agar (Difco), 100 mg/L Ampicillin).

The inserts of several clones for the construct were subjected to sequence analysis and one clone, containing the correct sequence, was selected. Larger scale plasmid DNA was isolated using a commercially available kit (QIAGEN Plasmid Mega Kit, Qiagen, Valencia, Calif.) according to manufacturer's instructions.

The construct was used as the base for the second step of construction.

Step 2

The second step of construction involves the generation of a mB7R1ECD fragment using a previously generated clone as a template. The mB7R1ECD fragment had a BspEI restriction cleavage site added to the 5' end of the fragment and a Bsu36I site added to the 3' end of the fragment, and was generated using primers zc60642 (SEQ ID NO:39) and zc60641 (SEQ ID NO:40). The fragment was created using the following PCR conditions: 1 cycle, 94° C., 5 minutes; 35 cycles, 94° C., 1 minute, followed by 58° C., 2 minutes, followed by 72° C., 3 minutes; 1 cycle, 72° C., 10 minutes.

The PCR reaction mixtures were run on a 1% agarose gel and a band corresponding to the sizes of the inserts were gel-extracted using a QIAQUICK™ Gel Extraction Kit (Qiagen, Cat. No. 28704).

Both the construct from the first step and the second step mB7R1ECD fragment were digested using BspEI and Bsu36I. The digested DNA for the first step construct and the second step mB7R1ECD fragment were run on a 1% agarose gel and a band corresponding to the sizes of the DNA were gel-extracted using a QIAQUICK™ Gel Extraction Kit (Qiagen, Cat. No. 28704). The two purified DNA preparations were then ligated together using methods known in the art.

Transformation of electrocompetent *E. coli* host cells (DH12S) was done using 1 μl of the ligation prep and 50 μl of cells. The cells were electropulsed at 2.0 kV, 25 μF, and 400 ohms. Following electroporation, 1 ml SOC (2% BACTO™ Tryptone (Difco, Detroit, Mich.), 0.5% yeast extract (Difco), 10 mM NaCl, 2.5 mM KCl, 10 mM $MgCl_2$, 10 mM $MgSO_4$, 20 mM glucose) was added and then the cells were plated in a 50 μl and a 200 μl aliquot on two LB AMP plates (LB broth (Lennox), 1.8% BACTO™ Agar (Difco), 100 mg/L Ampicillin).

The inserts of several clones for the construct were subjected to sequence analysis and one clone, containing the correct sequence, was selected. Larger scale plasmid DNA was isolated using a commercially available kit (QIAGEN Plasmid Mega Kit, Qiagen, Valencia, Calif.) according to manufacturer's instructions. This clone was designated #1863.

The full-length nucleotide coding sequence and corresponding amino acid sequence for mB7R1-Barbell, with the native signal sequence, are shown in SEQ ID NOs:9 and 10, respectively. The mature form of mB7R1-Barbell corresponds to amino acids 26-489 of SEQ ID NO:10 (encoded by nucleotides 76-1467 of SEQ ID NO:9).

Expression of mB7R1-Barbell

Three sets of 200 μg of the construct #1863 were each digested with 200 units of Pvu I at 37° C. for three hours and then were precipitated with IPA and spun down in a 1.5 mL microfuge tube. The supernatant was decanted off the pellet, and the pellet was washed with 1 mL of 70% ethanol and allowed to incubate for 5 minutes at room temperature. The tube was spun in a microfuge for 10 minutes at 14,000 RPM and the supernatant was decanted off the pellet. The pellet was then resuspended in 750 μl of ZF1 media in a sterile environment, allowed to incubate at 60° C. for 10 minutes, and was allowed to cool to room temperature. 5×106 CHO DXB11 5×SA cells were spun down in each of three tubes and were resuspended using the DNA-media solution. The DNA/cell mixtures were placed in a 0.4 cm gap cuvette and electroporated using the following parameters: 950 μF, high capacitance, and 300 V. The contents of the cuvettes were then removed, pooled, and diluted to 25 mLs with ZF1 media and placed in a 125 mL shake flask. The flask was placed in an incubator on a shaker at 37° C., 6% $CO_2$, and shaking at 120 RPM.

The cell line was subjected to nutrient selection followed by step amplification to 200 nM methotrexate (MTX). Expression was confirmed by western blot, and the cell line was scaled-up and protein purification followed.

Example 2

Construction and Expression of Human B7R1Barbell (B7R1-Barbell)

An expression plasmid containing B7R1-Fc5-B7R1 (B7R1-Barbell with the native B7R1 leader sequence; polynucleotide sequence shown in SEQ ID NO:5; encoded polypeptide sequence shown in SEQ ID NO:6) was constructed via homologous recombination using a two step process.

Step 1

First, a DNA fragment containing the sequence for the fusion protein B7R1-Fc5 (human B7R1 extracellular domain (ECD) fused to effector function minus Fc fragment Fc5) was generated by PCR amplification and recombination. The B7R1ECD fragment and Fc5 fragment were made using previously generated clones as templates. The B7R1ECD fragment had sequence overlap into Fc5 and was generated using primers zc53051 (SEQ ID NO:41) and zc60385 (SEQ ID NO:42). The fragment encoding Fc5 had a 5' overlap into B7R1ECD, a GGGSG linker, a multiple cloning region containing a BspEI site and a downstream BglII site, and sequence overlap with the pZMP42 vector sequence, and was generated using primers zc60386 (SEQ ID NO:43), zc59433 (SEQ ID NO:44), and zc59434 (SEQ ID NO:45). These two fragments were created with the following PCR conditions: 1 cycle, 94° C., 5 minutes; 35 cycles, 94° C., 1 minute, followed by 58° C., 2 minutes, followed by 72° C., 3 minutes; 1 cycle, 72° C., 10 minutes.

The PCR reaction mixtures were run on a 1% agarose gel and a band corresponding to the sizes of the inserts were gel-extracted using a QIAQUICK™ Gel Extraction Kit (Qiagen, Cat. No. 28704).

Plasmid pZMP42 is a mammalian expression vector containing an expression cassette having the MPSV promoter, multiple restriction sites for insertion of coding sequences, and an otPA signal peptide sequence; an internal ribosome entry site (IRES) element from Hepatitis C virus, and the extracellular domain of CD8 truncated at the C-terminal end of the transmembrane domain; an internal ribosome entry site (IRES) element from poliovirus, a DHFR gene, and the SV40 terminator; an *E. coli* origin of replication; and URA3 and CEN-ARS sequences required for selection and replication in *S. cerevisiae*. It was constructed from pZMP21 (US Patent Application Publication No. US 2003/0232414 A1) (deposited at the American Type Culture Collection, 10801 University Boulevard, Manassas, Va. 20110-2209, designated as ATCC# PTA-5266).

The plasmid pZMP42 was cut with BglII prior to recombination in yeast with the PCR fragment. One hundred microliters of competent yeast (*S. cerevisiae*) cells were independently combined with 10 µl of the insert DNA and 100 ng of cut pZMP42 vector, and the mix was transferred to a 0.2-cm electroporation cuvette. The yeast/DNA mixture was electropulsed using power supply (BioRad Laboratories, Hercules, Calif.) settings of 0.75 kV (5 kV/cm), ∞ ohms, and 25 µF. Six hundred µl of 1.2 M sorbitol was added to the cuvette, and the yeast was plated in a 100-µl and 300 µl aliquot onto two URA-D plates and incubated at 30° C. After about 72 hours, the Ura+ yeast transformants from a single plate were resuspended in 1 ml H2O and spun briefly to pellet the yeast cells. The cell pellet was resuspended by vortex in 0.1 ml of lysis buffer (2% Triton X-100, 1% SDS, 100 mM NaCl, 10 mM Tris, pH 8.0, 1 mM EDTA), and 0.1 mL of P1 (from QIAPREP® Spin Miniprep Kit, Qiagen, cat#27106) with 10 units of Zymolyase added (Zymo Research, cat# E1002). The yeast suspension was incubated for 10 minutes in a 37° C. waterbath. DNA from the yeast was isolated using the standard QIAPREP® Spin Miniprep Kit protocol (Qiagen, cat#27106), starting at the step of adding reagent P2.

Transformation of electrocompetent *E. coli* host cells (DH12S) was done using 5 µl of the yeast DNA prep and 50 µl of cells. The cells were electropulsed at 2.0 kV, 25 µF, and 400 ohms. Following electroporation, 1 ml SOC (2% BACTO™ Tryptone (Difco, Detroit, Mich.), 0.5% yeast extract (Difco), 10 mM NaCl, 2.5 mM KCl, 10 mM $MgCl_2$, 10 mM $MgSO_4$, 20 mM glucose) was added and then the cells were plated in a 50 µl and a 200 µl aliquot on two LB AMP plates (LB broth (Lennox), 1.8% BACTO™ Agar (Difco), 100 mg/L Ampicillin).

The inserts of several clones for the construct were subjected to sequence analysis and one clone, containing the correct sequence, was selected. Larger scale plasmid DNA was isolated using a commercially available kit (QIAGEN Plasmid Mega Kit, Qiagen, Valencia, Calif.) according to manufacturer's instructions.

The construct was designated #1795 and was created to be as the base for the second step of construction.

Step 2

Construct #1795 was constructed as a first step to building a human B7R1 Barbell vector in pZMP42. #1795 contains a B7R1-Fc5 fragment in vector pZMP42 which includes a 3' addition consisting of a linker sequence, and a multiple cloning region containing the restriction sites BspEI and BglII.

The second step of construction involves the generation of a B7R1ECD fragment using a previously generated clone as a template. The B7R1ECD fragment had a BspEI restriction cleavage site added to the 5' end of the fragment and a BglII site added to the 3' end of the fragment, and was generated using primers zc59435 (SEQ ID NO:77), zc60392 (SEQ ID NO:78), and zc59434 (SEQ ID NO:45). The fragment was created using the following PCR conditions: 1 cycle, 94° C., 5 minutes; 35 cycles, 94° C., 1 minute, followed by 58° C., 2 minutes, followed by 72° C., 3 minutes; 1 cycle, 72° C., 10 minutes.

The PCR reaction mixtures were run on a 1% agarose gel and a band corresponding to the sizes of the inserts were gel-extracted using a QIAQUICK™ Gel Extraction Kit (Qiagen, Cat. No. 28704).

Both construct #1795 and the second step B7R1ECD fragment were digested using BspEI and BglII. The digested DNA for construct #1795 and the second step B7R1ECD fragment were run on a 1% agarose gel and a band corresponding to the sizes of the DNA were gel-extracted using a QIAQUICK™ Gel Extraction Kit (Qiagen, Cat. No. 28704). The two purified DNA preparations were then ligated together using methods known in the art.

Transformation of electrocompetent *E. coli* host cells (DH12S) was done using 1 µl of the ligation prep and 50 µl of cells. The cells were electropulsed at 2.0 kV, 25 µF, and 400 ohms. Following electroporation, 1 ml SOC (2% BACTO™ Tryptone (Difco, Detroit, Mich.), 0.5% yeast extract (Difco), 10 mM NaCl, 2.5 mM KCl, 10 mM $MgCl_2$, 10 mM $MgSO_4$, 20 mM glucose) was added and then the cells were plated in a 50 µl and a 200 µl aliquot on two LB AMP plates (LB broth (Lennox), 1.8% BACTO™ Agar (Difco), 100 mg/L Ampicillin).

The inserts of several clones for the construct were subjected to sequence analysis and one clone, containing the correct sequence, was selected. Larger scale plasmid DNA was isolated using a commercially available kit (QIAGEN Plasmid Mega Kit, Qiagen, Valencia, Calif.) according to manufacturer's instructions. This clone was designated #1812.

The full-length nucleotide coding sequence and corresponding amino acid sequence for B7R1-Barbell, with the native signal sequence, are shown in SEQ ID NOs:5 and 6, respectively. The mature form of B7R1-Barbell corresponds to amino acids 22-498 of SEQ ID NO:6 (encoded by nucleotides 64-1494 of SEQ ID NO:5).

Expression of B7R1-Barbell

Three sets of 200 µg of the construct #1812 were each digested with 200 units of Pvu I at 37° C. for three hours and then were precipitated with IPA and spun down in a 1.5 mL microfuge tube. The supernatant was decanted off the pellet, and the pellet was washed with 1 mL of 70% ethanol and allowed to incubate for 5 minutes at room temperature. The tube was spun in a microfuge for 10 minutes at 14,000 RPM and the supernatant was decanted off the pellet. The pellet was then resuspended in 750 μl of ZF1 media in a sterile environment, allowed to incubate at 60° C. for 10 minutes, and was allowed to cool to room temperature. 5×106 CHO DXB11 5×SA cells were spun down in each of three tubes and were resuspended using the DNA-media solution. The DNA/cell mixtures were placed in a 0.4 cm gap cuvette and electroporated using the following parameters: 950 μF, high capacitance, and 300 V. The contents of the cuvettes were then removed, pooled, and diluted to 25 mLs with ZF1 media and placed in a 125 mL shake flask. The flask was placed in an incubator on a shaker at 37° C., 6% $CO_2$, and shaking at 120 RPM.

The cell line was subjected to nutrient selection followed by step amplification to 200 nM methotrexate (MTX). Expression was confirmed by western blot, and the cell line was scaled-up and protein purification followed.

Example 3

Construction and Expression of Murine B7R1Tandem (mB7R1-Tandem)

An expression plasmid containing mB7R1m-mB7R1-mFc2 (mB7R1-Tandem with the native mB7R1 leader sequence; polynucleotide sequence shown in SEQ ID NO:11; encoded polypeptide sequence shown in SEQ ID NO:12) was constructed via ligation into a previously modified version of expression vector pZMP42 containing a mFc2 insert (the construct described in step 1 of Example 1).

A DNA fragment containing mB7R1 extracellular domain (ECD) was made using a previously generated clone as a template. The fragment had an EcoRI site engineered into its 5' end, the mB7R1ECD, and a Gly-Ser linker, and was generated using primers zc60639 (SEQ ID NO:36), zc60640 (SEQ ID NO:46), and zc60644 (SEQ ID NO:47). A second DNA fragment was generated with overlap into the Gly-Ser linker of the first fragment on the 3' end, mB7R1ECD, and a Bgl II site on the 3' end of the fragment, and was generated using primers zc60642 (SEQ ID NO:48) and zc28844 (SEQ ID NO:49).

The PCR reaction mixtures were run on a 1% agarose gel and a band corresponding to the sizes of the inserts were gel-extracted using a QIAQUICK™ Gel Extraction Kit (Qiagen, Cat. No. 28704).

These two DNA fragments were fused into a single fragment using overlap PCR. The two gel purified fragments were added into a PCR tube and were amplified using primers zc60639 (SEQ ID NO:36) and zc28844 (SEQ ID NO:49). The resulting fragment contained a 5' EcoRI site and a 3' Bgl II site flanking the core sequence mB7R1-mB7R1.

The PCR reaction mixture was run on a 1% agarose gel and a band corresponding to the size of the insert was gel-extracted using a QIAQUICK™ Gel Extraction Kit (Qiagen, Cat. No. 28704).

Both the purified fragment and the modified vector pZMP42 were digested using EcorI and BglII, the bands of interested were isolated and were gel purified using a QIAQUICK™ Gel Extraction Kit (Qiagen, Cat. No. 28704). The purified fragments were then ligated using methods known in the art, such that the mB7R1-mB7R1 fragment was in-frame with the mFc2 contained in the modified pZMP42 vector. The resulting construct would express a protein consisting of mB7R1-mB7R1-mFc2.

Plasmid pZMP42 is a mammalian expression vector containing an expression cassette having the MPSV promoter, multiple restriction sites for insertion of coding sequences, and an otPA signal peptide sequence; an internal ribosome entry site (IRES) element from Hepatitis C virus, and the extracellular domain of CD8 truncated at the C-terminal end of the transmembrane domain; an internal ribosome entry site (IRES) element from poliovirus, a DHFR gene, and the SV40 terminator; an *E. coli* origin of replication; and URA3 and CEN-ARS sequences required for selection and replication in *S. cerevisiae*. It was constructed from pZMP21 (patent pub. No. US 2003/0232414 A1) (deposited at the American Type Culture Collection, 10801 University Boulevard, Manassas, Va. 20110-2209, designated as ATCC# PTA-5266).

Transformation of electrocompetent *E. coli* host cells (DH12S) was done using 1 μl of the ligation DNA prep and 50 μl of cells. The cells were electropulsed at 2.0 kV, 25 μF, and 400 ohms Following electroporation, 1 ml SOC (2% BACTO™ Tryptone (Difco, Detroit, Mich.), 0.5% yeast extract (Difco), 10 mM NaCl, 2.5 mM KCl, 10 mM $MgCl_2$, 10 mM $MgSO_4$, 20 mM glucose) was added and then the cells were plated in a 50 μl and a 200 μl aliquot on two LB AMP plates (LB broth (Lennox), 1.8% BACTO™ Agar (Difco), 100 mg/L Ampicillin).

The inserts of several clones for the construct were subjected to sequence analysis and one clone, containing the correct sequence, was selected. Larger scale plasmid DNA was isolated using a commercially available kit (QIAGEN Plasmid Mega Kit, Qiagen, Valencia, Calif.) according to manufacturer's instructions. The final clone was designated construct #1864.

The full-length nucleotide coding sequence and corresponding amino acid sequence for mB7R1-Tandem, with the native signal sequence, are shown in SEQ ID NOs:11 and 12, respectively. The mature form of mB7R1-Tandem corresponds to amino acids 26-504 or 26-503 of SEQ ID NO:12 (encoded by nucleotides 76-1512 or 76-1509, respectively, of SEQ ID NO:11).

Expression of mB7R1-Tandem

Three sets of 200 μg of the construct #1864 were each digested with 200 units of Pvu I at 37° C. for three hours and then were precipitated with IPA and spun down in a 1.5 mL microfuge tube. The supernatant was decanted off the pellet, and the pellet was washed with 1 mL of 70% ethanol and allowed to incubate for 5 minutes at room temperature. The tube was spun in a microfuge for 10 minutes at 14,000 RPM and the supernatant was decanted off the pellet. The pellet was then resuspended in 750 μl of ZF1 media in a sterile environment, allowed to incubate at 60° C. for 10 minutes, and was allowed to cool to room temperature. 5×106 CHO DXB11 5×SA cells were spun down in each of three tubes and were resuspended using the DNA-media solution. The DNA/cell mixtures were placed in a 0.4 cm gap cuvette and electroporated using the following parameters: 950 μF, high capacitance, and 300 V. The contents of the cuvettes were then removed, pooled, and diluted to 25 mLs with ZF1 media and placed in a 125 mL shake flask. The flask was placed in an incubator on a shaker at 37° C., 6% $CO_2$, and shaking at 120 RPM.

The cell line was subjected to nutrient selection followed by step amplification to 200 nM methotrexate (MTX). Expression was confirmed by western blot, and the cell line was scaled-up and protein purification followed.

Example 4

Construction and Expression of Human B7R1Tandem (B7R1-Tandem)

An expression plasmid containing B7R1-B7R1-Fc5 (B7R1-Tandem with the native B7R1 leader sequence; polynucleotide sequence shown in SEQ ID NO:7; encoded polypeptide sequence shown in SEQ ID NO:8) was constructed via ligation into a previously generated construct designated construct #1795 (the construct described in step 1 of Example 2), which contains a B7R1-Fc5 insert in the expression vector pZMP42. Construction was carried out in a two step process.

Plasmid pZMP42 is a mammalian expression vector containing an expression cassette having the MPSV promoter, multiple restriction sites for insertion of coding sequences, and an otPA signal peptide sequence; an internal ribosome entry site (IRES) element from Hepatitis C virus, and the extracellular domain of CD8 truncated at the C-terminal end of the transmembrane domain; an internal ribosome entry site (IRES) element from poliovirus, a DHFR gene, and the SV40 terminator; an *E. coli* origin of replication; and URA3 and CEN-ARS sequences required for selection and replication in *S. cerevisiae*. It was constructed from pZMP21 (patent pub. No. US 2003/0232414 A1) (deposited at the American Type Culture Collection, 10801 University Boulevard, Manassas, Va. 20110-2209, designated as ATCC# PTA-5266).

Step 1

A DNA fragment containing B7R1 extracellular domain (ECD) was made using a previously generated clone as a template. The fragment had an EcoRI site engineered into its 5' end, the B7R1ECD, a Gly-Ser linker incorporating a BspEI site, and was generated using primers zc53051 (SEQ ID NO:41), zc62529 (SEQ ID NO:50), and zc62530 (SEQ ID NO:51). This fragment was created with the following PCR conditions: 1 cycle, 94° C., 5 minutes; 35 cycles, 94° C., 1 minute, followed by 58° C., 2 minutes, followed by 72° C., 3 minutes; 1 cycle, 72° C., 10 minutes.

The PCR reaction mixture was run on a 1% agarose gel and a band corresponding to the size of the insert was gel-extracted using a QIAQUICK™ Gel Extraction Kit (Qiagen, Cat. No. 28704).

Both construct #1795 and the purified PCR fragment were digested using EcoRI and BspEI. The digested DNA for construct #1795 and the PCR fragment were run on a 1% agarose gel and a band corresponding to the sizes of the DNA were gel-extracted using a QIAQUICK™ Gel Extraction Kit (Qiagen, Cat. No. 28704). The two purified DNA preparations were then ligated together using methods known in the art.

Transformation of electrocompetent *E. coli* host cells (DH12S) was done using 1 µl of the ligation DNA prep and 50 µl of cells. The cells were electropulsed at 2.0 kV, 25 µF, and 400 ohms. Following electroporation, 1 ml SOC (2% BACTO™ Tryptone (Difco, Detroit, Mich.), 0.5% yeast extract (Difco), 10 mM NaCl, 2.5 mM KCl, 10 mM $MgCl_2$, 10 mM $MgSO_4$, 20 mM glucose) was added and then the cells were plated in a 50 µl and a 200 µl aliquot on two LB AMP plates (LB broth (Lennox), 1.8% BACTO™ Agar (Difco), 100 mg/L Ampicillin).

The inserts of several clones for the construct were subjected to sequence analysis and one clone, containing the correct sequence, was selected. Larger scale plasmid DNA was isolated using a commercially available kit (QIAGEN Plasmid Mega Kit, Qiagen, Valencia, Calif.) according to manufacturer's instructions. The construct was used as the base for the second step of construction.

Step 2

The second step of construction involves the generation of a B7R1-Fc5 fragment (human B7R1 extracellular domain (ECD) fused to effector function minus Fc fragment Fc5) using a previously generated clone as a template. The B7R1-Fc5 fragment had a BspEI restriction cleavage site added to the 5' end of the fragment, and a Bgl II site added to the 3' end of the fragment, and was generated using primers zc62531 (SEQ ID NO:52) and zc62532 (SEQ ID NO:53). The fragment was created using the following PCR conditions: 1 cycle, 94° C., 5 minutes; 35 cycles, 94° C., 1 minute, followed by 58° C., 2 minutes, followed by 72° C., 3 minutes; 1 cycle, 72° C., 10 minutes.

The PCR reaction mixtures were run on a 1% agarose gel and a band corresponding to the sizes of the inserts were gel-extracted using a QIAQUICK™ Gel Extraction Kit (Qiagen, Cat. No. 28704).

Both the construct from the first step and the second step B7R1-Fc5 fragment were digested using BspEI and Bgl II. The digested DNA for the first step construct and the second step B7R1-Fc5 fragment were run on a 1% agarose gel and a band corresponding to the sizes of the DNA were gel-extracted using a QIAQUICK™ Gel Extraction Kit (Qiagen, Cat. No. 28704). The two purified DNA preparations were then ligated together using methods known in the art.

Transformation of electrocompetent *E. coli* host cells (DH12S) was done using 1 µl of the ligation prep and 50 µl of cells. The cells were electropulsed at 2.0 kV, 25 µF, and 400 ohms. Following electroporation, 1 ml SOC (2% BACTO™ Tryptone (Difco, Detroit, Mich.), 0.5% yeast extract (Difco), 10 mM NaCl, 2.5 mM KCl, 10 mM $MgCl_2$, 10 mM $MgSO_4$, 20 mM glucose) was added and then the cells were plated in a 50 µl and a 200 µl aliquot on two LB AMP plates (LB broth (Lennox), 1.8% BACTO™ Agar (Difco), 100 mg/L Ampicillin).

The inserts of several clones for the construct were subjected to sequence analysis and one clone, containing the correct sequence, was selected. Larger scale plasmid DNA was isolated using a commercially available kit (QIAGEN Plasmid Mega Kit, Qiagen, Valencia, Calif.) according to manufacturer's instructions. The clone was designated #1914.

The full-length nucleotide coding sequence and corresponding amino acid sequence for B7R1-Tandem, with the native signal sequence, are shown in SEQ ID NOs:7 and 8, respectively. The mature form of B7R1-Tandem corresponds to amino acids 22-513 or 22-512 of SEQ ID NO:8 (encoded by nucleotides 64-1539 or 64-1536, respectively, of SEQ ID NO:7).

Expression of B7R1-Tandem

Three sets of 200 µg of the construct #1914 were each digested with 200 units of Pvu I at 37° C. for three hours and then were precipitated with IPA and spun down in a 1.5 mL microfuge tube. The supernatant was decanted off the pellet, and the pellet was washed with 1 mL of 70% ethanol and allowed to incubate for 5 minutes at room temperature. The tube was spun in a microfuge for 10 minutes at 14,000 RPM and the supernatant was decanted off the pellet. The pellet was then resuspended in 750 µl of ZF1 media in a sterile environment, allowed to incubate at 60° C. for 10 minutes, and was allowed to cool to room temperature. 5×106 CHO DXB11 5×SA cells were spun down in each of three tubes and were resuspended using the DNA-media solution. The DNA/cell mixtures were placed in a 0.4 cm gap cuvette and electroporated using the following parameters: 950 µF, high capacitance, and 300 V. The contents of the cuvettes were then removed, pooled, and diluted to 25 mLs with ZF1 media and placed in a 125 mL shake flask. The flask was placed in an incubator on a shaker at 37° C., 6% $CO_2$, and shaking at 120 RPM.

The cell line was subjected to nutrient selection followed by step amplification to 200 nM methotrexate (MTX). Expression was confirmed by western blot, and the cell line was scaled-up and protein purification followed.

Example 5

Construction and Expression of Human B7R1Barbell with G25 Mature Start (B7R11G25-P1411-Barbell) Using otPA Leader Sequence An expression plasmid containing B7R1[G25-P141]-Fc5-B7R1[G25-P141] (B7R1[G25-P141]-Barbell; polynucleotide sequence shown in residues 106-1518 of SEQ ID NO:13; encoded polypeptide sequence shown in residues 36-506 of SEQ ID NO:14) was constructed via homologous recombination using three DNA fragments that, when combined, contain the sequence for B7R1[G25-P141]-Barbell, and the expression vector pZMP42.

The B7R1[G25-P141]-Barbell fragment was generated by PCR amplification of three fragments using a previously generated clone of B7R1-Barbell as the template. The first fragment was created using oligos zc64230 (SEQ ID NO:54) and zc64219 (SEQ ID NO:55) which includes a 5' flanking sequence to the vector, part of the first B7R1 extracellular domain (ECD) module up to residue C69, and overlap into the residues behind C69. The second fragment was generated using oligos zc64215 (SEQ ID NO:56) and zc64216 (SEQ ID NO:57) which span from flanking sequence into the first fragment, through residue C69 of the first B7R1 module, and to the end of Fc5. The final fragment was synthetically created via overlap PCR using oligos zc64228 (SEQ ID NO:58), zc64220 (SEQ ID NO:59), zc64224 (SEQ ID NO:60), zc64231 (SEQ ID NO:61), zc64225 (SEQ ID NO:62), zc64221 (SEQ ID NO:63), zc64226 (SEQ ID NO:64), zc64222 (SEQ ID NO:65), zc64223 (SEQ ID NO:66), zc64258 (SEQ 1N NO:67), and zc59434 (SEQ ID NO:45). When assembled by yeast recombination, the fusion of the three fragments include a 5' overlap with the pZMP42 vector, the otPA leader sequence, a first B7R1[G25-P141] module, fused to Fc5, fused to a second B7R1[G25-P141] module, and a 3' overlap with the pZMP42 vector sequence. PCR conditions used to generate each of the fragments were as follows: 1 cycle, 94° C., 5 minutes; 35 cycles, 94° C., 1 minute, followed by 58° C., 2 minutes, followed by 72° C., 3 minutes; 1 cycle, 72° C., 10 minutes.

The PCR reaction mixtures were run on a 1% agarose gel and bands corresponding to the sizes of the inserts were gel-extracted using a QIAQUICK™ Gel Extraction Kit (Qiagen, Cat. No. 28704).

Plasmid pZMP42 is a mammalian expression vector containing an expression cassette having the MPSV promoter, multiple restriction sites for insertion of coding sequences, and an otPA signal peptide sequence; an internal ribosome entry site (IRES) element from Hepatitis C virus, and the extracellular domain of CD8 truncated at the C-terminal end of the transmembrane domain; an internal ribosome entry site (IRES) element from poliovirus, a DHFR gene, and the SV40 terminator; an *E. coli* origin of replication; and URA3 and CEN-ARS sequences required for selection and replication in *S. cerevisiae*. It was constructed from pZMP21 (US Patent Application Publication No. US 2003/0232414 A1) (deposited at the American Type Culture Collection, 10801 University Boulevard, Manassas, Va. 20110-2209, designated as ATCC# PTA-5266).

The plasmid pZMP42 was cut with BglII prior to recombination in yeast with the PCR fragment. One hundred microliters of competent yeast (*S. cerevisiae*) cells were independently combined with 3 µl of each of the insert DNA fragments and 100 ng of cut pZMP42 vector, and the mix was transferred to a 0.2-cm electroporation cuvette. The yeast/DNA mixture was electropulsed using power supply (BioRad Laboratories, Hercules, Calif.) settings of 0.75 kV (5 kV/cm), Go ohms, and 25 g. Six hundred µl of 1.2 M sorbitol was added to the cuvette, and the yeast was plated in a 100-µl and 300 µl aliquot onto two URA-D plates and incubated at 30° C. After about 72 hours, the Ura+ yeast transformants from a single plate were resuspended in 1 ml H2O and spun briefly to pellet the yeast cells. The cell pellet was resuspended by vortex in 0.1 ml of lysis buffer (2% Triton X-100, 1% SDS, 100 mM NaCl, 10 mM Tris, pH 8.0, 1 mM EDTA), and 0.1 mL of P1 (from QIAPREP® Spin Miniprep Kit, Qiagen, cat#27106) with 10 units of Zymolyase added (Zymo Research, cat# E1002). The yeast suspension was incubated for 10 minutes in a 37° C. waterbath. DNA from the yeast was isolated using the standard QIAPREP® Spin Miniprep Kit protocol (Qiagen, cat#27106), starting at the step of adding reagent P2.

Transformation of electrocompetent *E. coli* host cells (DH12S) was done using 5 µl of the yeast DNA prep and 50 µl of cells. The cells were electropulsed at 2.0 kV, 25 µF, and 400 ohms. Following electroporation, 1 ml SOC (2% BACTO™ Tryptone (Difco, Detroit, Mich.), 0.5% yeast extract (Difco), 10 mM NaCl, 2.5 mM KCl, 10 mM $MgCl_2$, 10 mM $MgSO_4$, 20 mM glucose) was added and then the cells were plated in a 50 µl and a 200 µl aliquot on two LB AMP plates (LB broth (Lennox), 1.8% BACTO™ Agar (Difco), 100 mg/L Ampicillin).

The inserts of several clones for the construct were subjected to sequence analysis and one clone, containing the correct sequence, was selected. Larger scale plasmid DNA was isolated using a commercially available kit (QIAGEN Plasmid Mega Kit, Qiagen, Valencia, Calif.) according to manufacturer's instructions. The construct was designated construct #2024.

The full-length nucleotide coding sequence and corresponding amino acid sequence for B7R1[G25-P141]-Barbell, with the otPA signal sequence, are shown in SEQ ID NOs:13 and 14, respectively. The mature form of B7R1[G25-P141]-Barbell corresponds to amino acids 36-506 of SEQ ID NO:14 (encoded by nucleotides 106-1518 of SEQ ID NO:13).

Expression of B7R1[G25-P 141]-Barbell

Three sets of 200 µg of the construct were each digested with 200 units of Pvu I at 37° C. for three hours and then were precipitated with IPA and spun down in a 1.5 mL microfuge tube. The supernatant was decanted off the pellet, and the pellet was washed with 1 mL of 70% ethanol and allowed to incubate for 5 minutes at room temperature. The tube was spun in a microfuge for 10 minutes at 14,000 RPM and the supernatant was decanted off the pellet. The pellet was then resuspended in 750 µl of ZF1 media in a sterile environment, allowed to incubate at 60° C. for 10 minutes, and was allowed to cool to room temperature. 5×106 CHO DXB11 5×SA cells were spun down in each of three tubes and were resuspended using the DNA-media solution. The DNA/cell mixtures were placed in a 0.4 cm gap cuvette and electroporated using the following parameters: 950 µF, high capacitance, and 300 V.

The contents of the cuvettes were then removed, pooled, and diluted to 25 mLs with ZF1 media and placed in a 125 mL shake flask. The flask was placed in an incubator on a shaker at 37° C., 6% $CO_2$, and shaking at 120 RPM.

The cell line was subjected to nutrient selection followed by step amplification to 200 nM methotrexate (MTX). Expression was confirmed by western blot, and the cell line was scaled-up and protein purification followed.

Example 6

Construction and Expression of Human B7R1Barbell with G25 Mature Start and C69Y Mutation (B7R1[G25-P141][C69Y]-Barbell) Using otPA Leader Sequence An expression plasmid containing B7R1[G25-P141][C69Y]-Fc5-B7R1 [G25-P141] [C69Y] (B7R1 [G25-P141] [C69Y]-Barbell; polynucleotide sequence shown in residues 106-1518 of SEQ ID NO:13; encoded polypeptide sequence shown in residues 36-506 of SEQ ID NO:16) was constructed via homologous recombination using three DNA fragments that, when combined, contain the sequence for B7R1[G25-P141][C69Y]-Barbell, and the expression vector pZMP42.

The B7R1[G25-P141][C69Y]-Barbell fragment was generated by PCR amplification of three fragments using a previously generated clone of B7R1-Barbell as the template. The first fragment was created using oligos zc64230 (SEQ ID NO:54) and zc64218 (SEQ ID NO:68) which includes a 5' flanking sequence to the vector, part of the first B7R1 extracellular domain (ECD) module up to residue C69, and overlap into the residues behind C69. The second fragment was generated using oligos zc64215 (SEQ ID NO:56) and zc64216 (SEQ ID NO:57) which span from flanking sequence into the first fragment, through residue C69 of the first B7R1 module, and to the end of Fc5. The final fragment was synthetically created via overlap PCR using oligos zc64228 (SEQ ID NO:58), zc64220 (SEQ ID NO:59), zc64224 (SEQ ID NO:60), zc64227 (SEQ ID NO:69), zc64225 (SEQ ID NO:62), zc64221 (SEQ ID NO:63), zc64226 (SEQ ID NO:64), zc64222 (SEQ ID NO:65), zc64223 (SEQ ID NO:66), zc64258 (SEQ ID NO:67), and zc59434 (SEQ ID NO:45). When assembled by yeast recombination, the fusion of the three fragments include a 5' overlap with the pZMP42 vector, the otPA leader sequence, a first B7R1[G25-P141][C69Y] module, fused to Fc5, fused to a second B7R1[G25-P141][C69Y] module, and a 3' overlap with the pZMP42 vector sequence. PCR conditions used to generate each of the fragments were as follows: 1 cycle, 94° C., 5 minutes; 35 cycles, 94° C., 1 minute, followed by 58° C., 2 minutes, followed by 72° C., 3 minutes; 1 cycle, 72° C., 10 minutes.

The PCR reaction mixtures were run on a 1% agarose gel and bands corresponding to the sizes of the inserts were gel-extracted using a QIAQUICK™ Gel Extraction Kit (Qiagen, Cat. No. 28704).

The insert contains modifications of the B7R1ECD modules. Residue C69 was mutated to tyrosine (Y). The N-terminal start of the mature protein was also adjusted away from the human predicted start (amino acid residue 22) to amino acid residue 25 (G25). These changes were implemented to overcome several issues observed with the production of the human protein.

Plasmid pZMP42 is a mammalian expression vector containing an expression cassette having the MPSV promoter, multiple restriction sites for insertion of coding sequences, and an otPA signal peptide sequence; an internal ribosome entry site (IRES) element from Hepatitis C virus, and the extracellular domain of CD8 truncated at the C-terminal end of the transmembrane domain; an internal ribosome entry site (IRES) element from poliovirus, a DHFR gene, and the SV40 terminator; an *E. coli* origin of replication; and URA3 and CEN-ARS sequences required for selection and replication in *S. cerevisiae*. It was constructed from pZMP21 (US Patent Publication No. US 2003/0232414 A1) (deposited at the American Type Culture Collection, 10801 University Boulevard, Manassas, Va. 20110-2209, designated as ATCC# PTA-5266).

The plasmid pZMP42 was cut with BglII prior to recombination in yeast with the PCR fragment. One hundred microliters of competent yeast (*S. cerevisiae*) cells were independently combined with 3 μl of each of the insert DNA fragments and 100 ng of cut pZMP42 vector, and the mix was transferred to a 0.2-cm electroporation cuvette. The yeast/DNA mixture was electropulsed using power supply (BioRad Laboratories, Hercules, Calif.) settings of 0.75 kV (5 kV/cm), Go ohms, and 25 μl. Six hundred μl of 1.2 M sorbitol was added to the cuvette, and the yeast was plated in a 100-μl and 300 μl aliquot onto two URA-D plates and incubated at 30° C. After about 72 hours, the Ura+ yeast transformants from a single plate were resuspended in 1 ml H2O and spun briefly to pellet the yeast cells. The cell pellet was resuspended by vortex in 0.1 ml of lysis buffer (2% Triton X-100, 1% SDS, 100 mM NaCl, 10 mM Tris, pH 8.0, 1 mM EDTA), and 0.1 mL of P1 (from QIAPREP® Spin Miniprep Kit, Qiagen, cat#27106) with 10 units of Zymolyase added (Zymo Research, cat# E1002). The yeast suspension was incubated for 10 minutes in a 37° C. waterbath. DNA from the yeast was isolated using the standard QIAPREP® Spin Miniprep Kit protocol (Qiagen, cat#27106), starting at the step of adding reagent P2.

Transformation of electrocompetent *E. coli* host cells (DH12S) was done using 5 μl of the yeast DNA prep and 50 μl of cells. The cells were electropulsed at 2.0 kV, 25 μF, and 400 ohms. Following electroporation, 1 ml SOC (2% BACTO™ Tryptone (Difco, Detroit, Mich.), 0.5% yeast extract (Difco), 10 mM NaCl, 2.5 mM KCl, 10 mM $MgCl_2$, 10 mM $MgSO_4$, 20 mM glucose) was added and then the cells were plated in a 50 μl and a 200 μl aliquot on two LB AMP plates (LB broth (Lennox), 1.8% BACTO™ Agar (Difco), 100 mg/L Ampicillin).

The inserts of several clones for the construct were subjected to sequence analysis and one clone, containing the correct sequence, was selected. Larger scale plasmid DNA was isolated using a commercially available kit (QIAGEN Plasmid Mega Kit, Qiagen, Valencia, Calif.) according to manufacturer's instructions. The construct was designated construct #2026.

The full-length nucleotide coding sequence and corresponding amino acid sequence for B7R1[G25-P141][C69Y]-Barbell, with the otPA signal sequence, are shown in SEQ ID NOs:15 and 16, respectively. The mature form of B7R1[G25-P141]-Barbell corresponds to amino acids 36-506 of SEQ ID NO:16 (encoded by nucleotides 106-1518 of SEQ ID NO:15).

Expression of B7R1 [G25-P141][C69Y]-Barbell

Three sets of 200 μg of the construct were each digested with 200 units of Pvu I at 37° C. for three hours and then were precipitated with IPA and spun down in a 1.5 mL microfuge tube. The supernatant was decanted off the pellet, and the pellet was washed with 1 mL of 70% ethanol and allowed to incubate for 5 minutes at room temperature. The tube was spun in a microfuge for 10 minutes at 14,000 RPM and the supernatant was decanted off the pellet. The pellet was then resuspended in 750 μl of ZF1 media in a sterile environment, allowed to incubate at 60° C. for 10 minutes, and was allowed to cool to room temperature. 5×106 CHO DXB11 5×SA cells were spun down in each of three tubes and were resuspended using the DNA-media solution. The DNA/cell mixtures were placed in a 0.4 cm gap cuvette and electroporated using the following parameters: 950 μF, high capacitance, and 300 V. The contents of the cuvettes were then removed, pooled, and diluted to 25 mLs with ZF1 media and placed in a 125 mL shake flask. The flask was placed in an incubator on a shaker at 37° C., 6% $CO_2$, and shaking at 120 RPM.

The cell line was subjected to nutrient selection followed by step amplification to 200 nM methotrexate (MTX). Expression was confirmed by western blot, and the cell line was scaled-up and protein purification followed.

Example 7

Construction and Expression of Human B7R1Barbell with G25 Mature Start and C69Y Mutation (B7R1[G25-P141][C69Y]-Barbell) Using EMIL Leader Sequence An expression plasmid containing B7R1[G25-P141][C69Y]-Fc5-B7R1 [G25-P141] [C69Y] (B7R1 [G25-P141] [C69Y]-Barbell; polynucleotide sequence shown in residues 67-1497 of SEQ ID NO:17; encoded polypeptide sequence shown in residues 23-493 of SEQ ID NO:18) was constructed via homologous recombination using a DNA fragment containing the sequence for B7R1[G25-P141][C69Y]-Barbell, and the expression vector pZMP42. The B7R1[G25-P141][C69Y]-Barbell fragment was generated by PCR amplification using primers zc65030 (SEQ ID NO:70), zc65029 (SEQ ID NO:71), and zc59434 (SEQ ID NO:45).

The B7R1[G25-P141][C69Y]-Barbell fragment was made using a previously generated clone of B7R1[G25-P141][C69Y]-Barbell as the template, designated construct #2026. The fragment includes a 5' overlap with the pZMP42 vector sequence, a leader sequence designated as "EMIL" (residues 1-66 of SEQ ID NO:17; encoded amino acid sequence shown in residues 1-22 of SEQ ID NO:18), the B7R1[G25-P141][C69Y]-Barbell segment (residues 67-1497 of SEQ ID NO:17; encoded amino acid sequence shown in residues 23-493 of SEQ ID NO:18), and a 3' overlap with the pZMP42 vector sequence. PCR conditions used were as follows: 1 cycle, 94° C., 5 minutes; 35 cycles, 94° C., 1 minute, followed by 58° C., 2 minutes, followed by 72° C., 3 minutes; 1 cycle, 72° C., 10 minutes.

The PCR reaction mixture was run on a 1% agarose gel and a band corresponding to the size of the insert was gel-extracted using a QIAQUICK™ Gel Extraction Kit (Qiagen, Cat. No. 28704).

The insert contains modifications of the B7R1 extracellular domain (ECD) modules. Residue C69 was mutated to tyrosine (Y). The N-terminal start of the mature protein was also adjusted away from the human predicted start (amino acid residue 22) to amino acid residue 25 (G25). These changes were implemented to overcome several issues observed with the production of the human protein.

Plasmid pZMP42 is a mammalian expression vector containing an expression cassette having the MPSV promoter, multiple restriction sites for insertion of coding sequences, and an otPA signal peptide sequence; an internal ribosome entry site (IRES) element from Hepatitis C virus, and the extracellular domain of CD8 truncated at the C-terminal end of the transmembrane domain; an internal ribosome entry site (IRES) element from poliovirus, a DHFR gene, and the SV40 terminator; an *E. coli* origin of replication; and URA3 and CEN-ARS sequences required for selection and replication in *S. cerevisiae*. It was constructed from pZMP21 (US Patent Application Publication No. US 2003/0232414 A1) (deposited at the American Type Culture Collection, 10801 University Boulevard, Manassas, Va. 20110-2209, designated as ATCC# PTA-5266).

The plasmid pZMP42 was cut with BglII prior to recombination in yeast with the PCR fragment. One hundred microliters of competent yeast (*S. cerevisiae*) cells were independently combined with 10 μl of the insert DNA and 100 ng of cut pZMP42 vector, and the mix was transferred to a 0.2-cm electroporation cuvette. The yeast/DNA mixture was electropulsed using power supply (BioRad Laboratories, Hercules, Calif.) settings of 0.75 kV (5 kV/cm), ∞ ohms, and 25 μF. Six hundred μl of 1.2 M sorbitol was added to the cuvette, and the yeast was plated in a 100-μl and 300 μl aliquot onto two URA-D plates and incubated at 30° C. After about 72 hours, the Ura+ yeast transformants from a single plate were resuspended in 1 ml H2O and spun briefly to pellet the yeast cells. The cell pellet was resuspended by vortex in 0.1 ml of lysis buffer (2% Triton X-100, 1% SDS, 100 mM NaCl, 10 mM Tris, pH 8.0, 1 mM EDTA), and 0.1 mL of P1 (from QIAREP® Spin Miniprep Kit, Qiagen, cat#27106) with 10 units of Zymolyase added (Zymo Research, cat# E1002). The yeast suspension was incubated for 10 minutes in a 37° C. waterbath. DNA from the yeast was isolated using the standard QIAPREP® Spin Miniprep Kit protocol (Qiagen, cat#27106), starting at the step of adding reagent P2.

Transformation of electrocompetent *E. coli* host cells (DH12S) was done using 5 μl of the yeast DNA prep and 50 μl of cells. The cells were electropulsed at 2.0 kV, 25 μF, and 400 ohms. Following electroporation, 1 ml SOC (2% BACTO™ Tryptone (Difco, Detroit, Mich.), 0.5% yeast extract (Difco), 10 mM NaCl, 2.5 mM KCl, 10 mM $MgCl_2$, 10 mM $MgSO_4$, 20 mM glucose) was added and then the cells were plated in a 50 μl and a 200 μl aliquot on two LB AMP plates (LB broth (Lennox), 1.8% BACTO™ Agar (Difco), 100 mg/L Ampicillin).

The inserts of several clones for the construct were subjected to sequence analysis and one clone, containing the correct sequence, was selected. Larger scale plasmid DNA was isolated using a commercially available kit (QIAGEN Plasmid Mega Kit, Qiagen, Valencia, Calif.) according to manufacturer's instructions. The construct was designated construct #2065.

The full-length nucleotide coding sequence and corresponding amino acid sequence for B7R1[G25-P141][C69Y]-Barbell, with the EMIL signal sequence, are shown in SEQ ID NOs:17 and 18, respectively. The mature form of B7R1[G25-P141][C69Y]-Barbell corresponds to amino acids 23-493 of SEQ ID NO:18 (encoded by nucleotides 67-1497 of SEQ ID NO:17).

Expression of B7R1[G25-P141] [C69Y]-Barbell

Three sets of 200 μg of the construct were each digested with 200 units of Pvu I at 37° C. for three hours and then were precipitated with IPA and spun down in a 1.5 mL microfuge tube. The supernatant was decanted off the pellet, and the pellet was washed with 1 mL of 70% ethanol and allowed to incubate for 5 minutes at room temperature. The tube was spun in a microfuge for 10 minutes at 14,000 RPM and the supernatant was decanted off the pellet. The pellet was then resuspended in 750 μl of ZF1 media in a sterile environment, allowed to incubate at 60° C. for 10 minutes, and was allowed to cool to room temperature. 5×106 CHO DXB11 5×SA cells were spun down in each of three tubes and were resuspended using the DNA-media solution. The DNA/cell mixtures were placed in a 0.4 cm gap cuvette and electroporated using the following parameters: 950 µF, high capacitance, and 300 V. The contents of the cuvettes were then removed, pooled, and diluted to 25 mLs with ZF1 media and placed in a 125 mL shake flask. The flask was placed in an incubator on a shaker at 37° C., 6% $CO_2$, and shaking at 120 RPM.

The cell line was subjected to nutrient selection followed by step amplification to 200 nM methotrexate (MTX). Expression was confirmed by western blot, and the cell line was scaled-up and protein purification followed.

Example 8

Construction and Expression of Human B7R1Tandem with G25 Mature Start and C69Y Mutation (B7R1[G25-P141][C69Y]-Tandem) Using EMIL Leader Sequence An expression plasmid containing B7R1[G25-P141][C69Y]-B7R1[G25-P141][C69Y]-Fc5 (B7R1[G25-P141][C69Y]-Tandem; polynucleotide sequence shown in residues 67-1524 of SEQ ID NO:19; encoded polypeptide sequence shown in residues 23-508 of SEQ ID NO:20) was constructed via homologous recombination using a DNA fragment containing the sequence for B7R1 [G25-P141] [C69Y]-B7R1 [G25-P141] [C69Y] (residues 23-139 of SEQ ID NO:20), a DNA fragment encoding Fc5, and the expression vector pZMP42. The B7R1[G25-P141][C69Y]-B7R1[G25-P141][C69Y] fragment was generated by a series of PCR amplifications using oligos zc65030 (SEQ ID NO:70), zc65029 (SEQ ID NO:71), zc65050 (SEQ ID NO:72), zc65051 (SEQ ID NO:73), and zc65052 (SEQ ID NO:74). The Fc5 fragment was generated using oligos zc65053 (SEQ ID NO:75) and zc65054 (SEQ ID NO:76).

The B7R1[G25-P141][C69Y]-B7R1[G25-P141][C69Y] fragment was made using a previously generated clone of B7R1[G25-P141][C69Y]-Fc5-B7R1[G25-P141][C69Y] (B7R1[G25-P141][C69Y]-Barbell) as the template, designated construct #2026 (see Example 6). The first reaction amplified one B7R1[G25-P141][C69Y] unit with a 5' EMIL leader sequence using oligos zc65030 (SEQ ID NO:70), zc65029 (SEQ ID NO:71), and zc65050 (SEQ ID NO:72). A second reaction amplified the second B7R1[G25-P141][C69Y] unit with oligos zc65051 (SEQ ID NO:73) and zc65052 (SEQ ID NO:74). The final reaction used overlap PCR on the first two amplified products with oligos zc65030 and zc65052 to create a single, fused B7R1[G25-P141][C69Y]-B7R1[G25-P141][C69Y] fragment. The fragment includes a 5' overlap with the pZMP42 vector sequence, a leader sequence designated as "EMIL" (residues 1-66 of SEQ ID NO:19; encoded amino acid sequence shown in residues 1-22 of SEQ ID NO:20), two sequential copies of B7R1[G25-P141][C69Y] linked via a Gly-Ser linker (residues 67-828 of SEQ ID NO:19; encoded amino acid sequence shown in residues 23-276 of SEQ ID NO:20), and a 3' overlap with the 5' end of Fc5. PCR conditions for all reactions used were as follows: 1 cycle, 94° C., 5 minutes; 35 cycles, 94° C., 1 minute, followed by 58° C., 2 minutes, followed by 72° C., 3 minutes; 1 cycle, 72° C., 10 minutes.

A second fragment encoding Fc5 (residues 829-1524 of SEQ ID NO:19; encoded amino acid sequence shown in residues 277-508 of SEQ ID NO:20) was generated using primers zc65053 (SEQ ID NO:75) and zc65054 (SEQ ID NO:76). This fragment includes the Fc5 fragment and a 3' overlap with vector pZMP42.

The PCR reaction mixtures were run on a 1% agarose gel and bands corresponding to the sizes of the inserts were gel-extracted using a QIAQUICK™ Gel Extraction Kit (Qiagen, Cat. No. 28704).

The insert contains modifications of the B7R1 extracellular domain (ECD) modules. Residue C69 was mutated to tyrosine (Y). The N-terminal start of the mature protein was also adjusted away from the human predicted start (amino acid residue 22) to amino acid residue 25 (G25). These changes were implemented to overcome several issues observed with the production of the human protein.

Plasmid pZMP42 is a mammalian expression vector containing an expression cassette having the MPSV promoter, multiple restriction sites for insertion of coding sequences, and an otPA signal peptide sequence; an internal ribosome entry site (IRES) element from Hepatitis C virus, and the extracellular domain of CD8 truncated at the C-terminal end of the transmembrane domain; an internal ribosome entry site (IRES) element from poliovirus, a DHFR gene, and the SV40 terminator; an *E. coli* origin of replication; and URA3 and CEN-ARS sequences required for selection and replication in *S. cerevisiae*. It was constructed from pZMP21 (US Patent Application Publication No. US 2003/0232414 A1) (deposited at the American Type Culture Collection, 10801 University Boulevard, Manassas, Va. 20110-2209, designated as ATCC# PTA-5266).

The plasmid pZMP42 was cut with BglII prior to recombination in yeast with the PCR fragments. One hundred microliters of competent yeast (*S. cerevisiae*) cells were independently combined with 5 µl of the B7R1[G25-P141][C69Y]-B7R1[G25-P141][C69Y] fragment DNA, 5 µl of the Fc5 fragment DNA, and 100 ng of cut pZMP42 vector, and the mix was transferred to a 0.2-cm electroporation cuvette. The yeast/DNA mixture was electropulsed using power supply (BioRad Laboratories, Hercules, Calif.) settings of 0.75 kV (5 kV/cm), ∞ ohms, and 25 µF. Six hundred p. 1 of 1.2 M sorbitol was added to the cuvette, and the yeast was plated in a 100-µl and 300 µl aliquot onto two URA-D plates and incubated at 30° C. After about 72 hours, the Ura+ yeast transformants from a single plate were resuspended in 1 ml H2O and spun briefly to pellet the yeast cells. The cell pellet was resuspended by vortex in 0.1 ml of lysis buffer (2% Triton X-100, 1% SDS, 100 mM NaCl, 10 mM Tris, pH 8.0, 1 mM EDTA), and 0.1 mL of P1 (from QIAPREP® Spin Miniprep Kit, Qiagen, cat#27106) with 10 units of Zymolyase added (Zymo Research, cat# E1002). The yeast suspension was incubated for 10 minutes in a 37° C. waterbath. DNA from the yeast was isolated using the standard QIAPREP®Spin Miniprep Kit protocol (Qiagen, cat#27106), starting at the step of adding reagent P2.

Transformation of electrocompetent *E. coli* host cells (DH12S) was done using 5 µl of the yeast DNA prep and 50 µl of cells. The cells were electropulsed at 2.0 kV, 25 µF, and 400 ohms. Following electroporation, 1 ml SOC (2% BACTO™ Tryptone (Difco, Detroit, Mich.), 0.5% yeast extract (Difco), 10 mM NaCl, 2.5 mM KCl, 10 mM $MgCl_2$, 10 mM $MgSO_4$, 20 mM glucose) was added and then the cells were plated in a 50 µl and a 200 µl aliquot on two LB AMP plates (LB broth (Lennox), 1.8% BACTO™ Agar (Difco), 100 mg/L Ampicillin).

The inserts of several clones for the construct were subjected to sequence analysis and one clone, containing the correct sequence, was selected. Larger scale plasmid DNA was isolated using a commercially available kit (QIAGEN Plasmid Mega Kit, Qiagen, Valencia, Calif.) according to manufacturer's instructions. The construct was designated construct #2066.

The full-length nucleotide coding sequence and corresponding amino acid sequence for B7R1[G25-P141][C69Y]-Tandem, with the EMIL signal sequence, are shown in SEQ ID NOs:19 and 20, respectively. The mature form of B7R1 [G25-P141][C69Y]-Tandem, corresponds to amino acids 23-508 or 23-507 of SEQ ID NO:20 (encoded by nucleotides 67-1524 or 67-1521, respectively, of SEQ ID NO:19).

Expression of B7R1[G25-P141][C69Y]-Tandem

Three sets of 200 μg of the construct were each digested with 200 units of Pvu I at 37° C. for three hours and then were precipitated with IPA and spun down in a 1.5 mL microfuge tube. The supernatant was decanted off the pellet, and the pellet was washed with 1 mL of 70% ethanol and allowed to incubate for 5 minutes at room temperature. The tube was spun in a microfuge for 10 minutes at 14,000 RPM and the supernatant was decanted off the pellet. The pellet was then resuspended in 750 μl of ZF1 media in a sterile environment, allowed to incubate at 60° C. for 10 minutes, and was allowed to cool to room temperature. 5×106 CHO DXB11 5×SA cells were spun down in each of three tubes and were resuspended using the DNA-media solution. The DNA/cell mixtures were placed in a 0.4 cm gap cuvette and electroporated using the following parameters: 950 μF, high capacitance, and 300 V. The contents of the cuvettes were then removed, pooled, and diluted to 25 mLs with ZF1 media and placed in a 125 mL shake flask. The flask was placed in an incubator on a shaker at 37° C., 6% $CO_2$, and shaking at 120 RPM.

The cell line was subjected to nutrient selection followed by step amplification to 200 nM methotrexate (MTX). Expression was confirmed by western blot, and the cell line was scaled-up and protein purification followed.

Example 9

Purification of Human and Mouse B7R1Tandem and Barbell Proteins

The human and mouse soluble B7R1 extracellular domains were fused with human Fc in two configurations, Tandem and Barbell (see Examples above), for transient and stable expression. The human B7R1Fc fusion proteins were produced from transfected 293 or CHO cells and the mouse proteins from transfected CHO cells. The transfections were performed using methods known in the art. Mouse proteins consistently produced at higher levels than human forms until the human forms were engineered to achieve higher yields. (Human forms were engineered to have a mature start at glycine 25 (G25) of the native B7R1 extracellular domain, as well as to incorporate a cysteine to tyrosine mutation at position 69 (C69Y); see, e.g., Examples 7 and 8, supra). All forms were purified using the same process consisting of an affinity capture followed by concentration for buffer exchange using size exclusion chromatography. For both the human and the mouse B7R1Fc fusion proteins, the purifications were performed at the 1.5 to 10 L lab bench scale.

TABLE 3

Purification of Human and Mouse B7R1 Tandem and Barbell

| Construct | Lot | | Host | Scale (L) | Recoverd (mg/L) |
|---|---|---|---|---|---|
| | | Human Protein | | | |
| 2066 | A2751F | B7R1[G25-P141] [C69Y]-Tandem | CHO DXB11 5xSA | 1.55 | 10 |
| 2066 | A2784F | B7R1[G25-P141] [C69Y]-Tandem | 293F B | 10 | 66 |
| 2065 | A2752F | B7R1[G25-P141] [C69Y]-Barbell | CHO DXB11 5xSA | 1.5 | 6 |
| 2065 | A2783F | B7R1[G25-P141] [C69Y]-Barbell | 293F B | 10 | 47 |
| | | Mouse Protein | | | |
| 1864 | A2722F | mB7R1-Tandem | CHO DXB11 5xSA | 10 | 9.8 |
| 1863 | A2238F | mB7R1-Barbell | CHO DXB11 5xSA | 20 | 14 |

Cell culture supernatants were harvested and sterile filtered using 0.2 μm filters. Protein was purified from the filtered media by a combination of Protein A Sepharose or MabSelect SURE and Superdex 200 Size Exclusion Chromatography (all from GE Healthcare, Piscataway, N.J.) Depending on the scale, a 5 to 157 ml Protein A column was pre-eluted with 3 column volumes (CV) of 25 mM Sodium Citrate-Sodium Phosphate, 250 mM Ammonium Sulfate pH 3 buffer and equilibrated with 20 CV 25 mM Sodium Citrate-Sodium Phosphate, 250 mM Ammonium Sulfate pH 7.2. The CHO culture supernatant was loaded directly to the Protein A column at 24-42 cm/hr overnight at 4° C. to capture the B7R1Fc fusion protein in the supernatant. After loading was complete, the column was washed with at least 10 CV of equilibration buffer. Next the column was washed with at least 10 CV of 25 mM Sodium Citrate-Sodium Phosphate, 250 mM Ammonium Sulfate pH 7.2 buffer following which the bound protein was eluted at 92-149 cm/hr with a 20 CV gradient from pH 7.2 to pH 3 formed using the Citrate-Phosphate-Ammonium Sulfate buffers. Target containing fractions were collected into tubes containing 2.0 M Tris, pH 8.0, in order to immediately neutralize the eluted proteins. The fractions were pooled based on A280 inflections on the elution profiles.

The affinity pool was next concentrated to <3% of the volume of the size exclusion column by ultrafiltration either using an Amicon Ultra-15 30K NWML centrifugal device (Millipore) or a stirred cell with a 30 kD MW cutoff membrane. Then the concentrate was injected onto an appropriately sized Superdex 200 column that was pre-equilibrated in 35 mM Sodium Phosphate, 120 mM NaCl pH 7.3 at 28 cm/hr. The fractions containing the purified B7R1Fc fusion protein were pooled based on A280, filtered through a 0.2 μm filter, assayed for content and endotoxin, and frozen as aliquots at −80° C. The content of the final purified protein was determined by absorbance at A280 using the theoretical extinction coefficient. The overall process recoveries varied from 10-14 mg/L for the mouse proteins and 6-66 mg/L for the human constructs.

Analysis of Purified B7R1Tandem and Barbell Proteins

Recombinant B7R1Fc fusion proteins were characterized by SDS-PAGE (4-12% BisTris, Invitrogen, Carlsbad, Calif.) with 0.1% Coomassie 8250 staining for protein and by immunoblotting with Anti-IgG-HRP. The purified protein was electrophoresed using an Invitrogen Novex's Xcell II mini-cell, and transferred to nitrocellulose (0.2 mm; Invitrogen, Carlsbad, Calif.) at ambient temperature at 600 mA for 45 minutes in a buffer containing 25 mM Tris base, 200 mM glycine, and 20% methanol. The filters were then blocked with 10% non-fat dry milk in 50 mM Tris, 150 mM NaCl, 5 mM EDTA, 0.05% Igepal (TBS) for 15 minutes at room temperature. The nitrocellulose was quickly rinsed, and the IgG-HRP antibody (1:10,000) was added in. The blots were incubated overnight at 4° C., with gentle shaking. Following the incubation, the blots were washed three times for 10 minutes each in TBS, and then quickly rinsed in H2O. The blots were developed using commercially available chemiluminescent substrate reagents (Roche LumiLight), and the signal was captured using the ImageQuant TL instrument and software (GE Healthcare.) The purified B7R1 mouse and human Tandem and Barbell Fc fusion proteins appeared as two bands on both the Western blot and the Coomassie stained gel near 160 kDa under non-reducing conditions, and near 64 kDa under reducing conditions, suggesting glycosylated dimeric forms as expected. The proteins had the correct NH2 terminus, the correct amino acid composition, and were well characterized for mass and percent glycosylation using SEC MALS.

Example 10

Dynamic Light Scattering (DLS) Analysis of B7R1Fusion Proteins

Dynamic Light Scattering (DLS) was employed to monitor the short-term stability and aggregation of human and murine B7R1 fusion constructs at 21° C., 5° C., and 37° C. with the DynaPro Plus instrument (Wyatt Technology, Santa Barbara, Calif.) in the plate reader format. As a result of these initial studies comparing the murine to human versions, additional experiments were performed in order to compare the stability of mutated human barbell and tandem constructs to their original human counterparts.

1. Background on Analytical Technique

DLS measures the time-dependent fluctuations of scattered light intensity over a time scale of microseconds. These fluctuations in intensity are the result of particles diffusing in solution due to Brownian motion, and the rate of diffusion is related to their size. The DLS raw data is captured as an autocorrelation function plot, from which a diffusion coefficient (Dt) is obtained. When multiple species are present, e.g., monomer with larger oligomers or aggregate, a distribution of diffusion coefficients is seen after deconvolution by the Dynamics software (v. 6.0, Wyatt Technology). The hydrodynamic radius (or, Stokes radius) Rh, is then derived by the software using the Stokes-Einstein relation, which describes the theoretical relationship between the diffusion rate and size of particles in solution.

DLS is extremely sensitive to very small amounts of large species and can be used to reliably quantify protein aggregate down to 0.01% of the total sample.

2. Description of Analysis Parameters

Sample Preparation

Samples were retrieved from −80° C. storage and thawed at room temperature for 30 minutes for analysis at 1 mg/mL, or following a spin concentration step in 10K MWCO Amicon units for 25 mg/mL analysis. 200 μL aliquots were then transferred to 1.5 mL microfuge tubes and centrifuged for five minutes at 14K rpm in an Eppendorf tabletop centrifuge at ambient temperature. After centrifugation, 20 μL of sample was transferred to a Corning 384 well glass bottom plate for scanning in triplicate for each sample. A single drop of silicone oil cover was added to each well for duration of the analysis. Both sample concentrations were tested in the original formulation buffer only.

Analysis Parameters

Data was collected on each well for 60 seconds in packets of 15 seconds each. The samples were scanned after 2 hours at room temperature for the 21° C. reading, overnight at 5° C. and following a 2-hour incubation at 37° C. A separate time course experiment at 37° C. with freshly prepared samples was also conducted to monitor aggregation over time at the higher temperature.

3. Summary of Results

Key to DLS Size Distribution Classifications

The terms "monomodal" and "multimodal" describe the number of bins (or peaks) detected. The terms "monodisperse" and "polydisperse" describe the variability of species size within each bin. For example, a sample classified as monomodal/polydisperse=one bin detected which contains more than one closely related species, such as monomer/dimer/trimer.

Differences Observed Between Murine and Human Forms

Analysis of the initial forms of purified murine B7R1 showed that all four configurations, i.e., the Fc (SEQ ID NO:34), VASP (SEQ ID NO:35), barbell (SEQ ID NO:10 residues 26-489; Construct 1863) and tandem (SEQ ID NO:12 residues 26-504 or 26-503; Construct 1864) forms, were stable at all three temperatures. No instability at 37° C. was observed. Conversely, the human forms of the barbell (SEQ ID NO:6 residues 22-498; Construct 1812) and tandem (SEQ ID NO:8 residues 22-513 or 22-512; Construct 1914) molecules exhibited marked disordered aggregation and instability at 37° C., as did the human Fc (B7R1-Fc5; SEQ ID NO:79) and VASP (B7R1-VASP; SEQ ID NO:81) constructs. This aggregation was observed within 2 hours and was not reversible, suggesting the association/aggregation had proceeded through the unfolding pathway. The instability of the human B7R1 at 37° C. was observed at both the low and high concentrations and was consistent from lot to lot analyzed.

The Effect of Mutation of the Human Barbell and Tandem Forms

Mutated forms of the human B7R1 barbell and tandem molecules—B7R1[G25-P141][C69Y]-Barbell (SEQ ID NO:18 residues 23-493; see Example 7) and B7R1[G25-P141][C69Y]-Tandem (SEQ ID NO:20 residues 23-508 or 23-507; see Example 8)—were also analyzed using DLS. Data was collected at all three temperatures with an additional time course study at 37° C.

At 1 mg/mL, both mutated forms exhibit short-term stability at 21° C. and 5° C., with only minor multimerization observed, as indicated by a slight increase in the average radius. A large species of 59 nm radius was observed at T=4 hrs at 37° C., but was a minor component of the sample (0.1% by weight) and was reversibly dissociated upon cooling to ambient temperature.

At the higher concentration of 25 mg/mL, both forms had a slightly larger average radius and increased polydispersity, indicative of a slight increase in the amount of small, closely related species such as dimer/trimer, but the sample remained monomodal and monodisperse (i.e., one bin detected) and free of HMW aggregate.

Of these two forms, the barbell was considered slightly more stable*, however, neither sample exhibited any significant instability at 37° C. over the short term, up to the T=18 hours final measurement.

CONCLUSION

B7R1[G25-P141][C69Y]-Barbell and B7R1[G25-P141][C69Y]-Tandem exhibited a desired increase in stability at 37° C. at both low and high concentration, with complete amelioration of the aggregation problems observed with the original human constructs Example 11

Binding Assay for Human B7R1Constructs

A cell-based binding assay for B7R1 receptor-containing proteins was established using the known PVR (polio virus receptor; CD155)-B7R1 receptor-ligand pairing. P815 cells (murine mastocytoma cell line, ATCC) were transfected with a human PVR expression vector containing a neomycin (G418) selection marker using standard techniques. After outgrowth under G418 selection, expression of hPVR was confirmed by flow cytometry. A parallel transfection of P815 cells with an empty vector (control) was grown out under G418 selection and confirmed to have no expression of hPVR by flow cytometry.

Four human B7R1 receptor-containing proteins were tested for their ability to bind hPVR-expressing P815 cells: A1648.1, a hB7R1-VASP molecule (SEQ ID NO:81) that was directly labeled with AlexaFluor 647 through amine conjugation; A2648F, a hB7R1-Fc2 dimer (SEQ ID NO:79); A2751F, a hB7R1-“Barbell-Fc” protein (SEQ ID NO:18 residues 23-493); A2752F, a hB7r1-“Tandem Fc” protein (SEQ ID NO:20 residues 23-508 or 23-507). The latter 3 were direct-labeled with Zenon-PE murine IgG labeling kit (Invitrogen). 100,000 hPVR-expressing or negative control cells per well were plated in a 96-well U-bottom plate. The plate was centrifuged for 5 minutes at 300×g at RT and supernatant removed. Cells were resuspended in 100 μl Staining Media (PBS, 1% (v/v) FBS, 0.05% (w/v) sodium azide) with a titration of the above proteins beginning at 5 μg/mL and titered with three-fold serial dilutions down to 0.06 μg for a 6-point curve including the zero control. Proteins/cells were incubated for 1 hour on ice and then the cells were washed with 150 μl Staining Media for a total of 3 washes. Following the final wash, the cells were resuspended in 150 μl of a 1:1 mixture of Staining Media:Cytofix (Becton Dickenson). Cells were analyzed by flow cytometry on a LSR II instrument (Becton Dickenson). All data points were run in triplicate. All hB7R1-containing proteins showed dose dependant binding to hPVR expressing P815 cells. There was no binding to the negative control cells.

Example 12

Competition Assay for Human B7R1Constructs

A cell-based assay to measure competitive binding of human B7R1-containing constructs was established. 100,000 of the previously-described hPVR-expressing P815 cells were plated out per well in a 96-well U-bottom plate. The plate was centrifuged for 5 minutes at 300×g at RT and supernatant removed. Cells were resuspended in 50 μl Staining Media (PBS, 1% (v/v) FBS, 0.05% (w/v) sodium azide) containing a 1:100 dilution of commercially available “Fc-block” (Becton Dickenson) to minimize background binding. Following a 10 min incubation on ice, 50 μl of Staining Media containing a titration of human B7r1-containing proteins was added at “3X” concentration which was a titration from 30 μg/mL down to 0.042 μg/mL. Immediately following this addition, 50 μl of Staining Media containing 3 μg/mL A1476-Alexa Fluor 647 (hB7r1-Fc2 directly labeled with Alexa Fluor 647 through amine conjugation) was added to each well mixed by gentle pipetting. Staining proceeded for 1 hour on ice. Following incubation, the cells were washed with 150 μl Staining Media for a total of 3 washes. Following the final wash, the cells were resuspended in 150 μl of a 1:1 mixture of Staining Media:Cytofix (Becton Dickenson). Cells were analyzed by flow cytometry on a LSR II instrument (Becton Dickenson). All data points were run in triplicate and EC50s were calculated using a 4-parameter non-linear regression curve fit with GraphPad Prism software.

All hB7R1-containing proteins—B7R1-VASP (SEQ ID NO:81); B7R1-Fc2 dimer (SEQ ID NO:79); B7R1[G25-P141][C69Y]-Barbell (SEQ ID NO:18 residues 23-493); and B7R1[G25-P141][C69Y]-Tandem (SEQ ID NO:20 residues 23-508 or 23-507)—showed dose-dependent competition for labeled hB7R1-Fc2 binding. There was no binding to “WT” P815 cells that are negative for hPVR expression. IC50s from two different experiments are shown in Table 4 below.

TABLE 4

Competition for B7R1-Fc2 Bindng to PVR P815 Cells

| | B7R1-Fc2 | B7R1-VASP | B7R1[G25-P141] [C69Y]-Barbell | B7R1[G25-P141] [C69Y]-Tandem |
|---|---|---|---|---|
| Experiment 1 IC50 (g/mL) (Protein Lot) | 1.264 (A2648F) | 0.03694 (A1990F) | 0.1158 (A2751F) | 0.4465 (A2752F) |
| Experiment 2 IC50 (g/mL) (Protein Lot) | ND | 0.01424 (A1990F) | 0.06156 (A2783F) | 0.01294 (A2784F) |

Example 13

Biological Activity of Human B7R1Tandem and Barbell Proteins

T cells are normally activated by T cell antigen receptor (TCR) engagement by MHC molecules plus foreign peptides presented by antigen presenting cells (APC’s). Professional APC’s also express a number of co-stimulatory molecules that engage other receptors on the T cells and contribute to activation. This process can be mimicked by Fc-receptor expressing cells “presenting” antibodies to the TCR/CD3 complex. The presentation of co-stimulatory molecules can then be controlled somewhat by providing selected molecules by transfection of the Fc-receptor expressing cells. We use the mouse mastocytoma cell line P815, which expresses Fc-receptors and cross-links anti-CD3 antibodies effectively. Wild-type P815 cells plus anti-CD3 antibodies can stimulate human T cells, but the level of stimulation is augmented if the P815 cells also express PVR(CD155) because the PVR engages CD226 (DNAM-1) on the T cells delivering a co-stimulatory signal. Soluble B7R1 inhibits this interaction and blocks the CD226-mediated co-stimulation signal.

Human T-cells were isolated from peripheral blood by negative selection (Pan T cell Isolation Kit, Miltenyi Biotec, Auburn, Calif.) and labeled with CFSE (Invitrogen, Carlsbad, Calif.). T-cells were plated into each well of a 96 well plate at 100,000 cells per well, in growth media (RPMI 1640 media, L-glutamine, 10% FBS, NEAA, HEPES, Pen-Strep; Invitrogen, Carlsbad, Calif.). Wells were set up in triplicates with and without the following additional reagents: P815 cells at 50,000 cells per well or P815 cells transfected with and stably expressing full length human PVR (P815/PVR) at 50,000 cells per well, anti-CD3 at 50 ng/ml (BD Bioscience, San Diego, Calif.), B7R1 fusion proteins at 0.6-5 g/ml. In this system, Fc-receptors on the P815 cells cross-link agonistic anti-CD3 Mabs for T cells to provide a primary, sub-optimal stimulation through the T cell receptor (TCR) and PVR co-stimulates through engagement of CD226. The addition of soluble B7R1 should inhibit the co-stimulation by binding to PVR and blocking CD226 activation. Samples were incubated at 37° C. for 4 days, harvested, and stained with fluorochrome conjugated anti-CD4 and anti-CD8 (BD Bioscience, San Diego, Calif.), following typical staining protocols. T cells were analyzed by flow cytometry (LSRII, BD Bioscience, San Diego, Calif.) and cell proliferation measured by CFSE dilution. Effects on CD4 and CD8 T cells were monitored independently by gating these specific populations.

In this example, two tetrameric forms of the protein were tested and compared with an Fc-dimeric protein including the following protein lots:

B7r1(G25-P141) C69Y Fc5 barbell (SEQ ID NO:18 residues 23-493); also referred to herein as B7R1[G25-P141][C69Y]-Barbell; see Example 7);

B7r1(G25-P141) C69Y Fc5 tandem (SEQ ID NO:20 residues 23-508 or 23-507); also referred to herein as B7R1 [G25-P141][C69Y]-Tandem; see Example 8); and B7r1(G25-P141) C69Y Fc5 (bivalent dimer) (SEQ ID NO:80).

FIGS. 3A-3F indicate the level of T cell inhibition induced by soluble B7R1 proteins as measured by reduced proliferative activity. There was relatively little inhibition by the B7R1-Fc5 protein. In contrast, both the tandem and barbell proteins induced significant inhibition across all dose ranges for all three blood donors and for both $CD4^+$ and $CD8^+$ T cell types, with the tandem showing slightly more activity than the barbell. This indicates that these proteins were effective inhibitors of T cell proliferation in vitro and were superior to the dimeric form and further suggests that they should also be superior to the bivalent dimer in a clinical setting.

Example 14

Soluble B7R1Receptor (Barbell Construct) Decreases Disease Incidence and Progression in Mouse Experimental Allergic Encephalomyelitis (EAE) Model of Multiple Sclerosis A) Mouse Allergic Encephalomyelitis (EAE) Model To study mechanism and evaluate the effects of potential therapies for multiple sclerosis, the animal model of experimental autoimmune encephalomyelitis (EAE) is commonly used. For the chronic progressive EAE model, 8 to 10 week old female C57BL/6 mice (Charles River Laboratories) were immunized subcutaneously with myelin oligodendrocyte glycoprotein (MOG) 35-55 peptide emulsified in complete Freund's adjuvant on day 0, followed by intraperitoneal delivery of pertussis toxin on day 0 and intravenous pertussis toxin on day 2. Within approximately 8 to 23 days, animals begin to show symptoms of weight loss and paralysis that are characteristic of this model. The extent of disease is evaluated daily in the mice by taking their body weights and assigning a clinical score (0-8) to each mouse, as detailed below. The typical pattern of disease symptoms in immunized, but otherwise untreated mice, is one of weight loss and paralysis.

Soluble B7R1 receptor barbell construct (mB7R1-Barbell; residues 26-489 of SEQ ID NO:10), dimeric murine Fc2 construct (SEQ ID NO:34), VASP construct (SEQ ID NO:35), or vehicle (PBS) were administered to the mice beginning on day −1. The treatments were delivered as intraperitoneal injections every other day, with each of the B7R1 molecules being administered at 150 μg per mouse per dose.

They could also be delivered using a similar dosing regimen or other route of administration.

B) Monitoring Disease

Animals can begin to show signs of paralysis and weight loss between approximately 8 and 23 days following MOG35-55 immunizations. Most animals develop symptoms within 11-17 days of the immunizations, but some may show symptoms sooner or later than this.

All animals were observed, weighed, and assigned a clinical score daily to assess the status of disease.

C) Clinical Score

0=Normal; healthy.
1=slight tail weakness (tip of tail does not curl and)
2=tail paralysis (unable to hold tail upright)
3=tail paralysis and mild waddle
4=tail paralysis and severe waddle
5=tail paralysis and paralysis of one limb
6=tail paralysis and paralysis of any 2 limbs
7=tetraparesis (all 4 limbs paralysed)
8=moribund or dead Blood was collected during the experiment and at the end to monitor serum levels of cytokine and levels of other mediators of disease. At the time of euthanasia, blood was collected for serum.

D) Results

Figure 4:
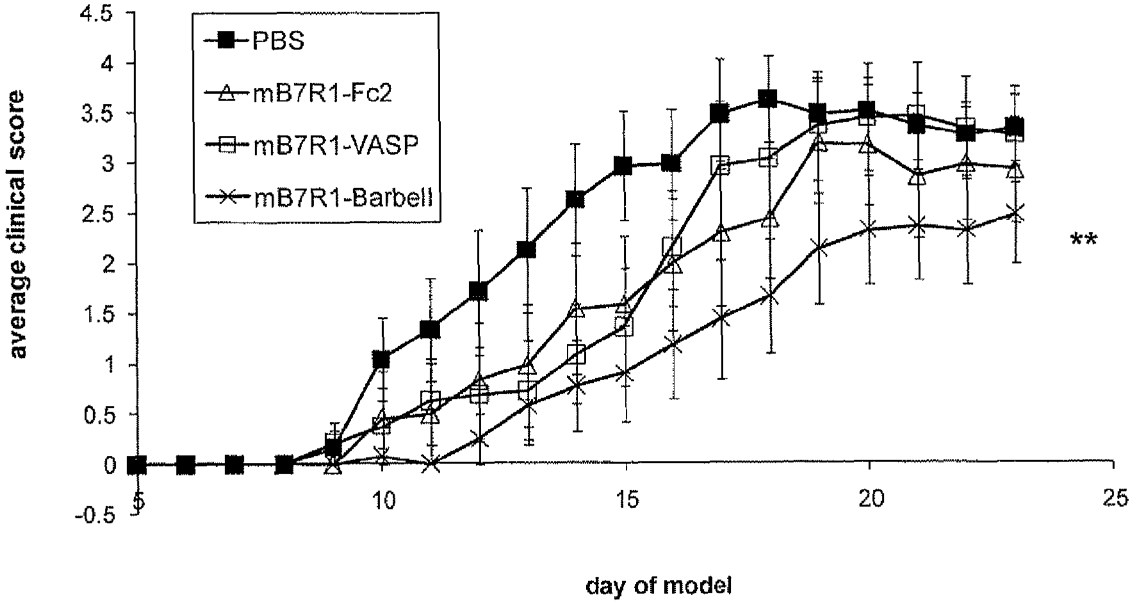
FIG. 4 depicts reduction in experimental allergic encephalomyelitis (EAE) disease scores by treatment with mB7R1-Barbell. EAE was established in mice as described in Example 14, infra. Mice were treated with either vehicle alone (PBS), or vehicle containing soluble B7R1 barbell construct (mB7R1-Barbell), dimeric murine Fc2 construct (mB7R1-Fc2), or VASP construct (mB7R1-VASP). (See Example 14.) Each point represents the mean±SEM for n=10-12 mice per group. Disease scores for the B7R1-Barbell-treated group were different than those for the PBS-treated control group, **p<0.05 by repeated measures ANOVA.

Groups of mice (n=10-12 each) receiving mB7R1-Barbell were characterized by a significant ($p<0.05$) reduction in disease severity over time as evidenced by significant ($p<0.05$) reductions in clinical score compared to mice treated with vehicle (PBS), as analyzed by repeated measures, two-way analysis of variance (ANOVA) (see FIG. 4). There were trends for the groups of mice treated with the dimeric murine Fc2 or VASP constructs to be somewhat protected from disease as shown by the delay in disease progression. However, the differences between these 2 groups and the vehicle-treated group were not significantly different by two-way ANOVA. When analyzed as a sum of disease scores over time (similar to the Area Under The Curve calculation or "disease exposure"), mice treated with the B7R1-Barbell construct had a significantly lower average "disease exposure" index than mice treated with PBS (−2.3 fold lower cumulative score; $p<0.05$). Groups of mice treated with the dimeric murine Fc2 or VASP constructs each had ~25% lower cumulative scores than the PBS-treated group, but the differences were not statistically different. Mice treated with the B7R1-Barbell construct and the dimeric murine Fc2 construct each had a lower incidence of disease onset, such that ~25% of both the B7R1-Barbell- and dimeric murine Fc2-treated groups of mice were protected from disease, ~17% of the VASP-treated mice were protected from disease, and only ~8% of PBS-treated mice were protected. Furthermore, the average day of disease onset for mice receiving B7R1-Barbell was 19 days, 17.6 days for the dimeric murine Fc2-treated mice, and 16.5 days for the VASP-treated mice, whereas the average day of disease onset for PBS-treated mice was shorter (13.7 day), indicating that disease onset was delayed with the soluble B7R1 molecules, especially with the B7R1-Barbell treatment.

Taken together, these results indicate that in vivo administration of B7R1-Barbell was efficacious in reducing disease onset and severity in EAE, a model of human multiple sclerosis. There were trends for efficacy observed with the other soluble B7R1 molecules, though the Barbell construct was the only soluble receptor to show statistically significant differences in this experiment. These results suggest that a soluble B7R1 barbell construct is efficacious in treating human multiple sclerosis.

Example 15

B7R1Tandem Construct Decreases Disease Incidence and Progression in Relapsing-Remitting (RR) Mouse Experimental Allergic Encephalomyelitis (EAE) as a Model of Multiple Sclerosis A) Mouse Allergic Encephalomyelitis (EAE) Model To study mechanism and evaluate the effects of potential therapies for multiple sclerosis, the animal model of experimental autoimmune encephalomyelitis (EAE) is commonly used. For the relapsing-remitting EAE model, 9 to 10 week old female SJL mice (Jackson or Charles River Labs) were immunized subcutaneously with proteolipid peptide (PLP) emulsified in complete Freund's adjuvant, without intravenous pertussis toxin. Within approximately 14 to 18 days, animals began to show symptoms of weight loss and paralysis that are characteristic of this model. The extent of disease was evaluated daily in the mice by taking their body weights and assigning a clinical score (0-8) to each mouse, as detailed below. The typical pattern of disease symptoms in immunized, but otherwise untreated mice, is one of weight loss and paralysis, followed by a period of disease symptom remission, and a subsequent relapse of disease symptoms. A pattern of relapses and remissions of disease symptoms ensues, which is also found in humans with this type of multiple sclerosis, known as relapsing-remitting disease.

Soluble B7R1 receptor tandem construct (mB7R1-Tandem; residues 26-504 or 26-503 of SEQ ID NO:12), soluble B7R1 receptor barbell construct (mB7R1-Barbell; residues 26-489 of SEQ ID NO:10), vehicle (PBS), or a clinically relevant positive control (murine-specific CTLA4-Ig) were administered in a therapeutic dosing regime, such that they started treatments on the second day after they had gone through their first peak of disease. The treatments were delivered as intraperitoneal injections every other day, with the mB7R1-Tandem, mB7R1-Barbell, and mCTLA4-Ig molecules being administered at 150 μg per mouse per dose. They could also be delivered using a similar dosing regimen or other route of administration.

B) Monitoring Disease

Animals can begin to show signs of paralysis and weight loss between approximately 8 and 23 days following PLP immunizations. Most animals in this experiment developed symptoms within 14-18 days of the immunizations.

All animals were observed, weighed, and assigned a clinical score daily to assess the status of disease.

C) Clinical Score

0=Normal; healthy.

1=slight tail weakness (tip of tail does not curl and)

2=tail paralysis (unable to hold tail upright)

3=tail paralysis and mild waddle

4=tail paralysis and severe waddle

5=tail paralysis and paralysis of one limb

6=tail paralysis and paralysis of any 2 limbs

7=tetraparesis (all 4 limbs paralysed)

8=moribund or dead

D) Results

Groups of mice (n=12-13 each) that were treated with B7R1-Tandem were characterized by a significant ($p<0.05$) reduction in disease severity into the remission phase, as evidenced by significant ($p<0.05$) reductions in clinical score and body weight loss compared to mice treated with vehicle (PBS). Furthermore, the mice treated with B7R1-Tandem had a significantly lower ($p<0.05$) incidence of disease relapse compared to vehicle (PBS)-treated mice. This is a very important finding since disease relapse is a hallmark of this disease model and of relapsing-remitting MS in humans. The group of mice treated with the B7R1-Barbell molecule had disease scores and relapse rates similar to the group of mice treated with the positive control, mCTLA4-Ig. Neither the B7R1-Barbell nor mCTLA4-Ig treated groups of mice had significantly different disease scores or relapse rates compared to the PBS-treated group of mice.

Taken together, these results indicate that in vivo administration of B7R1-Tandem can be efficacious in reducing disease onset and severity in PLP EAE, a model of human relapsing-remitting multiple sclerosis. These results suggest that a soluble B7R1-Tandem construct is efficacious in treating human multiple sclerosis.

Example 16

B7R1-Tandem Decreases Disease Incidence and Progression in a Mouse Model of T-cell Adoptive Transfer Colitis and Psoriasis T-cell Adoptive Transfer Colitis Model Adoptive transfer of naive T cells into minor histocompatibility mismatched or syngeneic immunocompromised mice leads to development of colitis (Leach et al., 1996; Powrie et al., 1997) as well as skin lesions resembling psoriasis (Schon et al., 1997; Davenport et al., 2002). Transplantation of as low as 0.2 million CD4+ CD25− T cells from BALB/C or B10.D2 mice into immunocompromised C.B-17 SCID mice results in weight loss, hemoccult positive stool and development of skin lesions. The symptoms in these mice vary from colony to colony.

This model of colitis/psoriasis has some similarities to human Crohn's disease and psoriasis, and has been used extensively to test efficacy of therapeutics for these diseases in humans. For this experiment, mice (5 B10.D2 female mice donors; 20 C.B-17 SCID female recipients) are obtained from Jackson Laboratories or Charles River Laboratories, respectively. Spleens from 5 B10.D2 mice are collected. CD4+ CD25− T-cell are isolated from pooled spleens using standard methodology known to the art. Purity of T-cells are evaluated by flow cytometry.

C.B-17 SCID mice receive 5×105-10×105 CD4+ CD25− T-cells from spleen via intravenous injection. All mice are weighed at least five times per week and carefully observed for weight loss. Clinical colitis scores (stool consistency and blood in stool) are taken at least one day per week. Mice are also monitored at least 5 days per week and assigned a score for signs and extent of psoriasis (hair loss, scratching, and alopecia).

Soluble B7R1 receptor tandem construct (B7R1-Tandem) or vehicle (PBS) are administered to the mice beginning on day 0 (day of cell transfer). The treatments are delivered as intraperitoneal injections every other day, with B7R1-Tandem being administered at 150 μg per mouse per dose. They could also be delivered using a similar dosing regimen or other route of administration.

At the end of the study, tissue samples (intestine and skin, for example) are submitted for histological evidence of colitis and psoriasis, respectively, and serum collected for analysis of cytokine and chemokine levels.

Results

Groups of mice (n=10 each) receiving B7R1-Tandem are characterized by a significant ($p<0.05$) reduction in disease severity as evidenced by significant ($p<0.05$) reductions in clinical scores of colitis and psoriasis, and body weight loss compared to mice treated with vehicle (PBS). Furthermore, the mice treated with B7R1-Tandem have less pathologic/histologic evidence of colitis and psoriasis compared to vehicle (PBS)-treated mice.

Taken together, these results indicate that in vivo administration of B7R1-Tandem can be efficacious in reducing colitis and psoriasis in a murine T cell transfer model, and suggest that this soluble receptor may be efficacious in treating human inflammatory bowel disease and/or psoriasis.

Example 17

B7R1Soluble Receptors (Barbell and Tandem Constructs) Decrease Disease Incidence and Progression in Mouse Collagen Induced Arthritis (CIA) Model A) Mouse Collagen Induced Arthritis (CIA) Model Ten-week old male DBA/1J mice (Jackson Labs) were divided into 3 groups of 15 mice/group, designated for prophylactic dosing of PBS, B7R1 barbell protein, or B7R1 tandem protein. On day-21, all animals were given an intradermal tail injection of 50-100 µL of 1 mg/mL chick Type II collagen formulated in Complete Freund's Adjuvant (prepared by Chondrex, Redmond, Wash.), and three weeks later on Day 0 they were given the same injection except prepared in Incomplete Freund's Adjuvant. B7R1-Barbell (mB7R1-Barbell; residues 26-489 of SEQ ID NO:10), B7R1-Tandem (mB7R1-Tandem; residues 26-504 or 26-503 of SEQ ID NO:12), B7R1-VASP (mB7R1-VASP; SEQ ID NO:35), or vehicle (PBS) were administered as intraperitoneal injections every other day for 3 weeks starting on Day −1. Groups received 150 µg of B7R1-Barbell or B7R1-Tandem protein per animal per dose, and control groups received the vehicle control, PBS (Life Technologies, Rockville, Md.). Animals began to show symptoms of arthritis following the second collagen injection, with most animals developing inflammation within 1-2 weeks. The extent of disease was evaluated in each paw by using a caliper to measure paw thickness, and by assigning a clinical score (0-3) to each paw (see below).

B) Monitoring Disease

Animals can begin to show signs of paw inflammation soon after the second collagen injection, and some animals may even begin to have signs of toe inflammation prior to the second collagen injection. Most animals develop arthritis within 1-2 weeks of the boost injection, but some may require a longer period of time. Incidence of disease in this model is typically 90-100%, and 0-5 non-responders (determined after 6 weeks of observation) are typically seen in a study using 60 animals.

All animals were observed daily to assess the status of the disease in their paws, which is done by assigning a qualitative clinical score to each of the paws. Every day, each animal had its 4 paws scored according to its state of clinical disease. To to determine the clinical score, the paw can be thought of as having 3 zones, the toes, the paw itself (manus or pes), and the wrist or ankle joint. The extent and severity of the inflammation relative to these zones is noted including: observation of each toe for swelling; torn nails or redness of toes; notation of any evidence of edema or redness in any of the paws; notation of any loss of fine anatomic demarcation of tendons or bones; evaluation of the wrist or ankle for any edema or redness; and notation if the inflammation extends proximally up the leg. A paw score of 1, 2, or 3 was based first on the overall impression of severity, and second on how many zones are involved. The scale used for clinical scoring is shown below.

C) Clinical Score

0=Normal 0.5=One or more toes involved, but only the toes are inflamed

1=mild inflammation involving the paw (1 zone), and may include a toe or toes

2=moderate inflammation in the paw and may include some of the toes and/or the wrist/ankle (2 zones)

3=severe inflammation in the paw, wrist/ankle, and some or all of the toes (3 zones).

Blood was collected at the end of the experiment to monitor serum levels of anti-collagen antibodies, as well as serum chemokine and cytokine levels.

Figure 5:
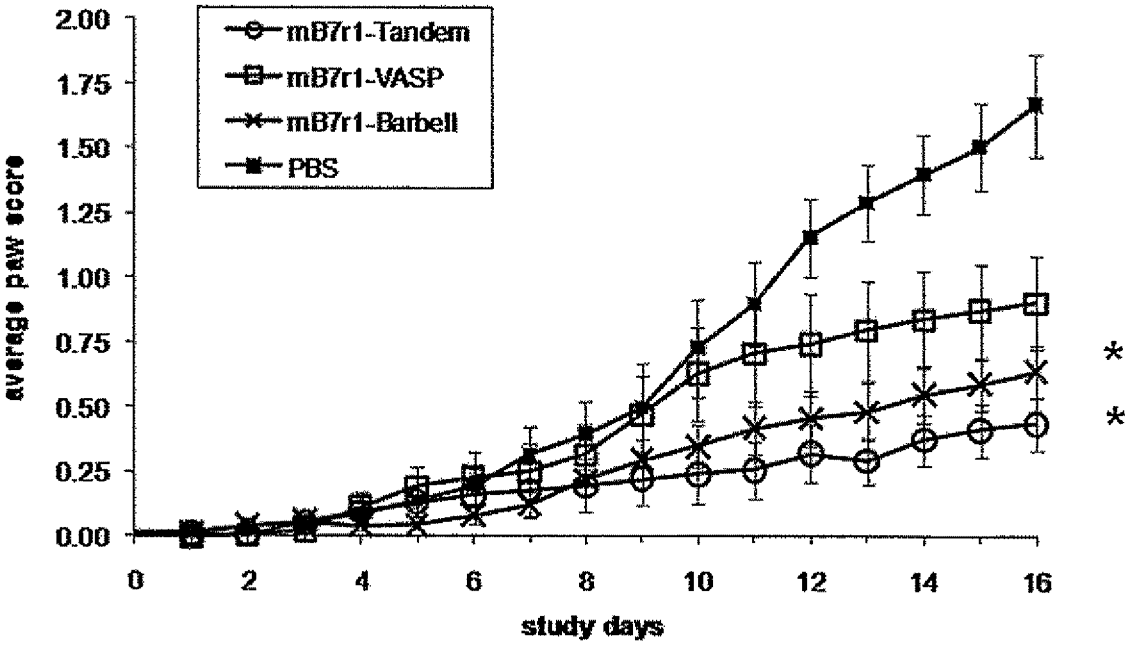
FIG. 5 depicts reduction in arthritis disease score by treatment with mB7R1-Barbell and mB7R1-Tandem. Collagen-induced arthritis (CIA) was established in mice as described in Example 17, infra. Mice were treated with either vehicle alone (PBS), or vehicle containing soluble B7R1 barbell construct (mB7R1-Barbell), tandem construct (mB7R1-Tandem), or VASP construct (mB7R1-VASP). (See Example 17.) Each point represents the mean±SEM for n=15 mice per group. Disease scores (paw thickness) for the B7R1-Barbell- and B7R1-Tandem-treated groups were different than those for the PBS-treated control group, *p<0.05 by two-way ANOVA.

Groups of mice receiving B7R1-Barbell and B7R1-Tandem molecules were characterized by significantly less arthritis and paw inflammation over the course of the experiment, compared to mice receiving PBS ($p<0.05$) (see FIG. 5). Furthermore, mice receiving B7R1-Tandem tended to have even less arthritis and paw inflammation over the course of the experiment compared to mice receiving the B7R1-VASP protein ($p=0.09$). Serum levels of IL-6 and the chemokines MCP-1, IP-1, and KC were lower in mice treated with the B7R1-Barbell and B7R1-Tandem molecules compared to PBS-treated mice. There were no significant differences in serum levels of anti-collagen antibodies between groups. These results indicated that B7R1-Barbell and B7R1-Tandem can reduce inflammation, as well as disease progression associated with this model of arthritis and suggest that B7R1 barbell or tandem constructs of B7R1 soluble receptors may be efficacious in the treatment of human arthritis.

From the foregoing, it will be appreciated that, although specific embodiments of the invention have been described herein for purposes of illustration, various modifications may be made without deviating from the spirit and scope of the invention. Accordingly, the invention is not limited except as by the appended claims. All publications, patents, and patent applications cited herein are hereby incorporated by reference in their entireties for all purposes.

What is claimed is:

1. A soluble fusion polypeptide comprising, from amino terminus to carboxyl terminus, P1-L1-D-L2-P2 wherein:

P1 is a first polypeptide having at least 95% identity with amino acid residues 25-141 of SEQ ID NO:2;

L1 is a first polypeptide linker;

D is a dimerizing domain;

L2 is a second polypeptide linker;

P2 is a second polypeptide having at least 95% identity with amino acid residues 25-141 of SEQ ID NO:2;

wherein said fusion polypeptide is capable of specifically binding to the extracellular domain of CD155 (amino acid residues 28-343 of SEQ ID NO:22).

2. A soluble fusion polypeptide comprising, from amino terminus to carboxyl terminus, P2-L2-P1-L1-D wherein:

P1 is a first polypeptide having at least 95% identity with amino acid residues 25-141 of SEQ ID NO:2;

L1 is a first polypeptide linker;

D is a dimerizing domain;

L2 is a second polypeptide linker;

P2 is a second polypeptide having at least 95% identity with amino acid residues 25-141 of SEQ ID NO:2;

wherein said fusion polypeptide is capable of specifically binding to the extracellular domain of CD155 (amino acid residues 28-343 of SEQ ID NO:22).

3. The fusion polypeptide of claim 1 or 2, wherein at least one of P1 and P2 has 100% identity with amino acid residues 25-141 of SEQ ID NO:2.

4. The fusion polypeptide of claim 1 or 2, wherein at least one of P1 and P2 has the amino acid sequence shown in residues 23-139 of SEQ ID NO: 18.

5. The fusion polypeptide of claim 1 or 2 wherein D is an immunoglobulin heavy chain constant region.

6. The fusion polypeptide of claim 1 or 2, wherein L1 consists of from 15 to 32 amino acid residues, wherein from 1 to 8 of said residues are cysteine residues.

7. The fusion polypeptide of claim 1 or 2, wherein L2 comprises a plurality of glycine residues and optionally comprises at least one serine residue.

8. The fusion polypeptide of claim 1 or 2, wherein L2 comprises the amino acid sequence shown in SEQ ID NO: 25.

9. The fusion polypeptide of claim 1, wherein said fusion polypeptide comprises the amino acid sequence shown in residues 23-493 of SEQ ID NO: 18.

10. The fusion polypeptide of claim 2, wherein said fusion polypeptide comprises the amino acid sequence shown in residues 23-508 or 23-507 of SEQ ID NO:20.

11. A polynucleotide encoding the fusion polypeptide of claim 1 or 2.

12. An expression vector comprising the following operably linked elements:

a transcription promoter;

a DNA segment encoding the fusion polypeptide of claim 1 or 2 and a transcription terminator.

13. A cultured cell into which has been introduced the expression vector of claim 12, wherein the cell expresses the DNA segment.

14. A method of making a fusion polypeptide, the method comprising:

culturing a cell into which has been introduced the expression vector of claim 12, wherein the cell expresses the DNA segment and the encoded fusion polypeptide is produced; and recovering the fusion polypeptide.

15. A composition comprising:

a fusion polypeptide of claim 1 or 2; and a pharmaceutically acceptable carrier.

* * * * *

SEQUENCE LISTING

```
<160> NUMBER OF SEQ ID NOS: 81

<210> SEQ ID NO 1
<211> LENGTH: 735
<212> TYPE: DNA
<213> ORGANISM: Homo sapiens
<220> FEATURE:
<221> NAME/KEY: misc_feature
<222> LOCATION: (349)..(349)
<223> OTHER INFORMATION: n is a, c, g, or t
```

-continued

<400> SEQUENCE: 1

```
atgcgctggt gtctcctcct gatctgggcc caggggctga ggcaggctcc cctcgcctca     60
ggaatgatga caggcacaat agaaacaacg gggaacattt ctgcagagaa aggtggctct    120
atcatcttac aatgtcacct ctcctccacc acggcacaag tgacccaggt caactgggag    180
cagcaggacc agcttctggc catttgtaat gctgacttgg ggtggcacat ctccccatcc    240
ttcaaggatc gagtggcccc aggtcccggc ctgggcctca ccctccagtc gctgaccgtg    300
aacgatacag gggagtactt ctgcatctat cacacctacc ctgatgggnc gtacactggg    360
agaatcttcc tggaggtcct agaaagctca gtggctgagc acggtgccag gttccagatt    420
ccattgcttg gagccatggc cgcgacgctg gtggtcatct gcacagcagt catcgtggtg    480
gtcgcgttga ctagaaagaa gaaagccctc agaatccatt ctgtggaagg tgacctcagg    540
agaaaatcag ctggacagga ggaatggagc cccagtgctc cctcaccccc aggaagctgt    600
gtccaggcag aagctgcacc tgctgggctc tgtggagagc agcggggaga ggactgtgcc    660
gagctgcatg actacttcaa tgtcctgagt tacagaagcc tgggtaactg cagcttcttc    720
acagagactg gttag                                                     735
```

<210> SEQ ID NO 2
<211> LENGTH: 244
<212> TYPE: PRT
<213> ORGANISM: Homo sapiens
<220> FEATURE:
<221> NAME/KEY: misc_feature
<222> LOCATION: (117)..(117)
<223> OTHER INFORMATION: Xaa is Thr or Ala

<400> SEQUENCE: 2

```
Met Arg Trp Cys Leu Leu Leu Ile Trp Ala Gln Gly Leu Arg Gln Ala
1               5                   10                  15

Pro Leu Ala Ser Gly Met Met Thr Gly Thr Ile Glu Thr Thr Gly Asn
            20                  25                  30

Ile Ser Ala Glu Lys Gly Gly Ser Ile Ile Leu Gln Cys His Leu Ser
        35                  40                  45

Ser Thr Thr Ala Gln Val Thr Gln Val Asn Trp Glu Gln Gln Asp Gln
    50                  55                  60

Leu Leu Ala Ile Cys Asn Ala Asp Leu Gly Trp His Ile Ser Pro Ser
65                  70                  75                  80

Phe Lys Asp Arg Val Ala Pro Gly Pro Gly Leu Gly Leu Thr Leu Gln
                85                  90                  95

Ser Leu Thr Val Asn Asp Thr Gly Glu Tyr Phe Cys Ile Tyr His Thr
            100                 105                 110

Tyr Pro Asp Gly Xaa Tyr Thr Gly Arg Ile Phe Leu Glu Val Leu Glu
        115                 120                 125

Ser Ser Val Ala Glu His Gly Ala Arg Phe Gln Ile Pro Leu Leu Gly
    130                 135                 140

Ala Met Ala Ala Thr Leu Val Val Ile Cys Thr Ala Val Ile Val Val
145                 150                 155                 160

Val Ala Leu Thr Arg Lys Lys Lys Ala Leu Arg Ile His Ser Val Glu
                165                 170                 175

Gly Asp Leu Arg Arg Lys Ser Ala Gly Gln Glu Glu Trp Ser Pro Ser
            180                 185                 190

Ala Pro Ser Pro Pro Gly Ser Cys Val Gln Ala Glu Ala Ala Pro Ala
        195                 200                 205
```

-continued

```
Gly Leu Cys Gly Glu Gln Arg Gly Glu Asp Cys Ala Glu Leu His Asp
    210                 215                 220

Tyr Phe Asn Val Leu Ser Tyr Arg Ser Leu Gly Asn Cys Ser Phe Phe
225                 230                 235                 240

Thr Glu Thr Gly


<210> SEQ ID NO 3
<211> LENGTH: 726
<212> TYPE: DNA
<213> ORGANISM: Mus musculus

<400> SEQUENCE: 3

atgcatggct ggctgctcct ggtctgggtc caggggctga tacaggctgc cttcctcgct      60

acaggagcca cagcaggcac gatagataca aagaggaaca tctctgcaga ggaaggtggc     120

tctgtcatct tacagtgtca cttctcctct gacacagctg aagtgaccca agtcgactgg     180

aagcagcagg accagcttct ggccatttat agtgttgacc tggggtggca tgtcgcttca     240

gtcttcagtg atcgggtggt cccaggcccc agcctaggcc tcaccttcca gtctctgaca     300

atgaatgaca cgggagagta cttctgtacc tatcatacgt atcctggtgg gatttacaag     360

gggagaatat tcctgaaggt ccaagaaagc tcagtggctc agttccagac tgccccgctt     420

ggaggaacca tggctgctgt gctgggactc atttgcttaa tggtcacagg agtgactgta     480

ctggctagaa agaagtctat tagaatgcat tctatagaaa gtggccttgg gagaacagaa     540

gcggagccac aggaatggaa cctgaggagt ctctcatccc ctggaagccc tgtccagaca     600

caaactgccc ctgctggtcc ctgtggagag caggcagaag atgactatgc tgacccacag     660

gaatacttta atgtcctgag ctacagaagc ctagagagct tcattgctgt atcgaagact     720

ggctaa                                                                726


<210> SEQ ID NO 4
<211> LENGTH: 241
<212> TYPE: PRT
<213> ORGANISM: Mus musculus

<400> SEQUENCE: 4

Met His Gly Trp Leu Leu Leu Val Trp Val Gln Gly Leu Ile Gln Ala
1               5                   10                  15

Ala Phe Leu Ala Thr Gly Ala Thr Ala Gly Thr Ile Asp Thr Lys Arg
            20                  25                  30

Asn Ile Ser Ala Glu Glu Gly Gly Ser Val Ile Leu Gln Cys His Phe
        35                  40                  45

Ser Ser Asp Thr Ala Glu Val Thr Gln Val Asp Trp Lys Gln Gln Asp
    50                  55                  60

Gln Leu Leu Ala Ile Tyr Ser Val Asp Leu Gly Trp His Val Ala Ser
65                  70                  75                  80

Val Phe Ser Asp Arg Val Val Pro Gly Pro Ser Leu Gly Leu Thr Phe
                85                  90                  95

Gln Ser Leu Thr Met Asn Asp Thr Gly Glu Tyr Phe Cys Thr Tyr His
            100                 105                 110

Thr Tyr Pro Gly Gly Ile Tyr Lys Gly Arg Ile Phe Leu Lys Val Gln
        115                 120                 125

Glu Ser Ser Val Ala Gln Phe Gln Thr Ala Pro Leu Gly Gly Thr Met
    130                 135                 140

Ala Ala Val Leu Gly Leu Ile Cys Leu Met Val Thr Gly Val Thr Val
145                 150                 155                 160
```

-continued

```
Leu Ala Arg Lys Lys Ser Ile Arg Met His Ser Ile Glu Ser Gly Leu
                165                 170                 175

Gly Arg Thr Glu Ala Glu Pro Gln Glu Trp Asn Leu Arg Ser Leu Ser
            180                 185                 190

Ser Pro Gly Ser Pro Val Gln Thr Gln Thr Ala Pro Ala Gly Pro Cys
        195                 200                 205

Gly Glu Gln Ala Glu Asp Asp Tyr Ala Asp Pro Gln Glu Tyr Phe Asn
    210                 215                 220

Val Leu Ser Tyr Arg Ser Leu Glu Ser Phe Ile Ala Val Ser Lys Thr
225                 230                 235                 240

Gly


<210> SEQ ID NO 5
<211> LENGTH: 1494
<212> TYPE: DNA
<213> ORGANISM: Artificial
<220> FEATURE:
<223> OTHER INFORMATION: B7R1 Fc5 Barbell

<400> SEQUENCE: 5

atgcgctggt gtctcctcct gatctgggcc caggggctga ggcaggctcc cctcgcctca      60

ggaatgatga caggcacaat agaaacaacg gggaacattt ctgcagagaa aggtggctct     120

atcatcttac aatgtcacct ctcctccacc acggcacaag tgacccaggt caactgggag     180

cagcaggacc agcttctggc catttgtaat gctgacttgg ggtggcacat ctccccatcc     240

ttcaaggatc gagtggcccc aggtcccggc ctgggcctca ccctccagtc gctgaccgtg     300

aacgatacag gggagtactt ctgcatctat cacacctacc ctgatgggac gtacactggg     360

agaatcttcc tggaggtcct agaaagctca gtggctgagc acggtgccag gttccagatt     420

ccagagccca aatcttcaga caaaactcac acatgcccac cgtgcccagc acctgaagcc     480

gagggggcac cgtcagtctt cctcttcccc ccaaaaccca aggacaccct catgatctcc     540

cggacccctg aggtcacatg cgtggtggtg gacgtgagcc acgaagaccc tgaggtcaag     600

ttcaactggt acgtggacgg cgtggaggtg cataatgcca agacaaagcc gcgggaggag     660

cagtacaaca gcacgtaccg tgtggtcagc gtcctcaccg tcctgcacca ggactggctg     720

aatggcaagg agtacaagtg caaggtctcc aacaaagccc tcccatcctc catcgagaaa     780

accatctcca aagccaaagg gcagccccga gagccacagg tgtacaccct gcccccatcc     840

cgggatgagc tgaccaagaa ccaggtcagc ctgacctgcc tggtcaaagg cttctatccc     900

agcgacatcg ccgtggagtg ggagagcaat gggcagccgg agaacaacta caagaccacg     960

cctcccgtgc tggactccga cggctccttc ttcctctaca gcaagctcac cgtggacaag    1020

agcaggtggc agcaggggaa cgtcttctca tgctccgtga tgcatgaggc tctgcacaac    1080

cactacacgc agaagagcct ctccctgtct ccgggtaaag gtggtgggtc cggaatgatg    1140

acaggcacaa tagaaacaac ggggaacatt tctgcagaga aaggtggctc tatcatctta    1200

caatgtcacc tctcctccac cacggcacaa gtgacccagg tcaactggga gcagcaggac    1260

cagcttctgg ccatttgtaa tgctgacttg gggtggcaca tctccccatc cttcaaggat    1320

cgagtggccc caggtcccgg cctgggcctc accctccagt cgctgaccgt gaacgataca    1380

ggggagtact tctgcatcta tcacacctac cctgatggga cgtacactgg gagaatcttc    1440

ctggaggtcc tagaaagctc agtggctgag cacggtgcca ggttccagat tcca          1494
```

<210> SEQ ID NO 6
<211> LENGTH: 498
<212> TYPE: PRT
<213> ORGANISM: Artificial
<220> FEATURE:
<223> OTHER INFORMATION: B7R1 Fc5 Barbell

<400> SEQUENCE: 6

```
Met Arg Trp Cys Leu Leu Leu Ile Trp Ala Gln Gly Leu Arg Gln Ala
1               5                   10                  15

Pro Leu Ala Ser Gly Met Met Thr Gly Thr Ile Glu Thr Thr Gly Asn
            20                  25                  30

Ile Ser Ala Glu Lys Gly Gly Ser Ile Ile Leu Gln Cys His Leu Ser
        35                  40                  45

Ser Thr Thr Ala Gln Val Thr Gln Val Asn Trp Glu Gln Gln Asp Gln
    50                  55                  60

Leu Leu Ala Ile Cys Asn Ala Asp Leu Gly Trp His Ile Ser Pro Ser
65                  70                  75                  80

Phe Lys Asp Arg Val Ala Pro Gly Pro Gly Leu Gly Leu Thr Leu Gln
                85                  90                  95

Ser Leu Thr Val Asn Asp Thr Gly Glu Tyr Phe Cys Ile Tyr His Thr
            100                 105                 110

Tyr Pro Asp Gly Thr Tyr Thr Gly Arg Ile Phe Leu Glu Val Leu Glu
        115                 120                 125

Ser Ser Val Ala Glu His Gly Ala Arg Phe Gln Ile Pro Glu Pro Lys
    130                 135                 140

Ser Ser Asp Lys Thr His Thr Cys Pro Pro Cys Pro Ala Pro Glu Ala
145                 150                 155                 160

Glu Gly Ala Pro Ser Val Phe Leu Phe Pro Pro Lys Pro Lys Asp Thr
                165                 170                 175

Leu Met Ile Ser Arg Thr Pro Glu Val Thr Cys Val Val Val Asp Val
            180                 185                 190

Ser His Glu Asp Pro Glu Val Lys Phe Asn Trp Tyr Val Asp Gly Val
        195                 200                 205

Glu Val His Asn Ala Lys Thr Lys Pro Arg Glu Glu Gln Tyr Asn Ser
    210                 215                 220

Thr Tyr Arg Val Val Ser Val Leu Thr Val Leu His Gln Asp Trp Leu
225                 230                 235                 240

Asn Gly Lys Glu Tyr Lys Cys Lys Val Ser Asn Lys Ala Leu Pro Ser
                245                 250                 255

Ser Ile Glu Lys Thr Ile Ser Lys Ala Lys Gly Gln Pro Arg Glu Pro
            260                 265                 270

Gln Val Tyr Thr Leu Pro Pro Ser Arg Asp Glu Leu Thr Lys Asn Gln
        275                 280                 285

Val Ser Leu Thr Cys Leu Val Lys Gly Phe Tyr Pro Ser Asp Ile Ala
    290                 295                 300

Val Glu Trp Glu Ser Asn Gly Gln Pro Glu Asn Asn Tyr Lys Thr Thr
305                 310                 315                 320

Pro Pro Val Leu Asp Ser Asp Gly Ser Phe Phe Leu Tyr Ser Lys Leu
                325                 330                 335

Thr Val Asp Lys Ser Arg Trp Gln Gln Gly Asn Val Phe Ser Cys Ser
            340                 345                 350

Val Met His Glu Ala Leu His Asn His Tyr Thr Gln Lys Ser Leu Ser
        355                 360                 365

Leu Ser Pro Gly Lys Gly Gly Gly Ser Gly Met Met Thr Gly Thr Ile
```

```
    370                 375                 380

Glu Thr Thr Gly Asn Ile Ser Ala Glu Lys Gly Gly Ser Ile Ile Leu
385                 390                 395                 400

Gln Cys His Leu Ser Ser Thr Thr Ala Gln Val Thr Gln Val Asn Trp
                405                 410                 415

Glu Gln Gln Asp Gln Leu Leu Ala Ile Cys Asn Ala Asp Leu Gly Trp
            420                 425                 430

His Ile Ser Pro Ser Phe Lys Asp Arg Val Ala Pro Gly Pro Gly Leu
        435                 440                 445

Gly Leu Thr Leu Gln Ser Leu Thr Val Asn Asp Thr Gly Glu Tyr Phe
    450                 455                 460

Cys Ile Tyr His Thr Tyr Pro Asp Gly Thr Tyr Thr Gly Arg Ile Phe
465                 470                 475                 480

Leu Glu Val Leu Glu Ser Ser Val Ala Glu His Gly Ala Arg Phe Gln
                485                 490                 495

Ile Pro
```

<210> SEQ ID NO 7
<211> LENGTH: 1539
<212> TYPE: DNA
<213> ORGANISM: Artificial
<220> FEATURE:
<223> OTHER INFORMATION: B7R1 Fc5 Tandem

<400> SEQUENCE: 7

```
atgcgctggt gtctcctcct gatctgggcc caggggctga ggcaggctcc cctcgcctca     60

ggaatgatga caggcacaat agaaacaacg gggaacattt ctgcagagaa aggtggctct    120

atcatcttac aatgtcacct ctcctccacc acggcacaag tgacccaggt caactgggag    180

cagcaggacc agcttctggc catttgtaat gctgacttgg ggtggcacat ctccccatcc    240

ttcaaggatc gagtggcccc aggtcccggc ctgggcctca ccctccagtc gctgaccgtg    300

aacgatacag gggagtactt ctgcatctat cacacctacc ctgatgggac gtacactggg    360

agaatcttcc tggaggtcct agaaagctca gtggctgagc acggtgccag gttccagatt    420

ccaggcggtt cgggctcagg atcgggaggt tcaggttccg gtggttctgg tggtgggtcc    480

ggaatgatga caggcacaat agaaacaacg gggaacattt ctgcagagaa aggtggctct    540

atcatcttac aatgtcacct ctcctccacc acggcacaag tgacccaggt caactgggag    600

cagcaggacc agcttctggc catttgtaat gctgacttgg ggtggcacat ctccccatcc    660

ttcaaggatc gagtggcccc aggtcccggc ctgggcctca ccctccagtc gctgaccgtg    720

aacgatacag gggagtactt ctgcatctat cacacctacc ctgatgggac gtacactggg    780

agaatcttcc tggaggtcct agaaagctca gtggctgagc acggtgccag gttccagatt    840

ccagagccca aatcttcaga caaaactcac acatgcccac cgtgcccagc acctgaagcc    900

gagggggcac cgtcagtctt cctcttcccc ccaaaaccca aggacaccct catgatctcc    960

cggacccctg aggtcacatg cgtggtggtg gacgtgagcc acgaagaccc tgaggtcaag   1020

ttcaactggt acgtggacgg cgtggaggtg cataatgcca agacaaagcc gcgggaggag   1080

cagtacaaca gcacgtaccg tgtggtcagc gtcctcaccg tcctgcacca ggactggctg   1140

aatggcaagg agtacaagtg caaggtctcc aacaaagccc tcccatcctc catcgagaaa   1200

accatctcca aagccaaagg gcagccccga gagccacagg tgtacaccct gcccccatcc   1260

cgggatgagc tgaccaagaa ccaggtcagc ctgacctgcc tggtcaaagg cttctatccc   1320
```

-continued

```
agcgacatcg ccgtggagtg ggagagcaat gggcagccgg agaacaacta caagaccacg   1380

cctcccgtgc tggactccga cggctccttc ttcctctaca gcaagctcac cgtggacaag   1440

agcaggtggc agcaggggaa cgtcttctca tgctccgtga tgcatgaggc tctgcacaac   1500

cactacacgc agaagagcct ctccctgtct ccgggtaaa                          1539


<210> SEQ ID NO 8
<211> LENGTH: 513
<212> TYPE: PRT
<213> ORGANISM: Artificial
<220> FEATURE:
<223> OTHER INFORMATION: B7R1 Fc5 Tandem

<400> SEQUENCE: 8

Met Arg Trp Cys Leu Leu Leu Ile Trp Ala Gln Gly Leu Arg Gln Ala
1               5                   10                  15

Pro Leu Ala Ser Gly Met Met Thr Gly Thr Ile Glu Thr Thr Gly Asn
            20                  25                  30

Ile Ser Ala Glu Lys Gly Gly Ser Ile Ile Leu Gln Cys His Leu Ser
        35                  40                  45

Ser Thr Thr Ala Gln Val Thr Gln Val Asn Trp Glu Gln Gln Asp Gln
    50                  55                  60

Leu Leu Ala Ile Cys Asn Ala Asp Leu Gly Trp His Ile Ser Pro Ser
65                  70                  75                  80

Phe Lys Asp Arg Val Ala Pro Gly Pro Gly Leu Gly Leu Thr Leu Gln
                85                  90                  95

Ser Leu Thr Val Asn Asp Thr Gly Glu Tyr Phe Cys Ile Tyr His Thr
            100                 105                 110

Tyr Pro Asp Gly Thr Tyr Thr Gly Arg Ile Phe Leu Glu Val Leu Glu
        115                 120                 125

Ser Ser Val Ala Glu His Gly Ala Arg Phe Gln Ile Pro Gly Gly Ser
    130                 135                 140

Gly Ser Gly Ser Gly Gly Ser Gly Ser Gly Gly Ser Gly Gly Gly Ser
145                 150                 155                 160

Gly Met Met Thr Gly Thr Ile Glu Thr Thr Gly Asn Ile Ser Ala Glu
                165                 170                 175

Lys Gly Gly Ser Ile Ile Leu Gln Cys His Leu Ser Ser Thr Thr Ala
            180                 185                 190

Gln Val Thr Gln Val Asn Trp Glu Gln Gln Asp Gln Leu Leu Ala Ile
        195                 200                 205

Cys Asn Ala Asp Leu Gly Trp His Ile Ser Pro Ser Phe Lys Asp Arg
    210                 215                 220

Val Ala Pro Gly Pro Gly Leu Gly Leu Thr Leu Gln Ser Leu Thr Val
225                 230                 235                 240

Asn Asp Thr Gly Glu Tyr Phe Cys Ile Tyr His Thr Tyr Pro Asp Gly
                245                 250                 255

Thr Tyr Thr Gly Arg Ile Phe Leu Glu Val Leu Glu Ser Ser Val Ala
            260                 265                 270

Glu His Gly Ala Arg Phe Gln Ile Pro Glu Pro Lys Ser Ser Asp Lys
        275                 280                 285

Thr His Thr Cys Pro Pro Cys Pro Ala Pro Glu Ala Glu Gly Ala Pro
    290                 295                 300

Ser Val Phe Leu Phe Pro Pro Lys Pro Lys Asp Thr Leu Met Ile Ser
305                 310                 315                 320

Arg Thr Pro Glu Val Thr Cys Val Val Val Asp Val Ser His Glu Asp
```

```
                325                 330                 335

Pro Glu Val Lys Phe Asn Trp Tyr Val Asp Gly Val Glu Val His Asn
            340                 345                 350

Ala Lys Thr Lys Pro Arg Glu Glu Gln Tyr Asn Ser Thr Tyr Arg Val
        355                 360                 365

Val Ser Val Leu Thr Val Leu His Gln Asp Trp Leu Asn Gly Lys Glu
    370                 375                 380

Tyr Lys Cys Lys Val Ser Asn Lys Ala Leu Pro Ser Ser Ile Glu Lys
385                 390                 395                 400

Thr Ile Ser Lys Ala Lys Gly Gln Pro Arg Glu Pro Gln Val Tyr Thr
                405                 410                 415

Leu Pro Pro Ser Arg Asp Glu Leu Thr Lys Asn Gln Val Ser Leu Thr
            420                 425                 430

Cys Leu Val Lys Gly Phe Tyr Pro Ser Asp Ile Ala Val Glu Trp Glu
        435                 440                 445

Ser Asn Gly Gln Pro Glu Asn Asn Tyr Lys Thr Thr Pro Pro Val Leu
    450                 455                 460

Asp Ser Asp Gly Ser Phe Phe Leu Tyr Ser Lys Leu Thr Val Asp Lys
465                 470                 475                 480

Ser Arg Trp Gln Gln Gly Asn Val Phe Ser Cys Ser Val Met His Glu
                485                 490                 495

Ala Leu His Asn His Tyr Thr Gln Lys Ser Leu Ser Leu Ser Pro Gly
            500                 505                 510

Lys


<210> SEQ ID NO 9
<211> LENGTH: 1467
<212> TYPE: DNA
<213> ORGANISM: Artificial
<220> FEATURE:
<223> OTHER INFORMATION: mB7R1 mFc2 Barbell

<400> SEQUENCE: 9

atgcatggct ggctgctcct ggtctgggtc caggggctga tacaggctgc cttcctcgct      60

acaggagcca cagcaggcac gatagataca aagaggaaca tctctgcaga ggaaggtggc     120

tctgtcatct tacagtgtca cttctcctct gacacagctg aagtgaccca agtcgactgg     180

aagcagcagg accagcttct ggccatttat agtgttgacc tggggtggca tgtcgcttca     240

gtcttcagtg atcgggtggt cccaggcccc agcctaggcc tcaccttcca gtctctgaca     300

atgaatgaca cgggagagta cttctgtacc tatcatacgt atcctggtgg gatttacaag     360

gggagaatat tcctgaaggt ccaagaaagc tcagtggctc agttccagac tgccgagccc     420

agatctccca caatcaagcc ctgtcctcca tgcaaatgcc cagcacctaa cctcgagggt     480

ggaccatccg tcttcatctt ccctccaaag atcaaggatg tactcatgat ctccctgagc     540

cccatagtca catgtgtggt ggtggatgtg agcgaggatg acccagatgt ccagatcagc     600

tggtttgtga acaacgtgga agtacacaca gctcagacac aaacccatag agaggattac     660

aacagtactc tccgggtggt cagtgccctc cccatccagc accaggactg gatgagtggc     720

aaagctttcg catgcgcggt caacaacaaa gacctcccag cgcccatcga gagaaccatc     780

tcaaaaccca aagggtcagt aagagctcca caggtatatg tcttgcctcc accagaagaa     840

gagatgacta agaaacaggt cactctgacc tgcatggtca cagacttcat gcctgaagac     900

atttacgtgg agtggaccaa caacgggaaa acagagctaa actacaagaa cactgaacca     960
```

-continued

```
gtcctggact ctgatggttc ttacttcatg tacagcaagc tgagagtgga aaagaagaac   1020

tgggtggaaa gaaatagcta ctcctgttca gtggtccacg agggtctgca caatcaccac   1080

acgactaaga gcttctcccg gactccgggt aaaggtggtg ggtccggagg cacgatagat   1140

acaaagagga acatctctgc agaggaaggt ggctctgtca tcttacagtg tcacttctcc   1200

tctgacacag ctgaagtgac ccaagtcgac tggaagcagc aggaccagct tctggccatt   1260

tatagtgttg acctggggtg gcatgtcgct tcagtcttca gtgatcgggt ggtcccaggc   1320

cccagcctag gcctcacctt ccagtctctg acaatgaatg acacgggaga gtacttctgt   1380

acctatcata cgtatcctgg tgggatttac aaggggagaa tattcctgaa ggtccaagaa   1440

agctcagtgg ctcagttcca gactgcc                                       1467
```

```
<210> SEQ ID NO 10
<211> LENGTH: 489
<212> TYPE: PRT
<213> ORGANISM: Artificial
<220> FEATURE:
<223> OTHER INFORMATION: mB7R1 mFc2 Barbell

<400> SEQUENCE: 10

Met His Gly Trp Leu Leu Leu Val Trp Val Gln Gly Leu Ile Gln Ala
1               5                   10                  15

Ala Phe Leu Ala Thr Gly Ala Thr Ala Gly Thr Ile Asp Thr Lys Arg
            20                  25                  30

Asn Ile Ser Ala Glu Glu Gly Gly Ser Val Ile Leu Gln Cys His Phe
        35                  40                  45

Ser Ser Asp Thr Ala Glu Val Thr Gln Val Asp Trp Lys Gln Gln Asp
    50                  55                  60

Gln Leu Leu Ala Ile Tyr Ser Val Asp Leu Gly Trp His Val Ala Ser
65                  70                  75                  80

Val Phe Ser Asp Arg Val Val Pro Gly Pro Ser Leu Gly Leu Thr Phe
                85                  90                  95

Gln Ser Leu Thr Met Asn Asp Thr Gly Glu Tyr Phe Cys Thr Tyr His
            100                 105                 110

Thr Tyr Pro Gly Gly Ile Tyr Lys Gly Arg Ile Phe Leu Lys Val Gln
        115                 120                 125

Glu Ser Ser Val Ala Gln Phe Gln Thr Ala Glu Pro Arg Ser Pro Thr
    130                 135                 140

Ile Lys Pro Cys Pro Pro Cys Lys Cys Pro Ala Pro Asn Leu Glu Gly
145                 150                 155                 160

Gly Pro Ser Val Phe Ile Phe Pro Pro Lys Ile Lys Asp Val Leu Met
                165                 170                 175

Ile Ser Leu Ser Pro Ile Val Thr Cys Val Val Val Asp Val Ser Glu
            180                 185                 190

Asp Asp Pro Asp Val Gln Ile Ser Trp Phe Val Asn Asn Val Glu Val
        195                 200                 205

His Thr Ala Gln Thr Gln Thr His Arg Glu Asp Tyr Asn Ser Thr Leu
    210                 215                 220

Arg Val Val Ser Ala Leu Pro Ile Gln His Gln Asp Trp Met Ser Gly
225                 230                 235                 240

Lys Ala Phe Ala Cys Ala Val Asn Asn Lys Asp Leu Pro Ala Pro Ile
                245                 250                 255

Glu Arg Thr Ile Ser Lys Pro Lys Gly Ser Val Arg Ala Pro Gln Val
            260                 265                 270
```

```
Tyr Val Leu Pro Pro Pro Glu Glu Glu Met Thr Lys Lys Gln Val Thr
        275                 280                 285

Leu Thr Cys Met Val Thr Asp Phe Met Pro Glu Asp Ile Tyr Val Glu
    290                 295                 300

Trp Thr Asn Asn Gly Lys Thr Glu Leu Asn Tyr Lys Asn Thr Glu Pro
305                 310                 315                 320

Val Leu Asp Ser Asp Gly Ser Tyr Phe Met Tyr Ser Lys Leu Arg Val
                325                 330                 335

Glu Lys Lys Asn Trp Val Glu Arg Asn Ser Tyr Ser Cys Ser Val Val
            340                 345                 350

His Glu Gly Leu His Asn His His Thr Thr Lys Ser Phe Ser Arg Thr
        355                 360                 365

Pro Gly Lys Gly Gly Gly Ser Gly Gly Thr Ile Asp Thr Lys Arg Asn
    370                 375                 380

Ile Ser Ala Glu Glu Gly Gly Ser Val Ile Leu Gln Cys His Phe Ser
385                 390                 395                 400

Ser Asp Thr Ala Glu Val Thr Gln Val Asp Trp Lys Gln Gln Asp Gln
                405                 410                 415

Leu Leu Ala Ile Tyr Ser Val Asp Leu Gly Trp His Val Ala Ser Val
            420                 425                 430

Phe Ser Asp Arg Val Val Pro Gly Pro Ser Leu Gly Leu Thr Phe Gln
        435                 440                 445

Ser Leu Thr Met Asn Asp Thr Gly Glu Tyr Phe Cys Thr Tyr His Thr
    450                 455                 460

Tyr Pro Gly Gly Ile Tyr Lys Gly Arg Ile Phe Leu Lys Val Gln Glu
465                 470                 475                 480

Ser Ser Val Ala Gln Phe Gln Thr Ala
                485
```

<210> SEQ ID NO 11
<211> LENGTH: 1527
<212> TYPE: DNA
<213> ORGANISM: Artificial
<220> FEATURE:
<223> OTHER INFORMATION: mB7R1 mFc2 Tandem

<400> SEQUENCE: 11

```
atgcatggct ggctgctcct ggtctgggtc caggggctga tacaggctgc cttcctcgct      60

acaggagcca cagcaggcac gatagataca aagaggaaca tctctgcaga ggaaggtggc     120

tctgtcatct tacagtgtca cttctcctct gacacagctg aagtgaccca agtcgactgg     180

aagcagcagg accagcttct ggccatttat agtgttgacc tggggtggca tgtcgcttca     240

gtcttcagtg atcgggtggt cccaggcccc agcctaggcc tcaccttcca gtctctgaca     300

atgaatgaca cgggagagta cttctgtacc tatcatacgt atcctggtgg gatttacaag     360

gggagaatat tcctgaaggt ccaagaaagc tcagtggctc agttccagac tgccggcggt     420

tcgggctcag gatcgggagg ttcaggttcc ggtggttctg gtggtgggtc cggaggcacg     480

atagatacaa agaggaacat ctctgcagag gaaggtggct ctgtcatctt acagtgtcac     540

ttctcctctg acacagctga agtgacccaa gtcgactgga agcagcagga ccagcttctg     600

gccatttata gtgttgacct ggggtggcat gtcgcttcag tcttcagtga tcgggtggtc     660

ccaggcccca gcctaggcct caccttccag tctctgacaa tgaatgacac gggagagtac     720

ttctgtacct atcatacgta tcctggtggg atttacaagg ggagaatatt cctgaaggtc     780

caagaaagct cagtggctca gttccagact gccgagccca gatctcccac aatcaagccc     840
```

```
tgtcctccat gcaaatgccc agcacctaac ctcgagggtg gaccatccgt cttcatcttc    900

cctccaaaga tcaaggatgt actcatgatc tccctgagcc ccatagtcac atgtgtggtg    960

gtggatgtga gcgaggatga cccagatgtc cagatcagct ggtttgtgaa caacgtggaa   1020

gtacacacag ctcagacaca aacccataga gaggattaca acagtactct ccgggtggtc   1080

agtgccctcc ccatccagca ccaggactgg atgagtggca aagctttcgc atgcgcggtc   1140

aacaacaaag acctcccagc gcccatcgag agaaccatct caaaacccaa agggtcagta   1200

agagctccac aggtatatgt cttgcctcca ccagaagaag agatgactaa gaaacaggtc   1260

actctgacct gcatggtcac agacttcatg cctgaagaca tttacgtgga gtggaccaac   1320

aacgggaaaa cagagctaaa ctacaagaac actgaaccag tcctggactc tgatggttct   1380

tacttcatgt acagcaagct gagagtggaa aagaagaact gggtggaaag aaatagctac   1440

tcctgttcag tggtccacga gggtctgcac aatcaccaca cgactaagag cttctcccgg   1500

actccgggta aaggtggtgg gtccgga                                       1527
```

```
<210> SEQ ID NO 12
<211> LENGTH: 509
<212> TYPE: PRT
<213> ORGANISM: Artificial
<220> FEATURE:
<223> OTHER INFORMATION: mB7R1 mFc2 Tandem

<400> SEQUENCE: 12

Met His Gly Trp Leu Leu Leu Val Trp Val Gln Gly Leu Ile Gln Ala
1               5                   10                  15

Ala Phe Leu Ala Thr Gly Ala Thr Ala Gly Thr Ile Asp Thr Lys Arg
            20                  25                  30

Asn Ile Ser Ala Glu Glu Gly Gly Ser Val Ile Leu Gln Cys His Phe
        35                  40                  45

Ser Ser Asp Thr Ala Glu Val Thr Gln Val Asp Trp Lys Gln Gln Asp
    50                  55                  60

Gln Leu Leu Ala Ile Tyr Ser Val Asp Leu Gly Trp His Val Ala Ser
65                  70                  75                  80

Val Phe Ser Asp Arg Val Val Pro Gly Pro Ser Leu Gly Leu Thr Phe
                85                  90                  95

Gln Ser Leu Thr Met Asn Asp Thr Gly Glu Tyr Phe Cys Thr Tyr His
            100                 105                 110

Thr Tyr Pro Gly Gly Ile Tyr Lys Gly Arg Ile Phe Leu Lys Val Gln
        115                 120                 125

Glu Ser Ser Val Ala Gln Phe Gln Thr Ala Gly Gly Ser Gly Ser Gly
    130                 135                 140

Ser Gly Gly Ser Gly Ser Gly Gly Ser Gly Gly Gly Ser Gly Gly Thr
145                 150                 155                 160

Ile Asp Thr Lys Arg Asn Ile Ser Ala Glu Glu Gly Gly Ser Val Ile
                165                 170                 175

Leu Gln Cys His Phe Ser Ser Asp Thr Ala Glu Val Thr Gln Val Asp
            180                 185                 190

Trp Lys Gln Gln Asp Gln Leu Leu Ala Ile Tyr Ser Val Asp Leu Gly
        195                 200                 205

Trp His Val Ala Ser Val Phe Ser Asp Arg Val Val Pro Gly Pro Ser
    210                 215                 220

Leu Gly Leu Thr Phe Gln Ser Leu Thr Met Asn Asp Thr Gly Glu Tyr
225                 230                 235                 240
```

```
Phe Cys Thr Tyr His Thr Tyr Pro Gly Gly Ile Tyr Lys Gly Arg Ile
                245                 250                 255

Phe Leu Lys Val Gln Glu Ser Ser Val Ala Gln Phe Gln Thr Ala Glu
            260                 265                 270

Pro Arg Ser Pro Thr Ile Lys Pro Cys Pro Pro Cys Lys Cys Pro Ala
        275                 280                 285

Pro Asn Leu Glu Gly Gly Pro Ser Val Phe Ile Phe Pro Pro Lys Ile
    290                 295                 300

Lys Asp Val Leu Met Ile Ser Leu Ser Pro Ile Val Thr Cys Val Val
305                 310                 315                 320

Val Asp Val Ser Glu Asp Asp Pro Asp Val Gln Ile Ser Trp Phe Val
                325                 330                 335

Asn Asn Val Glu Val His Thr Ala Gln Thr Gln Thr His Arg Glu Asp
            340                 345                 350

Tyr Asn Ser Thr Leu Arg Val Val Ser Ala Leu Pro Ile Gln His Gln
        355                 360                 365

Asp Trp Met Ser Gly Lys Ala Phe Ala Cys Ala Val Asn Asn Lys Asp
    370                 375                 380

Leu Pro Ala Pro Ile Glu Arg Thr Ile Ser Lys Pro Lys Gly Ser Val
385                 390                 395                 400

Arg Ala Pro Gln Val Tyr Val Leu Pro Pro Pro Glu Glu Glu Met Thr
                405                 410                 415

Lys Lys Gln Val Thr Leu Thr Cys Met Val Thr Asp Phe Met Pro Glu
            420                 425                 430

Asp Ile Tyr Val Glu Trp Thr Asn Asn Gly Lys Thr Glu Leu Asn Tyr
        435                 440                 445

Lys Asn Thr Glu Pro Val Leu Asp Ser Asp Gly Ser Tyr Phe Met Tyr
    450                 455                 460

Ser Lys Leu Arg Val Glu Lys Lys Asn Trp Val Glu Arg Asn Ser Tyr
465                 470                 475                 480

Ser Cys Ser Val Val His Glu Gly Leu His Asn His His Thr Thr Lys
                485                 490                 495

Ser Phe Ser Arg Thr Pro Gly Lys Gly Gly Gly Ser Gly
            500                 505
```

```
<210> SEQ ID NO 13
<211> LENGTH: 1518
<212> TYPE: DNA
<213> ORGANISM: Artificial
<220> FEATURE:
<223> OTHER INFORMATION: B7R1[G25-P141] Fc5 Barbell (otPA leader
      sequence)>

<400> SEQUENCE: 13

atggatgcaa tgaagagagg gctctgctgt gtgctgctgc tgtgtggcgc cgtcttcgtt      60

tcgctcagcc aggaaatcca tgccgagttg agacgcttcc gtagaggcac aatagaaaca     120

acggggaaca tttctgcaga gaaaggtggc tctatcatct tacaatgtca cctctcctcc     180

accacggcac aagtgaccca ggtcaactgg gagcagcagg accagcttct ggccatttgt     240

aatgctgact tggggtggca catctcccca tccttcaagg atcgagtggc cccaggtccc     300

ggcctgggcc tcaccctcca gtcgctgacc gtgaacgata caggggagta cttctgcatc     360

tatcacacct accctgatgg gacgtacact gggagaatct tcctggaggt cctagaaagc     420

tcagtggctg agcacggtgc caggttccag attccagagc ccaaatcttc agacaaaact     480
```

-continued

```
cacacatgcc caccgtgccc agcacctgaa gccgaggggg caccgtcagt cttcctcttc    540

cccccaaaac ccaaggacac cctcatgatc tcccggaccc ctgaggtcac atgcgtggtg    600

gtggacgtga gccacgaaga ccctgaggtc aagttcaact ggtacgtgga cggcgtggag    660

gtgcataatg ccaagacaaa gccgcgggag gagcagtaca acagcacgta ccgtgtggtc    720

agcgtcctca ccgtcctgca ccaggactgg ctgaatggca aggagtacaa gtgcaaggtc    780

tccaacaaag ccctcccatc ctccatcgag aaaaccatct ccaaagccaa agggcagccc    840

cgagagccac aggtgtacac cctgccccca tcccgggatg agctgaccaa gaaccaggtc    900

agcctgacct gcctggtcaa aggcttctat cccagcgaca tcgccgtgga gtgggagagc    960

aatgggcagc cggagaacaa ctacaagacc acgcctcccg tgctggactc cgacggctcc   1020

ttcttcctct acagcaagct caccgtggac aagagcaggt ggcagcaggg gaacgtcttc   1080

tcatgctccg tgatgcatga ggctctgcac aaccactaca cgcagaagag cctctccctg   1140

tctccgggta aaggtggtgg gtccggaggt acaattgaaa cgacaggcaa tatatctgcc   1200

gagaagggtg gctcgatcat attacaatgc cacctctcat ccaccactgc acaagtaacc   1260

caggtcaatt gggaacagca ggatcagctg ctggccatct gtaacgctga cttgggatgg   1320

cacatttccc catcgttcaa agatcgagtc gccccaggcc ccggcctcgg cctcacactc   1380

cagtctctga ccgtcaacga tacaggcgag tacttttgca tatatcacac ttaccctgac   1440

gggacctaca ctggtagaat cttcctagag gtcctagaga gctcagtcgc tgagcatggg   1500

gctagattcc agatccca                                                 1518
```

<210> SEQ ID NO 14
<211> LENGTH: 506
<212> TYPE: PRT
<213> ORGANISM: Artificial
<220> FEATURE:
<223> OTHER INFORMATION: B7R1[G25-P141] Fc5 Barbell (otPA leader sequence)

<400> SEQUENCE: 14

```
Met Asp Ala Met Lys Arg Gly Leu Cys Cys Val Leu Leu Leu Cys Gly
1               5                   10                  15

Ala Val Phe Val Ser Leu Ser Gln Glu Ile His Ala Glu Leu Arg Arg
            20                  25                  30

Phe Arg Arg Gly Thr Ile Glu Thr Thr Gly Asn Ile Ser Ala Glu Lys
        35                  40                  45

Gly Gly Ser Ile Ile Leu Gln Cys His Leu Ser Ser Thr Thr Ala Gln
    50                  55                  60

Val Thr Gln Val Asn Trp Glu Gln Gln Asp Gln Leu Leu Ala Ile Cys
65                  70                  75                  80

Asn Ala Asp Leu Gly Trp His Ile Ser Pro Ser Phe Lys Asp Arg Val
                85                  90                  95

Ala Pro Gly Pro Gly Leu Gly Leu Thr Leu Gln Ser Leu Thr Val Asn
            100                 105                 110

Asp Thr Gly Glu Tyr Phe Cys Ile Tyr His Thr Tyr Pro Asp Gly Thr
        115                 120                 125

Tyr Thr Gly Arg Ile Phe Leu Glu Val Leu Glu Ser Ser Val Ala Glu
    130                 135                 140

His Gly Ala Arg Phe Gln Ile Pro Glu Pro Lys Ser Ser Asp Lys Thr
145                 150                 155                 160

His Thr Cys Pro Pro Cys Pro Ala Pro Glu Ala Glu Gly Ala Pro Ser
                165                 170                 175
```

```
Val Phe Leu Phe Pro Pro Lys Pro Lys Asp Thr Leu Met Ile Ser Arg
            180                 185                 190

Thr Pro Glu Val Thr Cys Val Val Val Asp Val Ser His Glu Asp Pro
        195                 200                 205

Glu Val Lys Phe Asn Trp Tyr Val Asp Gly Val Glu Val His Asn Ala
    210                 215                 220

Lys Thr Lys Pro Arg Glu Glu Gln Tyr Asn Ser Thr Tyr Arg Val Val
225                 230                 235                 240

Ser Val Leu Thr Val Leu His Gln Asp Trp Leu Asn Gly Lys Glu Tyr
                245                 250                 255

Lys Cys Lys Val Ser Asn Lys Ala Leu Pro Ser Ser Ile Glu Lys Thr
            260                 265                 270

Ile Ser Lys Ala Lys Gly Gln Pro Arg Glu Pro Gln Val Tyr Thr Leu
        275                 280                 285

Pro Pro Ser Arg Asp Glu Leu Thr Lys Asn Gln Val Ser Leu Thr Cys
    290                 295                 300

Leu Val Lys Gly Phe Tyr Pro Ser Asp Ile Ala Val Glu Trp Glu Ser
305                 310                 315                 320

Asn Gly Gln Pro Glu Asn Asn Tyr Lys Thr Thr Pro Pro Val Leu Asp
                325                 330                 335

Ser Asp Gly Ser Phe Phe Leu Tyr Ser Lys Leu Thr Val Asp Lys Ser
            340                 345                 350

Arg Trp Gln Gln Gly Asn Val Phe Ser Cys Ser Val Met His Glu Ala
        355                 360                 365

Leu His Asn His Tyr Thr Gln Lys Ser Leu Ser Leu Ser Pro Gly Lys
    370                 375                 380

Gly Gly Gly Ser Gly Gly Thr Ile Glu Thr Thr Gly Asn Ile Ser Ala
385                 390                 395                 400

Glu Lys Gly Gly Ser Ile Ile Leu Gln Cys His Leu Ser Ser Thr Thr
                405                 410                 415

Ala Gln Val Thr Gln Val Asn Trp Glu Gln Gln Asp Gln Leu Leu Ala
            420                 425                 430

Ile Cys Asn Ala Asp Leu Gly Trp His Ile Ser Pro Ser Phe Lys Asp
        435                 440                 445

Arg Val Ala Pro Gly Pro Gly Leu Gly Leu Thr Leu Gln Ser Leu Thr
    450                 455                 460

Val Asn Asp Thr Gly Glu Tyr Phe Cys Ile Tyr His Thr Tyr Pro Asp
465                 470                 475                 480

Gly Thr Tyr Thr Gly Arg Ile Phe Leu Glu Val Leu Glu Ser Ser Val
                485                 490                 495

Ala Glu His Gly Ala Arg Phe Gln Ile Pro
            500                 505
```

```
<210> SEQ ID NO 15
<211> LENGTH: 1518
<212> TYPE: DNA
<213> ORGANISM: Artificial
<220> FEATURE:
<223> OTHER INFORMATION: B7R1[G25-P141] C69Y Fc5 Barbell (otPA leader
      sequence)

<400> SEQUENCE: 15

atggatgcaa tgaagagagg gctctgctgt gtgctgctgc tgtgtggcgc cgtcttcgtt      60

tcgctcagcc aggaaatcca tgccgagttg agacgcttcc gtagaggcac aatagaaaca     120
```

```
acggggaaca tttctgcaga gaaaggtggc tctatcatct tacaatgtca cctctcctcc    180

accacggcac aagtgaccca ggtcaactgg gagcagcagg accagcttct ggccatttat    240

aatgctgact tggggtggca catctcccca tccttcaagg atcgagtggc cccaggtccc    300

ggcctgggcc tcaccctcca gtcgctgacc gtgaacgata caggggagta cttctgcatc    360

tatcacacct accctgatgg gacgtacact gggagaatct tcctggaggt cctagaaagc    420

tcagtggctg agcacggtgc caggttccag attccagagc ccaaatcttc agacaaaact    480

cacacatgcc caccgtgccc agcacctgaa gccgaggggg caccgtcagt cttcctcttc    540

cccccaaaac ccaaggacac cctcatgatc tcccggaccc ctgaggtcac atgcgtggtg    600

gtggacgtga gccacgaaga ccctgaggtc aagttcaact ggtacgtgga cggcgtggag    660

gtgcataatg ccaagacaaa gccgcgggag gagcagtaca acagcacgta ccgtgtggtc    720

agcgtcctca ccgtcctgca ccaggactgg ctgaatggca aggagtacaa gtgcaaggtc    780

tccaacaaag ccctcccatc ctccatcgag aaaaccatct ccaaagccaa agggcagccc    840

cgagagccac aggtgtacac cctgccccca tcccgggatg agctgaccaa gaaccaggtc    900

agcctgacct gcctggtcaa aggcttctat cccagcgaca tcgccgtgga gtgggagagc    960

aatgggcagc cggagaacaa ctacaagacc acgcctcccg tgctggactc cgacggctcc   1020

ttcttcctct acagcaagct caccgtggac aagagcaggt ggcagcaggg gaacgtcttc   1080

tcatgctccg tgatgcatga ggctctgcac aaccactaca cgcagaagag cctctccctg   1140

tctccgggta aaggtggtgg gtccggaggt acaattgaaa caacaggcaa tatatctgcc   1200

gagaagggtg gctcgatcat attacaatgc cacctctcat ccaccactgc acaagtaacc   1260

caggtcaatt gggaacagca ggatcagctg ctggccatct ataacgctga cttgggatgg   1320

cacatttccc catcgttcaa agatcgagtc gccccaggcc ccggcctcgg cctcacactc   1380

cagtctctga ccgtcaacga tacaggcgag tacttttgca tatatcacac ttaccctgac   1440

gggacctaca ctggtagaat cttcctagag gtcctagaga gctcagtcgc tgagcatggg   1500

gctagattcc agatccca                                                 1518
```

<210> SEQ ID NO 16
<211> LENGTH: 506
<212> TYPE: PRT
<213> ORGANISM: Artificial
<220> FEATURE:
<223> OTHER INFORMATION: B7R1[G25-P141] Fc5 Barbell (otPA leader sequence)

<400> SEQUENCE: 16

```
Met Asp Ala Met Lys Arg Gly Leu Cys Cys Val Leu Leu Leu Cys Gly
1               5                   10                  15

Ala Val Phe Val Ser Leu Ser Gln Glu Ile His Ala Glu Leu Arg Arg
            20                  25                  30

Phe Arg Arg Gly Thr Ile Glu Thr Thr Gly Asn Ile Ser Ala Glu Lys
        35                  40                  45

Gly Gly Ser Ile Ile Leu Gln Cys His Leu Ser Ser Thr Thr Ala Gln
    50                  55                  60

Val Thr Gln Val Asn Trp Glu Gln Gln Asp Gln Leu Leu Ala Ile Cys
65                  70                  75                  80

Asn Ala Asp Leu Gly Trp His Ile Ser Pro Ser Phe Lys Asp Arg Val
                85                  90                  95

Ala Pro Gly Pro Gly Leu Gly Leu Thr Leu Gln Ser Leu Thr Val Asn
            100                 105                 110
```

```
Asp Thr Gly Glu Tyr Phe Cys Ile Tyr His Thr Tyr Pro Asp Gly Thr
        115                 120                 125

Tyr Thr Gly Arg Ile Phe Leu Glu Val Leu Glu Ser Ser Val Ala Glu
    130                 135                 140

His Gly Ala Arg Phe Gln Ile Pro Glu Pro Lys Ser Ser Asp Lys Thr
145                 150                 155                 160

His Thr Cys Pro Pro Cys Pro Ala Pro Glu Ala Glu Gly Ala Pro Ser
                165                 170                 175

Val Phe Leu Phe Pro Pro Lys Pro Lys Asp Thr Leu Met Ile Ser Arg
            180                 185                 190

Thr Pro Glu Val Thr Cys Val Val Val Asp Val Ser His Glu Asp Pro
        195                 200                 205

Glu Val Lys Phe Asn Trp Tyr Val Asp Gly Val Glu Val His Asn Ala
    210                 215                 220

Lys Thr Lys Pro Arg Glu Glu Gln Tyr Asn Ser Thr Tyr Arg Val Val
225                 230                 235                 240

Ser Val Leu Thr Val Leu His Gln Asp Trp Leu Asn Gly Lys Glu Tyr
                245                 250                 255

Lys Cys Lys Val Ser Asn Lys Ala Leu Pro Ser Ser Ile Glu Lys Thr
            260                 265                 270

Ile Ser Lys Ala Lys Gly Gln Pro Arg Glu Pro Gln Val Tyr Thr Leu
        275                 280                 285

Pro Pro Ser Arg Asp Glu Leu Thr Lys Asn Gln Val Ser Leu Thr Cys
    290                 295                 300

Leu Val Lys Gly Phe Tyr Pro Ser Asp Ile Ala Val Glu Trp Glu Ser
305                 310                 315                 320

Asn Gly Gln Pro Glu Asn Asn Tyr Lys Thr Thr Pro Pro Val Leu Asp
                325                 330                 335

Ser Asp Gly Ser Phe Phe Leu Tyr Ser Lys Leu Thr Val Asp Lys Ser
            340                 345                 350

Arg Trp Gln Gln Gly Asn Val Phe Ser Cys Ser Val Met His Glu Ala
        355                 360                 365

Leu His Asn His Tyr Thr Gln Lys Ser Leu Ser Leu Ser Pro Gly Lys
    370                 375                 380

Gly Gly Gly Ser Gly Gly Thr Ile Glu Thr Thr Gly Asn Ile Ser Ala
385                 390                 395                 400

Glu Lys Gly Gly Ser Ile Ile Leu Gln Cys His Leu Ser Ser Thr Thr
                405                 410                 415

Ala Gln Val Thr Gln Val Asn Trp Glu Gln Gln Asp Gln Leu Leu Ala
            420                 425                 430

Ile Cys Asn Ala Asp Leu Gly Trp His Ile Ser Pro Ser Phe Lys Asp
        435                 440                 445

Arg Val Ala Pro Gly Pro Gly Leu Gly Leu Thr Leu Gln Ser Leu Thr
    450                 455                 460

Val Asn Asp Thr Gly Glu Tyr Phe Cys Ile Tyr His Thr Tyr Pro Asp
465                 470                 475                 480

Gly Thr Tyr Thr Gly Arg Ile Phe Leu Glu Val Leu Glu Ser Ser Val
                485                 490                 495

Ala Glu His Gly Ala Arg Phe Gln Ile Pro
            500                 505
```

<210> SEQ ID NO 17
<211> LENGTH: 1479

<212> TYPE: DNA
<213> ORGANISM: Artificial
<220> FEATURE:
<223> OTHER INFORMATION: B7R1[G25-P141] C69Y Fc5 Barbell (EMIL leader sequence)

<400> SEQUENCE: 17

```
atgcggcgcc gcggatggag ctggatcttt ctctttcttc tgtcaggaac tgcaggtgtc     60

ctctctggca caatagaaac aacggggaac atttctgcag agaaaggtgg ctctatcatc    120

ttacaatgtc acctctcctc caccacggca caagtgaccc aggtcaactg ggagcagcag    180

gaccagcttc tggccattta taatgctgac ttggggtggc acatctcccc atcgttcaag    240

gatcgagtgg ccccaggtcc cggcctgggc ctcaccctcc agtcgctgac cgtgaacgat    300

acaggggagt acttctgcat ctatcacacc taccctgatg ggacgtacac tgggagaatc    360

ttcctggagg tcctagaaag ctcagtggct gagcacggtg ccaggttcca gattccagag    420

cccaaatctt cagacaaaac tcacacatgc ccaccgtgcc cagcacctga agccgagggg    480

gcaccgtcag tcttcctctt ccccccaaaa cccaaggaca ccctcatgat ctcccggacc    540

cctgaggtca catgcgtggt ggtggacgtg agccacgaag accctgaggt caagttcaac    600

tggtacgtgg acggcgtgga ggtgcataat gccaagacaa agccgcggga ggagcagtac    660

aacagcacgt accgtgtggt cagcgtcctc accgtcctgc accaggactg gctgaatggc    720

aaggagtaca agtgcaaggt ctccaacaaa gccctcccat cctccatcga gaaaaccatc    780

tccaaagcca aagggcagcc ccgagagcca caggtgtaca ccctgccccc atcccgggat    840

gagctgacca agaaccaggt cagcctgacc tgcctggtca aaggcttcta tcccagcgac    900

atcgccgtgg agtgggagag caatgggcag ccggagaaca actacaagac cacgcctccc    960

gtgctggact ccgacggctc cttcttcctc tacagcaagc tcaccgtgga caagagcagg   1020

tggcagcagg ggaacgtctt ctcatgctcc gtgatgcatg aggctctgca caaccactac   1080

acgcagaaga gcctctccct gtctccgggt aaaggtggtg ggtccggagg tacaattgaa   1140

acgacaggca atatatctgc cgagaagggt ggctcgatca tattacaatg ccacctctca   1200

tccaccactg cacaagtaac ccaggtcaat tgggaacagc aggatcagct gctggccatc   1260

tataacgctg acttgggatg gcacatttcc ccatcgttca aagatcgagt cgccccaggc   1320

cccggcctcg gcctcacact ccagtctctg accgtcaacg atacaggcga gtacttttgc   1380

atatatcaca cttaccctga cgggacctac actggtagaa tcttcctaga ggtcctagag   1440

agctcagtcg ctgagcatgg ggctagattc cagatccca                           1479
```

<210> SEQ ID NO 18
<211> LENGTH: 493
<212> TYPE: PRT
<213> ORGANISM: Artificial
<220> FEATURE:
<223> OTHER INFORMATION: B7R1[G25-P141] C69Y Fc5 Barbell (EMIL leader sequence)

<400> SEQUENCE: 18

```
Met Arg Arg Arg Gly Trp Ser Trp Ile Phe Leu Phe Leu Leu Ser Gly
1               5                   10                  15

Thr Ala Gly Val Leu Ser Gly Thr Ile Glu Thr Thr Gly Asn Ile Ser
            20                  25                  30

Ala Glu Lys Gly Gly Ser Ile Ile Leu Gln Cys His Leu Ser Ser Thr
        35                  40                  45

Thr Ala Gln Val Thr Gln Val Asn Trp Glu Gln Gln Asp Gln Leu Leu
```

-continued

```
    50                  55                  60

Ala Ile Tyr Asn Ala Asp Leu Gly Trp His Ile Ser Pro Ser Phe Lys
65                  70                  75                  80

Asp Arg Val Ala Pro Gly Pro Gly Leu Gly Leu Thr Leu Gln Ser Leu
                85                  90                  95

Thr Val Asn Asp Thr Gly Glu Tyr Phe Cys Ile Tyr His Thr Tyr Pro
            100                 105                 110

Asp Gly Thr Tyr Thr Gly Arg Ile Phe Leu Glu Val Leu Glu Ser Ser
        115                 120                 125

Val Ala Glu His Gly Ala Arg Phe Gln Ile Pro Glu Pro Lys Ser Ser
    130                 135                 140

Asp Lys Thr His Thr Cys Pro Pro Cys Pro Ala Pro Glu Ala Glu Gly
145                 150                 155                 160

Ala Pro Ser Val Phe Leu Phe Pro Pro Lys Pro Lys Asp Thr Leu Met
                165                 170                 175

Ile Ser Arg Thr Pro Glu Val Thr Cys Val Val Val Asp Val Ser His
            180                 185                 190

Glu Asp Pro Glu Val Lys Phe Asn Trp Tyr Val Asp Gly Val Glu Val
        195                 200                 205

His Asn Ala Lys Thr Lys Pro Arg Glu Glu Gln Tyr Asn Ser Thr Tyr
    210                 215                 220

Arg Val Val Ser Val Leu Thr Val Leu His Gln Asp Trp Leu Asn Gly
225                 230                 235                 240

Lys Glu Tyr Lys Cys Lys Val Ser Asn Lys Ala Leu Pro Ser Ser Ile
                245                 250                 255

Glu Lys Thr Ile Ser Lys Ala Lys Gly Gln Pro Arg Glu Pro Gln Val
            260                 265                 270

Tyr Thr Leu Pro Pro Ser Arg Asp Glu Leu Thr Lys Asn Gln Val Ser
        275                 280                 285

Leu Thr Cys Leu Val Lys Gly Phe Tyr Pro Ser Asp Ile Ala Val Glu
    290                 295                 300

Trp Glu Ser Asn Gly Gln Pro Glu Asn Asn Tyr Lys Thr Thr Pro Pro
305                 310                 315                 320

Val Leu Asp Ser Asp Gly Ser Phe Phe Leu Tyr Ser Lys Leu Thr Val
                325                 330                 335

Asp Lys Ser Arg Trp Gln Gln Gly Asn Val Phe Ser Cys Ser Val Met
            340                 345                 350

His Glu Ala Leu His Asn His Tyr Thr Gln Lys Ser Leu Ser Leu Ser
        355                 360                 365

Pro Gly Lys Gly Gly Gly Ser Gly Gly Thr Ile Glu Thr Thr Gly Asn
    370                 375                 380

Ile Ser Ala Glu Lys Gly Gly Ser Ile Ile Leu Gln Cys His Leu Ser
385                 390                 395                 400

Ser Thr Thr Ala Gln Val Thr Gln Val Asn Trp Glu Gln Gln Asp Gln
                405                 410                 415

Leu Leu Ala Ile Tyr Asn Ala Asp Leu Gly Trp His Ile Ser Pro Ser
            420                 425                 430

Phe Lys Asp Arg Val Ala Pro Gly Pro Gly Leu Gly Leu Thr Leu Gln
        435                 440                 445

Ser Leu Thr Val Asn Asp Thr Gly Glu Tyr Phe Cys Ile Tyr His Thr
    450                 455                 460

Tyr Pro Asp Gly Thr Tyr Thr Gly Arg Ile Phe Leu Glu Val Leu Glu
465                 470                 475                 480
```

Ser Ser Val Ala Glu His Gly Ala Arg Phe Gln Ile Pro
485 490

<210> SEQ ID NO 19
<211> LENGTH: 1524
<212> TYPE: DNA
<213> ORGANISM: Artificial
<220> FEATURE:
<223> OTHER INFORMATION: B7R1[G25-P141] C69Y Fc5 Tandem (EMIL leader sequence)

<400> SEQUENCE: 19

```
atgcggcgcc gcggatggag ctggatcttt ctctttcttc tgtcaggaac tgcaggtgtc     60
ctctctggca caatagaaac aacggggaac atttctgcag agaaaggtgg ctctatcatc    120
ttacaatgtc acctctcctc caccacggca caagtgaccc aggtcaactg ggagcagcag    180
gaccagcttc tggccattta taatgctgac ttggggtggc acatctcccc atcgttcaag    240
gatcgagtgg ccccaggtcc cggcctgggc ctcaccctcc agtcgctgac cgtgaacgat    300
acaggggagt acttctgcat ctatcacacc taccctgatg ggacgtacac tgggagaatc    360
ttcctggagg tcctagaaag ctcagtggct gagcacggtg ccaggttcca gattccaggt    420
ggtggtggtt ctggaggagg aggatcaggc gggggtggat ccggaggtgg tggttctggt    480
acaattgaaa cgacaggcaa tatatctgcc gagaagggtg gctcgatcat attacaatgc    540
cacctctcat ccaccactgc acaagtaacc caggtcaatt gggaacagca ggatcagctg    600
ctggccatct ataacgctga cttgggatgg cacatttccc catcgttcaa agatcgagtc    660
gccccaggcc ccggcctcgg cctcacactc cagtctctga ccgtcaacga tacaggcgag    720
tacttttgca tatatcacac ttaccctgac gggacctaca ctggtagaat cttcctagag    780
gtcctagaga gctcagtcgc tgagcatggg gctagattcc agatcccaga gcccaaatct    840
tcagacaaaa ctcacacatg cccaccgtgc ccagcacctg aagccgaggg ggcaccgtca    900
gtcttcctct tccccccaaa acccaaggac accctcatga tctcccggac ccctgaggtc    960
acatgcgtgg tggtggacgt gagccacgaa gaccctgagg tcaagttcaa ctggtacgtg   1020
gacggcgtgg aggtgcataa tgccaagaca aagccgcggg aggagcagta caacagcacg   1080
taccgtgtgg tcagcgtcct caccgtcctg caccaggact ggctgaatgg caaggagtac   1140
aagtgcaagg tctccaacaa agccctccca tcctccatcg agaaaaccat ctccaaagcc   1200
aaagggcagc cccgagagcc acaggtgtac accctgcccc catcccggga tgagctgacc   1260
aagaaccagg tcagcctgac ctgcctggtc aaaggcttct atcccagcga catcgccgtg   1320
gagtgggaga gcaatgggca gccggagaac aactacaaga ccacgcctcc cgtgctggac   1380
tccgacggct ccttcttcct ctacagcaag ctcaccgtgg acaagagcag gtggcagcag   1440
gggaacgtct tctcatgctc cgtgatgcat gaggctctgc acaaccacta cacgcagaag   1500
agcctctccc tgtctccggg taaa                                          1524
```

<210> SEQ ID NO 20
<211> LENGTH: 508
<212> TYPE: PRT
<213> ORGANISM: Artificial
<220> FEATURE:
<223> OTHER INFORMATION: B7R1[G25-P141] C69Y Fc5 Tandem (EMIL leader sequence)

<400> SEQUENCE: 20

Met Arg Arg Arg Gly Trp Ser Trp Ile Phe Leu Phe Leu Leu Ser Gly

-continued 1 5 10 15

Thr Ala Gly Val Leu Ser Gly Thr Ile Glu Thr Thr Gly Asn Ile Ser
20 25 30

Ala Glu Lys Gly Gly Ser Ile Ile Leu Gln Cys His Leu Ser Ser Thr
35 40 45

Thr Ala Gln Val Thr Gln Val Asn Trp Glu Gln Gln Asp Gln Leu Leu
50 55 60

Ala Ile Tyr Asn Ala Asp Leu Gly Trp His Ile Ser Pro Ser Phe Lys
65 70 75 80

Asp Arg Val Ala Pro Gly Pro Gly Leu Gly Leu Thr Leu Gln Ser Leu
85 90 95

Thr Val Asn Asp Thr Gly Glu Tyr Phe Cys Ile Tyr His Thr Tyr Pro
100 105 110

Asp Gly Thr Tyr Thr Gly Arg Ile Phe Leu Glu Val Leu Glu Ser Ser
115 120 125

Val Ala Glu His Gly Ala Arg Phe Gln Ile Pro Gly Gly Gly Gly Ser
130 135 140

Gly Gly Gly Gly Ser Gly Gly Gly Gly Ser Gly Gly Gly Gly Ser Gly
145 150 155 160

Thr Ile Glu Thr Thr Gly Asn Ile Ser Ala Glu Lys Gly Gly Ser Ile
165 170 175

Ile Leu Gln Cys His Leu Ser Ser Thr Thr Ala Gln Val Thr Gln Val
180 185 190

Asn Trp Glu Gln Gln Asp Gln Leu Leu Ala Ile Tyr Asn Ala Asp Leu
195 200 205

Gly Trp His Ile Ser Pro Ser Phe Lys Asp Arg Val Ala Pro Gly Pro
210 215 220

Gly Leu Gly Leu Thr Leu Gln Ser Leu Thr Val Asn Asp Thr Gly Glu
225 230 235 240

Tyr Phe Cys Ile Tyr His Thr Tyr Pro Asp Gly Thr Tyr Thr Gly Arg
245 250 255

Ile Phe Leu Glu Val Leu Glu Ser Ser Val Ala Glu His Gly Ala Arg
260 265 270

Phe Gln Ile Pro Glu Pro Lys Ser Ser Asp Lys Thr His Thr Cys Pro
275 280 285

Pro Cys Pro Ala Pro Glu Ala Glu Gly Ala Pro Ser Val Phe Leu Phe
290 295 300

Pro Pro Lys Pro Lys Asp Thr Leu Met Ile Ser Arg Thr Pro Glu Val
305 310 315 320

Thr Cys Val Val Val Asp Val Ser His Glu Asp Pro Glu Val Lys Phe
325 330 335

Asn Trp Tyr Val Asp Gly Val Glu Val His Asn Ala Lys Thr Lys Pro
340 345 350

Arg Glu Glu Gln Tyr Asn Ser Thr Tyr Arg Val Val Ser Val Leu Thr
355 360 365

Val Leu His Gln Asp Trp Leu Asn Gly Lys Glu Tyr Lys Cys Lys Val
370 375 380

Ser Asn Lys Ala Leu Pro Ser Ser Ile Glu Lys Thr Ile Ser Lys Ala
385 390 395 400

Lys Gly Gln Pro Arg Glu Pro Gln Val Tyr Thr Leu Pro Pro Ser Arg
405 410 415

Asp Glu Leu Thr Lys Asn Gln Val Ser Leu Thr Cys Leu Val Lys Gly
420 425 430

-continued

```
Phe Tyr Pro Ser Asp Ile Ala Val Glu Trp Glu Ser Asn Gly Gln Pro
        435                 440                 445

Glu Asn Asn Tyr Lys Thr Thr Pro Pro Val Leu Asp Ser Asp Gly Ser
    450                 455                 460

Phe Phe Leu Tyr Ser Lys Leu Thr Val Asp Lys Ser Arg Trp Gln Gln
465                 470                 475                 480

Gly Asn Val Phe Ser Cys Ser Val Met His Glu Ala Leu His Asn His
                485                 490                 495

Tyr Thr Gln Lys Ser Leu Ser Leu Ser Pro Gly Lys
            500                 505
```

<210> SEQ ID NO 21
<211> LENGTH: 1254
<212> TYPE: DNA
<213> ORGANISM: Homo sapiens

<400> SEQUENCE: 21

```
atggcccgag ccatggccgc cgcgtggccg ctgctgctgg tggcgctact ggtgctgtcc      60

tggccacccc caggaaccgg ggacgtcgtc gtgcaggcgc ccacccaggt gcccggcttc     120

ttgggcgact ccgtgacgct gccctgctac ctacaggtgc ccaacatgga ggtgacgcat     180

gtgtcacagc tgacttgggc gcggcatggt gaatctggca gcatggccgt cttccaccaa     240

acgcagggcc ccagctattc ggagtccaaa cggctggaat tcgtggcagc cagactgggc     300

gcggagctgc ggaatgcctc gctgaggatg ttcgggttgc gcgtagagga tgaaggcaac     360

tacacctgcc tgttcgtcac gttcccgcag ggcagcagga gcgtggatat ctggctccga     420

gtgcttgcca agccccagaa cacagctgag gttcagaagg tccagctcac tggagagcca     480

gtgcccatgg cccgctgcgt ctccacaggg ggtcgcccgc cagcccaaat cacctggcac     540

tcagacctgg gcgggatgcc caatacgagc caggtgccag ggttcctgtc tggcacagtc     600

actgtcacca gcctctggat attggtgccc tcaagccagg tggacggcaa gaatgtgacc     660

tgcaaggtgg agcacgagag ctttgagaag cctcagctgc tgactgtgaa cctcaccgtg     720

tactaccccc cagaggtatc catctctggc tatgataaca actggtacct tggccagaat     780

gaggccaccc tgacctgcga tgctcgcagc aacccagagc ccacaggcta taattggagc     840

acgaccatgg gtcccctgcc acccctttgct gtggcccagg gcgcccagct cctgatccgt     900

cctgtggaca aaccaatcaa cacaacttta atctgcaacg tcaccaatgc cctaggagct     960

cgccaggcag aactgaccgt ccaggtcaaa gagggacctc ccagtgagca ctcaggcatg    1020

tcccgtaacg ccatcatctt cctggttctg ggaatcctgg tttttctgat cctgctgggg    1080

atcgggattt atttctattg gtccaaatgt tcccgtgagg tcctttggca ctgtcatctg    1140

tgtccctcga gtacagagca tgccagcgcc tcagctaatg ggcatgtctc ctattcagct    1200

gtgagcagag agaacagctc ttcccaggat ccacagacag agggcacaag gtga          1254
```

<210> SEQ ID NO 22
<211> LENGTH: 417
<212> TYPE: PRT
<213> ORGANISM: Homo sapiens

<400> SEQUENCE: 22

```
Met Ala Arg Ala Met Ala Ala Ala Trp Pro Leu Leu Leu Val Ala Leu
1               5                   10                  15

Leu Val Leu Ser Trp Pro Pro Pro Gly Thr Gly Asp Val Val Val Gln
            20                  25                  30
```

```
Ala Pro Thr Gln Val Pro Gly Phe Leu Gly Asp Ser Val Thr Leu Pro
        35                  40                  45

Cys Tyr Leu Gln Val Pro Asn Met Glu Val Thr His Val Ser Gln Leu
    50                  55                  60

Thr Trp Ala Arg His Gly Glu Ser Gly Ser Met Ala Val Phe His Gln
65                  70                  75                  80

Thr Gln Gly Pro Ser Tyr Ser Glu Ser Lys Arg Leu Glu Phe Val Ala
                85                  90                  95

Ala Arg Leu Gly Ala Glu Leu Arg Asn Ala Ser Leu Arg Met Phe Gly
            100                 105                 110

Leu Arg Val Glu Asp Glu Gly Asn Tyr Thr Cys Leu Phe Val Thr Phe
        115                 120                 125

Pro Gln Gly Ser Arg Ser Val Asp Ile Trp Leu Arg Val Leu Ala Lys
    130                 135                 140

Pro Gln Asn Thr Ala Glu Val Gln Lys Val Gln Leu Thr Gly Glu Pro
145                 150                 155                 160

Val Pro Met Ala Arg Cys Val Ser Thr Gly Gly Arg Pro Pro Ala Gln
                165                 170                 175

Ile Thr Trp His Ser Asp Leu Gly Gly Met Pro Asn Thr Ser Gln Val
            180                 185                 190

Pro Gly Phe Leu Ser Gly Thr Val Thr Val Thr Ser Leu Trp Ile Leu
        195                 200                 205

Val Pro Ser Ser Gln Val Asp Gly Lys Asn Val Thr Cys Lys Val Glu
    210                 215                 220

His Glu Ser Phe Glu Lys Pro Gln Leu Leu Thr Val Asn Leu Thr Val
225                 230                 235                 240

Tyr Tyr Pro Pro Glu Val Ser Ile Ser Gly Tyr Asp Asn Asn Trp Tyr
                245                 250                 255

Leu Gly Gln Asn Glu Ala Thr Leu Thr Cys Asp Ala Arg Ser Asn Pro
            260                 265                 270

Glu Pro Thr Gly Tyr Asn Trp Ser Thr Thr Met Gly Pro Leu Pro Pro
        275                 280                 285

Phe Ala Val Ala Gln Gly Ala Gln Leu Leu Ile Arg Pro Val Asp Lys
    290                 295                 300

Pro Ile Asn Thr Thr Leu Ile Cys Asn Val Thr Asn Ala Leu Gly Ala
305                 310                 315                 320

Arg Gln Ala Glu Leu Thr Val Gln Val Lys Glu Gly Pro Pro Ser Glu
                325                 330                 335

His Ser Gly Met Ser Arg Asn Ala Ile Ile Phe Leu Val Leu Gly Ile
            340                 345                 350

Leu Val Phe Leu Ile Leu Leu Gly Ile Gly Ile Tyr Phe Tyr Trp Ser
        355                 360                 365

Lys Cys Ser Arg Glu Val Leu Trp His Cys His Leu Cys Pro Ser Ser
    370                 375                 380

Thr Glu His Ala Ser Ala Ser Ala Asn Gly His Val Ser Tyr Ser Ala
385                 390                 395                 400

Val Ser Arg Glu Asn Ser Ser Ser Gln Asp Pro Gln Thr Glu Gly Thr
                405                 410                 415

Arg


<210> SEQ ID NO 23
<211> LENGTH: 1227
<212> TYPE: DNA
```

<213> ORGANISM: Mus musculus

<400> SEQUENCE: 23

```
atggctcaac tcgcccgagc cacccgctcc ccgctgtcat ggctgctgct gctgttctgc     60

tatgcactcc ggaaagcggg tggggatata cgtgtgctgg tgccctacaa ttcgacaggc    120

gtcttgggag ggtcgaccac cttgcactgt agtctgactt ctaatgagaa tgtgactatc    180

actcaaataa cctggatgaa gaaggattca ggtggatccc acgctcttgt ggctgtcttc    240

caccccaaga aggggcccaa catcaaagag ccagagaggg tgaaattctt ggctgcccaa    300

caggatctga ggaacgcatc tctggccatc tcgaacttaa gtgtagaaga cgaaggcatc    360

tatgaatgtc agattgccac attccccaga ggcagtagaa gcaccaatgc ctggctgaag    420

gtgcaagccc gacctaagaa cactgcagag gccctggagc cctctcccac cttgatactg    480

caggatgtgg ctaaatgcat ctctgccaat ggtcaccctc ctggacgaat ctcttggccc    540

tcgaatgtga atggaagtca ccgtgaaatg aaggaaccag ggtcccagcc gggcaccacc    600

acagttacca gctacctctc catggtacct tctcgccagg cagacggcaa gaacatcacc    660

tgcacggtgg agcatgaaag cttacaggag ctggaccagc tgctggtgac cctttcccaa    720

ccctatccac ctgaaaacgt gtccatctct ggctatgacg gcaactggta tgttggcctc    780

actaacttga ccctgacctg tgaagctcac agcaaaccag cgcctgacat ggctggatat    840

aactggagca cgaacacggg tgactttccc aactctgtta agcgccaggg caatatgctt    900

ctaatctcca ccgtagagga tggtctcaat aacacggtca ttgtgtgcga agtcaccaat    960

gccctagggt ctgggcaggg ccaagtgcac atcattgtta aagagaaacc tgagaatatg   1020

cagcaaaata caagattaca cctaggctac atctttctta tcgtctttgt cctcgctgta   1080

gtcatcatca tcgcagcact atacactata cgaagatgca ggcatggtcg tgctctgcag   1140

tccaatccct cagagaggga gaacgtccag tattcatctg tgaacggcga ctgtagactg   1200

aacatggagc caaacagcac aaggtga                                       1227
```

<210> SEQ ID NO 24
<211> LENGTH: 408
<212> TYPE: PRT
<213> ORGANISM: Mus musculus

<400> SEQUENCE: 24

```
Met Ala Gln Leu Ala Arg Ala Thr Arg Ser Pro Leu Ser Trp Leu Leu
1               5                   10                  15

Leu Leu Phe Cys Tyr Ala Leu Arg Lys Ala Gly Gly Asp Ile Arg Val
            20                  25                  30

Leu Val Pro Tyr Asn Ser Thr Gly Val Leu Gly Gly Ser Thr Thr Leu
        35                  40                  45

His Cys Ser Leu Thr Ser Asn Glu Asn Val Thr Ile Thr Gln Ile Thr
    50                  55                  60

Trp Met Lys Lys Asp Ser Gly Gly Ser His Ala Leu Val Ala Val Phe
65                  70                  75                  80

His Pro Lys Lys Gly Pro Asn Ile Lys Glu Pro Glu Arg Val Lys Phe
                85                  90                  95

Leu Ala Ala Gln Gln Asp Leu Arg Asn Ala Ser Leu Ala Ile Ser Asn
            100                 105                 110

Leu Ser Val Glu Asp Glu Gly Ile Tyr Glu Cys Gln Ile Ala Thr Phe
        115                 120                 125

Pro Arg Gly Ser Arg Ser Thr Asn Ala Trp Leu Lys Val Gln Ala Arg
```

```
    130                 135                 140

Pro Lys Asn Thr Ala Glu Ala Leu Glu Pro Ser Pro Thr Leu Ile Leu
145                 150                 155                 160

Gln Asp Val Ala Lys Cys Ile Ser Ala Asn Gly His Pro Pro Gly Arg
                165                 170                 175

Ile Ser Trp Pro Ser Asn Val Asn Gly Ser His Arg Glu Met Lys Glu
            180                 185                 190

Pro Gly Ser Gln Pro Gly Thr Thr Thr Val Thr Ser Tyr Leu Ser Met
        195                 200                 205

Val Pro Ser Arg Gln Ala Asp Gly Lys Asn Ile Thr Cys Thr Val Glu
    210                 215                 220

His Glu Ser Leu Gln Glu Leu Asp Gln Leu Leu Val Thr Leu Ser Gln
225                 230                 235                 240

Pro Tyr Pro Pro Glu Asn Val Ser Ile Ser Gly Tyr Asp Gly Asn Trp
                245                 250                 255

Tyr Val Gly Leu Thr Asn Leu Thr Leu Thr Cys Glu Ala His Ser Lys
            260                 265                 270

Pro Ala Pro Asp Met Ala Gly Tyr Asn Trp Ser Thr Asn Thr Gly Asp
        275                 280                 285

Phe Pro Asn Ser Val Lys Arg Gln Gly Asn Met Leu Leu Ile Ser Thr
    290                 295                 300

Val Glu Asp Gly Leu Asn Asn Thr Val Ile Val Cys Glu Val Thr Asn
305                 310                 315                 320

Ala Leu Gly Ser Gly Gln Gly Gln Val His Ile Ile Val Lys Glu Lys
                325                 330                 335

Pro Glu Asn Met Gln Gln Asn Thr Arg Leu His Leu Gly Tyr Ile Phe
            340                 345                 350

Leu Ile Val Phe Val Leu Ala Val Val Ile Ile Ile Ala Ala Leu Tyr
        355                 360                 365

Thr Ile Arg Arg Cys Arg His Gly Arg Ala Leu Gln Ser Asn Pro Ser
    370                 375                 380

Glu Arg Glu Asn Val Gln Tyr Ser Ser Val Asn Gly Asp Cys Arg Leu
385                 390                 395                 400

Asn Met Glu Pro Asn Ser Thr Arg
                405
```

<210> SEQ ID NO 25
<211> LENGTH: 5
<212> TYPE: PRT
<213> ORGANISM: Artificial
<220> FEATURE:
<223> OTHER INFORMATION: Polypeptide linker

<400> SEQUENCE: 25

```
Gly Gly Gly Ser Gly
1               5
```

<210> SEQ ID NO 26
<211> LENGTH: 25
<212> TYPE: PRT
<213> ORGANISM: Artificial
<220> FEATURE:
<223> OTHER INFORMATION: Polypeptide linker
<220> FEATURE:
<221> NAME/KEY: misc_feature
<222> LOCATION: (16)..(19)
<223> OTHER INFORMATION: Xaa is either Gly or is absent
<220> FEATURE:
<221> NAME/KEY: misc_feature
<222> LOCATION: (20)..(20)
<223> OTHER INFORMATION: Xaa is either Ser or is absent
<220> FEATURE:
<221> NAME/KEY: misc_feature
<222> LOCATION: (21)..(24)
<223> OTHER INFORMATION: Xaa is either Gly or is absent
<220> FEATURE:
<221> NAME/KEY: misc_feature
<222> LOCATION: (25)..(25)
<223> OTHER INFORMATION: Xaa is either Ser or is absent

<400> SEQUENCE: 26

```
Gly Gly Gly Gly Ser Gly Gly Gly Gly Ser Gly Gly Gly Gly Ser Xaa
1               5                   10                  15

Xaa Xaa Xaa Xaa Xaa Xaa Xaa Xaa Xaa
            20                  25
```

<210> SEQ ID NO 27
<211> LENGTH: 330
<212> TYPE: PRT
<213> ORGANISM: Homo sapiens

<400> SEQUENCE: 27

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
```

```
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330


<210> SEQ ID NO 28
<211> LENGTH: 232
<212> TYPE: PRT
<213> ORGANISM: Homo sapiens

<400> SEQUENCE: 28

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230


<210> SEQ ID NO 29
<211> LENGTH: 232
<212> TYPE: PRT
<213> ORGANISM: Artificial
<220> FEATURE:
<223> OTHER INFORMATION: Fc-488

<400> SEQUENCE: 29

Glu Pro Arg Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30
```

```
Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230


<210> SEQ ID NO 30
<211> LENGTH: 232
<212> TYPE: PRT
<213> ORGANISM: Artificial
<220> FEATURE:
<223> OTHER INFORMATION: Fc4

<400> SEQUENCE: 30

Glu Pro Arg Ser Ser Asp Lys Thr His Thr Cys Pro Pro Cys Pro Ala
1               5                   10                  15

Pro Glu Ala Glu Gly Ala Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ser Ser Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160
```

```
Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230


<210> SEQ ID NO 31
<211> LENGTH: 232
<212> TYPE: PRT
<213> ORGANISM: Artificial
<220> FEATURE:
<223> OTHER INFORMATION: Fc5

<400> SEQUENCE: 31

Glu Pro Lys Ser Ser Asp Lys Thr His Thr Cys Pro Pro Cys Pro Ala
1               5                   10                  15

Pro Glu Ala Glu Gly Ala Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ser Ser Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230


<210> SEQ ID NO 32
<211> LENGTH: 231
<212> TYPE: PRT
<213> ORGANISM: Artificial
<220> FEATURE:
<223> OTHER INFORMATION: Fc6
```

-continued

<400> SEQUENCE: 32

Glu Pro Lys Ser Ser Asp Lys Thr His Thr Cys Pro Pro Cys Pro Ala
1 5 10 15

Pro Glu Ala Glu Gly Ala Pro Ser Val Phe Leu Phe Pro Pro Lys Pro
20 25 30

Lys Asp Thr Leu Met Ile Ser Arg Thr Pro Glu Val Thr Cys Val Val
35 40 45

Val Asp Val Ser His Glu Asp Pro Glu Val Lys Phe Asn Trp Tyr Val
50 55 60

Asp Gly Val Glu Val His Asn Ala Lys Thr Lys Pro Arg Glu Glu Gln
65 70 75 80

Tyr Asn Ser Thr Tyr Arg Val Val Ser Val Leu Thr Val Leu His Gln
85 90 95

Asp Trp Leu Asn Gly Lys Glu Tyr Lys Cys Lys Val Ser Asn Lys Ala
100 105 110

Leu Pro Ser Ser Ile Glu Lys Thr Ile Ser Lys Ala Lys Gly Gln Pro
115 120 125

Arg Glu Pro Gln Val Tyr Thr Leu Pro Pro Ser Arg Asp Glu Leu Thr
130 135 140

Lys Asn Gln Val Ser Leu Thr Cys Leu Val Lys Gly Phe Tyr Pro Ser
145 150 155 160

Asp Ile Ala Val Glu Trp Glu Ser Asn Gly Gln Pro Glu Asn Asn Tyr
165 170 175

Lys Thr Thr Pro Pro Val Leu Asp Ser Asp Gly Ser Phe Phe Leu Tyr
180 185 190

Ser Lys Leu Thr Val Asp Lys Ser Arg Trp Gln Gln Gly Asn Val Phe
195 200 205

Ser Cys Ser Val Met His Glu Ala Leu His Asn His Tyr Thr Gln Lys
210 215 220

Ser Leu Ser Leu Ser Pro Gly
225 230

<210> SEQ ID NO 33
<211> LENGTH: 232
<212> TYPE: PRT
<213> ORGANISM: Artificial
<220> FEATURE:
<223> OTHER INFORMATION: Fc7

<400> SEQUENCE: 33

Glu Pro Lys Ser Cys Asp Lys Thr His Thr Cys Pro Pro Cys Pro Ala
1 5 10 15

Pro Glu Leu Leu Gly Gly Pro Ser Val Phe Leu Phe Pro Pro Lys Pro
20 25 30

Lys Asp Thr Leu Met Ile Ser Arg Thr Pro Glu Val Thr Cys Val Val
35 40 45

Val Asp Val Ser His Glu Asp Pro Glu Val Lys Phe Asn Trp Tyr Val
50 55 60

Asp Gly Val Glu Val His Asn Ala Lys Thr Lys Pro Arg Glu Glu Gln
65 70 75 80

Tyr Glu Ser Thr Tyr Arg Val Val Ser Val Leu Thr Val Leu His Gln
85 90 95

Asp Trp Leu Asn Gly Lys Glu Tyr Lys Cys Lys Val Ser Asn Lys Ala
100 105 110

Leu Pro Ala Pro Ile Glu Lys Thr Ile Ser Lys Ala Lys Gly Gln Pro

```
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230


<210> SEQ ID NO 34
<211> LENGTH: 346
<212> TYPE: PRT
<213> ORGANISM: Artificial
<220> FEATURE:
<223> OTHER INFORMATION: mB7R1-mFc2

<400> SEQUENCE: 34

Gly Thr Ile Asp Thr Lys Arg Asn Ile Ser Ala Glu Glu Gly Gly Ser
1               5                   10                  15

Val Ile Leu Gln Cys His Phe Ser Ser Asp Thr Ala Glu Val Thr Gln
            20                  25                  30

Val Asp Trp Lys Gln Gln Asp Gln Leu Leu Ala Ile Tyr Ser Val Asp
        35                  40                  45

Leu Gly Trp His Val Ala Ser Val Phe Ser Asp Arg Val Val Pro Gly
    50                  55                  60

Pro Ser Leu Gly Leu Thr Phe Gln Ser Leu Thr Met Asn Asp Thr Gly
65                  70                  75                  80

Glu Tyr Phe Cys Thr Tyr His Thr Tyr Pro Gly Gly Ile Tyr Lys Gly
                85                  90                  95

Arg Ile Phe Leu Lys Val Gln Glu Ser Ser Val Ala Gln Phe Gln Thr
            100                 105                 110

Ala Glu Pro Arg Ser Pro Thr Ile Lys Pro Cys Pro Pro Cys Lys Cys
        115                 120                 125

Pro Ala Pro Asn Leu Glu Gly Gly Pro Ser Val Phe Ile Phe Pro Pro
    130                 135                 140

Lys Ile Lys Asp Val Leu Met Ile Ser Leu Ser Pro Ile Val Thr Cys
145                 150                 155                 160

Val Val Val Asp Val Ser Glu Asp Asp Pro Asp Val Gln Ile Ser Trp
                165                 170                 175

Phe Val Asn Asn Val Glu Val His Thr Ala Gln Thr Gln Thr His Arg
            180                 185                 190

Glu Asp Tyr Asn Ser Thr Leu Arg Val Val Ser Ala Leu Pro Ile Gln
        195                 200                 205

His Gln Asp Trp Met Ser Gly Lys Ala Phe Ala Cys Ala Val Asn Asn
    210                 215                 220

Lys Asp Leu Pro Ala Pro Ile Glu Arg Thr Ile Ser Lys Pro Lys Gly
225                 230                 235                 240

Ser Val Arg Ala Pro Gln Val Tyr Val Leu Pro Pro Pro Glu Glu Glu
```

-continued

```
                245                 250                 255

Met Thr Lys Lys Gln Val Thr Leu Thr Cys Met Val Thr Asp Phe Met
            260                 265                 270

Pro Glu Asp Ile Tyr Val Glu Trp Thr Asn Asn Gly Lys Thr Glu Leu
        275                 280                 285

Asn Tyr Lys Asn Thr Glu Pro Val Leu Asp Ser Asp Gly Ser Tyr Phe
    290                 295                 300

Met Tyr Ser Lys Leu Arg Val Glu Lys Lys Asn Trp Val Glu Arg Asn
305                 310                 315                 320

Ser Tyr Ser Cys Ser Val Val His Glu Gly Leu His Asn His His Thr
                325                 330                 335

Thr Lys Ser Phe Ser Arg Thr Pro Gly Lys
            340                 345


<210> SEQ ID NO 35
<211> LENGTH: 168
<212> TYPE: PRT
<213> ORGANISM: Artificial
<220> FEATURE:
<223> OTHER INFORMATION: mB7R1-VASP

<400> SEQUENCE: 35

Gly Thr Ile Asp Thr Lys Arg Asn Ile Ser Ala Glu Glu Gly Gly Ser
1               5                   10                  15

Val Ile Leu Gln Cys His Phe Ser Ser Asp Thr Ala Glu Val Thr Gln
            20                  25                  30

Val Asp Trp Lys Gln Gln Asp Gln Leu Leu Ala Ile Tyr Ser Val Asp
        35                  40                  45

Leu Gly Trp His Val Ala Ser Val Phe Ser Asp Arg Val Val Pro Gly
    50                  55                  60

Pro Ser Leu Gly Leu Thr Phe Gln Ser Leu Thr Met Asn Asp Thr Gly
65                  70                  75                  80

Glu Tyr Phe Cys Thr Tyr His Thr Tyr Pro Gly Gly Ile Tyr Lys Gly
                85                  90                  95

Arg Ile Phe Leu Lys Val Gln Glu Ser Ser Val Ala Gln Phe Gln Thr
            100                 105                 110

Ala Glu Pro Arg Ser Gly Ser Gly Gly Ser Gly Gly Ser Asp Leu Gln
        115                 120                 125

Arg Val Lys Gln Glu Leu Leu Glu Glu Val Lys Lys Glu Leu Gln Lys
    130                 135                 140

Val Lys Glu Glu Ile Ile Glu Ala Phe Val Gln Glu Leu Arg Gly Ser
145                 150                 155                 160

Gly Gly His His His His His His
                165


<210> SEQ ID NO 36
<211> LENGTH: 55
<212> TYPE: DNA
<213> ORGANISM: Artificial
<220> FEATURE:
<223> OTHER INFORMATION: Oligonucleotide primer (zc60639)

<400> SEQUENCE: 36

caggtgtcca gggaattcat ataggccggc caccatgcat ggctggctgc tcctg          55


<210> SEQ ID NO 37
<211> LENGTH: 61
<212> TYPE: DNA
```

<213> ORGANISM: Artificial
<220> FEATURE:
<223> OTHER INFORMATION: Oligonucleotide primer (zc60643)

<400> SEQUENCE: 37
cggccgcatt cctgaggttt ttatccggac ccaccacctt tacccggagt ccgggagaag 60
c 61

<210> SEQ ID NO 38
<211> LENGTH: 59
<212> TYPE: DNA
<213> ORGANISM: Artificial
<220> FEATURE:
<223> OTHER INFORMATION: Oligonucleotide primer (zc60645)

<400> SEQUENCE: 38
caaccccaga gctgttttaa ggcgcgcctc tagaaacggc cgcattcctg aggtttta 59

<210> SEQ ID NO 39
<211> LENGTH: 34
<212> TYPE: DNA
<213> ORGANISM: Artificial
<220> FEATURE:
<223> OTHER INFORMATION: Oligonucleotide primer (zc60642)

<400> SEQUENCE: 39
gtggtgggtc cggaggcacg atagatacaa agag 34

<210> SEQ ID NO 40
<211> LENGTH: 49
<212> TYPE: DNA
<213> ORGANISM: Artificial
<220> FEATURE:
<223> OTHER INFORMATION: Oligonucleotide primer (zc60641)

<400> SEQUENCE: 40
gcgcctctag aaacggccgc attcctgagg tttttaggca gtctggaac 49

<210> SEQ ID NO 41
<211> LENGTH: 64
<212> TYPE: DNA
<213> ORGANISM: Artificial
<220> FEATURE:
<223> OTHER INFORMATION: Oligonucleotide primer (zc53051)

<400> SEQUENCE: 41
caggtgtcca gggaattcat ataggccggc caccatgcgc tggtgtctcc tcctgatctg 60
ggcc 64

<210> SEQ ID NO 42
<211> LENGTH: 47
<212> TYPE: DNA
<213> ORGANISM: Artificial
<220> FEATURE:
<223> OTHER INFORMATION: Oligonucleotide primer (zc60385)

<400> SEQUENCE: 42
gagttttgtc tgaagatttg ggctctggaa tctggaacct ggcaccg 47

<210> SEQ ID NO 43
<211> LENGTH: 45
<212> TYPE: DNA
<213> ORGANISM: Artificial
<220> FEATURE:
<223> OTHER INFORMATION: Oligonucleotide primer (zc60386

<400> SEQUENCE: 43
caggttccag attccagagc ccaaatcttc agacaaaact cacac 45

<210> SEQ ID NO 44
<211> LENGTH: 61
<212> TYPE: DNA
<213> ORGANISM: Artificial
<220> FEATURE:
<223> OTHER INFORMATION: Oligonucleotide primer (zc59433)

<400> SEQUENCE: 44
aaagatctca ttcctgaggt ttttatccgg acccaccacc tttacccgga gacagggaga 60
g 61

<210> SEQ ID NO 45
<211> LENGTH: 62
<212> TYPE: DNA
<213> ORGANISM: Artificial
<220> FEATURE:
<223> OTHER INFORMATION: Oligonucleotide primer (zc59434)

<400> SEQUENCE: 45
caaccccaga gctgttttaa ggcgcgcctc tagattaaaa gatctcattc ctgaggtttt 60
ta 62

<210> SEQ ID NO 46
<211> LENGTH: 41
<212> TYPE: DNA
<213> ORGANISM: Artificial
<220> FEATURE:
<223> OTHER INFORMATION: Oligonucleotide primer (zc60640)

<400> SEQUENCE: 46
gatcctgagc ccgaaccgcc ggcagtctgg aactgagcca c 41

<210> SEQ ID NO 47
<211> LENGTH: 63
<212> TYPE: DNA
<213> ORGANISM: Artificial
<220> FEATURE:
<223> OTHER INFORMATION: Oligonucleotide primer (zc60644)

<400> SEQUENCE: 47
gcctccggac ccaccaccag aaccaccgga acctgaacct cccgatcctg agcccgaacc 60
gcc 63

<210> SEQ ID NO 48
<211> LENGTH: 34
<212> TYPE: DNA
<213> ORGANISM: Artificial
<220> FEATURE:
<223> OTHER INFORMATION: Oligonucleotide primer (zc60642)

<400> SEQUENCE: 48
gtggtgggtc cggaggcacg atagatacaa agag 34

<210> SEQ ID NO 49
<211> LENGTH: 33
<212> TYPE: DNA
<213> ORGANISM: Artificial
<220> FEATURE:
<223> OTHER INFORMATION: Oligonucleotide primer (zc28844)

<400> SEQUENCE: 49
gacggatggt ccaccctcga ggttaggtgc tgg 33

<210> SEQ ID NO 50
<211> LENGTH: 45
<212> TYPE: DNA
<213> ORGANISM: Artificial
<220> FEATURE:
<223> OTHER INFORMATION: Oligonucleotide primer (zc62529)

<400> SEQUENCE: 50
cgatcctgag cccgaaccgc ctggaatctg gaacctggca ccgtg 45

<210> SEQ ID NO 51
<211> LENGTH: 66
<212> TYPE: DNA
<213> ORGANISM: Artificial
<220> FEATURE:
<223> OTHER INFORMATION: Oligonucleotide primer (zc62530)

<400> SEQUENCE: 51
accagatccg gacccaccac cagaaccacc ggaacctgaa cctcccgatc ctgagcccga 60
accgcc 66

<210> SEQ ID NO 52
<211> LENGTH: 43
<212> TYPE: DNA
<213> ORGANISM: Artificial
<220> FEATURE:
<223> OTHER INFORMATION: Oligonucleotide primer (zc62531)

<400> SEQUENCE: 52
ctggtggtgg gtccggaatg atgacaggca caatagaaac aac 43

<210> SEQ ID NO 53
<211> LENGTH: 54
<212> TYPE: DNA
<213> ORGANISM: Artificial
<220> FEATURE:
<223> OTHER INFORMATION: Oligonucleotide primer (zc62532)

<400> SEQUENCE: 53
accagaaaga tctcattcct gaggttttta tttacccgga gacagggaga ggct 54

<210> SEQ ID NO 54
<211> LENGTH: 60
<212> TYPE: DNA
<213> ORGANISM: Artificial
<220> FEATURE:
<223> OTHER INFORMATION: Oligonucleotide primer (zc64230)

<400> SEQUENCE: 54
caggaaatcc atgccgagtt gagacgcttc cgtagaggca caatagaaac aacggggaac 60

<210> SEQ ID NO 55
<211> LENGTH: 66
<212> TYPE: DNA
<213> ORGANISM: Artificial
<220> FEATURE:
<223> OTHER INFORMATION: Oligonucleotide primer (zc64219)

<400> SEQUENCE: 55
cttgaaggat ggggagatgt gccaccccaa gtcagcatta caaatggcca gaagctggtc 60
ctgctg 66

<210> SEQ ID NO 56
<211> LENGTH: 60
<212> TYPE: DNA
<213> ORGANISM: Artificial
<220> FEATURE:
<223> OTHER INFORMATION: Oligonucleotide primer (zc64215)

<400> SEQUENCE: 56
aatgctgact tggggtggca catctcccca tccttcaagg atcgagtggc cccaggtccc 60

<210> SEQ ID NO 57
<211> LENGTH: 60
<212> TYPE: DNA
<213> ORGANISM: Artificial
<220> FEATURE:
<223> OTHER INFORMATION: Oligonucleotide primer (zc64216)

<400> SEQUENCE: 57
tccggaccca ccacctttac ccggagacag ggagaggctc ttctgcgtgt agtggttgtg 60

<210> SEQ ID NO 58
<211> LENGTH: 66
<212> TYPE: DNA
<213> ORGANISM: Artificial
<220> FEATURE:
<223> OTHER INFORMATION: Oligonucleotide primer (zc64228)

<400> SEQUENCE: 58
aagagcctct ccctgtctcc gggtaaaggt ggtgggtccg gaggtacaat tgaaacgaca 60
ggcaat 66

<210> SEQ ID NO 59
<211> LENGTH: 63
<212> TYPE: DNA
<213> ORGANISM: Artificial
<220> FEATURE:
<223> OTHER INFORMATION: Oligonucleotide primer (zc64220)

<400> SEQUENCE: 59
gtggcattgt aatatgatcg agccaccctt ctcggcagat atattgcctg tcgtttcaat 60
tgt 63

<210> SEQ ID NO 60
<211> LENGTH: 73
<212> TYPE: DNA
<213> ORGANISM: Artificial
<220> FEATURE:
<223> OTHER INFORMATION: Oligonucleotide primer (zc64224)

<400> SEQUENCE: 60
gatcatatta caatgccacc tctcatccac cactgcacaa gtaacccagg tcaattggga 60
acagcaggat cag 73

<210> SEQ ID NO 61
<211> LENGTH: 66
<212> TYPE: DNA
<213> ORGANISM: Artificial
<220> FEATURE:
<223> OTHER INFORMATION: Oligonucleotide primer (zc64231)

<400> SEQUENCE: 61
cgatggggaa atgtgccatc ccaagtcagc gttacagatg gccagcagct gatcctgctg 60

-continued

```
ttccca                                                              66


<210> SEQ ID NO 62
<211> LENGTH: 63
<212> TYPE: DNA
<213> ORGANISM: Artificial
<220> FEATURE:
<223> OTHER INFORMATION: Oligonucleotide primer (zc64225)

<400> SEQUENCE: 62

tggcacattt ccccatcgtt caaagatcga gtcgccccag gccccggcct cggcctcaca     60

ctc                                                                 63


<210> SEQ ID NO 63
<211> LENGTH: 66
<212> TYPE: DNA
<213> ORGANISM: Artificial
<220> FEATURE:
<223> OTHER INFORMATION: Oligonucleotide primer (zc64221)

<400> SEQUENCE: 63

gtgatatatg caaaagtact cgcctgtatc gttgacggtc agagactgga gtgtgaggcc     60

gaggcc                                                              66


<210> SEQ ID NO 64
<211> LENGTH: 68
<212> TYPE: DNA
<213> ORGANISM: Artificial
<220> FEATURE:
<223> OTHER INFORMATION: Oligonucleotide primer (zc64226)

<400> SEQUENCE: 64

gtacttttgc atatatcaca cttaccctga cgggacctac actggtagaa tcttcctaga     60

ggtcctag                                                            68


<210> SEQ ID NO 65
<211> LENGTH: 65
<212> TYPE: DNA
<213> ORGANISM: Artificial
<220> FEATURE:
<223> OTHER INFORMATION: Oligonucleotide primer (zc64222)

<400> SEQUENCE: 65

ttatgggatc tggaatctag ccccatgctc agcgactgag ctctctagga cctctaggaa     60

gattc                                                               65


<210> SEQ ID NO 66
<211> LENGTH: 69
<212> TYPE: DNA
<213> ORGANISM: Artificial
<220> FEATURE:
<223> OTHER INFORMATION: Oligonucleotide primer (zc64223)

<400> SEQUENCE: 66

taaggcgcgc ctctagatta aaagatctca ttcctgaggt tttatggga tctggaatct     60

agccccatg                                                           69


<210> SEQ ID NO 67
<211> LENGTH: 69
<212> TYPE: DNA
<213> ORGANISM: Artificial
<220> FEATURE:
<223> OTHER INFORMATION: Oligonucleotide primer (zc64258)
```

<400> SEQUENCE: 67
catggggcta gattccagat cccataaaaa cctcaggaat gagatctttt aatctagagg 60
cgcgcctta 69

<210> SEQ ID NO 68
<211> LENGTH: 66
<212> TYPE: DNA
<213> ORGANISM: Artificial
<220> FEATURE:
<223> OTHER INFORMATION: Oligonucleotide primer (zc64218)

<400> SEQUENCE: 68
cttgaaggat ggggagatgt gccaccccaa gtcagcatta taaatggcca gaagctggtc 60
ctgctg 66

<210> SEQ ID NO 69
<211> LENGTH: 66
<212> TYPE: DNA
<213> ORGANISM: Artificial
<220> FEATURE:
<223> OTHER INFORMATION: Oligonucleotide primer (zc64227)

<400> SEQUENCE: 69
cgatggggaa atgtgccatc ccaagtcagc gttatagatg gccagcagct gatcctgctg 60
ttccca 66

<210> SEQ ID NO 70
<211> LENGTH: 82
<212> TYPE: DNA
<213> ORGANISM: Artificial
<220> FEATURE:
<223> OTHER INFORMATION: Oligonucleotide primer (zc65030)

<400> SEQUENCE: 70
tctccacagg tgtccaggga attcatatag gccggccacc atgcggcgcc gcggatggag 60
ctggatcttt ctctttcttc tg 82

<210> SEQ ID NO 71
<211> LENGTH: 72
<212> TYPE: DNA
<213> ORGANISM: Artificial
<220> FEATURE:
<223> OTHER INFORMATION: Oligonucleotide primer (zc65029)

<400> SEQUENCE: 71
agctggatct ttctctttct tctgtcagga actgcaggtg tcctctctgg cacaatagaa 60
acaacgggga ac 72

<210> SEQ ID NO 72
<211> LENGTH: 82
<212> TYPE: DNA
<213> ORGANISM: Artificial
<220> FEATURE:
<223> OTHER INFORMATION: Oligonucleotide primer (zc65050)

<400> SEQUENCE: 72
agaaccacca cctccggatc cacccccgcc tgatcctcct cctccagaac caccaccacc 60
tggaatctgg aacctggcac cg 82

-continued

<210> SEQ ID NO 73
<211> LENGTH: 69
<212> TYPE: DNA
<213> ORGANISM: Artificial
<220> FEATURE:
<223> OTHER INFORMATION: Oligonucleotide primer (zc65051)

<400> SEQUENCE: 73
ggaggaggag gatcaggcgg gggtggatcc ggaggtggtg gttctggtac aattgaaacg 60
acaggcaat 69

<210> SEQ ID NO 74
<211> LENGTH: 61
<212> TYPE: DNA
<213> ORGANISM: Artificial
<220> FEATURE:
<223> OTHER INFORMATION: Oligonucleotide primer (zc65052)

<400> SEQUENCE: 74
cggtgggcat gtgtgagttt tgtctgaaga tttgggctct gggatctgga atctagcccc 60
a 61

<210> SEQ ID NO 75
<211> LENGTH: 57
<212> TYPE: DNA
<213> ORGANISM: Artificial
<220> FEATURE:
<223> OTHER INFORMATION: Oligonucleotide primer (zc65053)

<400> SEQUENCE: 75
gagcccaaat cttcagacaa aactcacaca tgcccaccgt gcccagcacc tgaagcc 57

<210> SEQ ID NO 76
<211> LENGTH: 85
<212> TYPE: DNA
<213> ORGANISM: Artificial
<220> FEATURE:
<223> OTHER INFORMATION: Oligonucleotide primer (zc65054)

<400> SEQUENCE: 76
caaccccaga gctgttttaa ggcgcgcctc tagattaaaa gatctcattc ctgaggtttt 60
tatttacccg gagacaggga gaggc 85

<210> SEQ ID NO 77
<211> LENGTH: 44
<212> TYPE: DNA
<213> ORGANISM: Artificial
<220> FEATURE:
<223> OTHER INFORMATION: Oligonucleotide primer (zc59435)

<400> SEQUENCE: 77
ggtaaaggtg gtgggtccgg aatgatgaca ggcacaatag aaac 44

<210> SEQ ID NO 78
<211> LENGTH: 55
<212> TYPE: DNA
<213> ORGANISM: Artificial
<220> FEATURE:
<223> OTHER INFORMATION: Oligonucleotide primer (zc60392)

<400> SEQUENCE: 78
ctagattaaa agatctcatt cctgaggttt ttatggaatc tggaacctgg caccg 55

<210> SEQ ID NO 79
<211> LENGTH: 352
<212> TYPE: PRT
<213> ORGANISM: Artificial
<220> FEATURE:
<223> OTHER INFORMATION: B7R1-Fc2

<400> SEQUENCE: 79

```
Met Met Thr Gly Thr Ile Glu Thr Thr Gly Asn Ile Ser Ala Glu Lys
1               5                   10                  15

Gly Gly Ser Ile Ile Leu Gln Cys His Leu Ser Ser Thr Thr Ala Gln
            20                  25                  30

Val Thr Gln Val Asn Trp Glu Gln Gln Asp Gln Leu Leu Ala Ile Cys
        35                  40                  45

Asn Ala Asp Leu Gly Trp His Ile Ser Pro Ser Phe Lys Asp Arg Val
    50                  55                  60

Ala Pro Gly Pro Gly Leu Gly Leu Thr Leu Gln Ser Leu Thr Val Asn
65                  70                  75                  80

Asp Thr Gly Glu Tyr Phe Cys Ile Tyr His Thr Tyr Pro Asp Gly Ala
                85                  90                  95

Tyr Thr Gly Arg Ile Phe Leu Glu Val Leu Glu Ser Ser Val Ala Glu
            100                 105                 110

His Gly Ala Arg Phe Gln Ile Glu Pro Arg Ser Pro Thr Ile Lys Pro
        115                 120                 125

Cys Pro Pro Cys Lys Cys Pro Ala Pro Asn Leu Glu Gly Gly Pro Ser
    130                 135                 140

Val Phe Ile Phe Pro Pro Lys Ile Lys Asp Val Leu Met Ile Ser Leu
145                 150                 155                 160

Ser Pro Ile Val Thr Cys Val Val Val Asp Val Ser Glu Asp Asp Pro
                165                 170                 175

Asp Val Gln Ile Ser Trp Phe Val Asn Asn Val Glu Val His Thr Ala
            180                 185                 190

Gln Thr Gln Thr His Arg Glu Asp Tyr Asn Ser Thr Leu Arg Val Val
        195                 200                 205

Ser Ala Leu Pro Ile Gln His Gln Asp Trp Met Ser Gly Lys Ala Phe
    210                 215                 220

Ala Cys Ala Val Asn Asn Lys Asp Leu Pro Ala Pro Ile Glu Arg Thr
225                 230                 235                 240

Ile Ser Lys Pro Lys Gly Ser Val Arg Ala Pro Gln Val Tyr Val Leu
                245                 250                 255

Pro Pro Pro Glu Glu Glu Met Thr Lys Lys Gln Val Thr Leu Thr Cys
            260                 265                 270

Met Val Thr Asp Phe Met Pro Glu Asp Ile Tyr Val Glu Trp Thr Asn
        275                 280                 285

Asn Gly Lys Thr Glu Leu Asn Tyr Lys Asn Thr Glu Pro Val Leu Asp
    290                 295                 300

Ser Asp Gly Ser Tyr Phe Met Tyr Ser Lys Leu Arg Val Glu Lys Lys
305                 310                 315                 320

Asn Trp Val Glu Arg Asn Ser Tyr Ser Cys Ser Val Val His Glu Gly
                325                 330                 335

Leu His Asn His His Thr Thr Lys Ser Phe Ser Arg Thr Pro Gly Lys
            340                 345                 350
```

```
<210> SEQ ID NO 80
<211> LENGTH: 349
<212> TYPE: PRT
<213> ORGANISM: Artificial
<220> FEATURE:
<223> OTHER INFORMATION: B7R1[G25-P141] C69Y Fc5

<400> SEQUENCE: 80

Gly Thr Ile Glu Thr Thr Gly Asn Ile Ser Ala Glu Lys Gly Gly Ser
1               5                   10                  15

Ile Ile Leu Gln Cys His Leu Ser Ser Thr Thr Ala Gln Val Thr Gln
            20                  25                  30

Val Asn Trp Glu Gln Gln Asp Gln Leu Leu Ala Ile Tyr Asn Ala Asp
        35                  40                  45

Leu Gly Trp His Ile Ser Pro Ser Phe Lys Asp Arg Val Ala Pro Gly
    50                  55                  60

Pro Gly Leu Gly Leu Thr Leu Gln Ser Leu Thr Val Asn Asp Thr Gly
65                  70                  75                  80

Glu Tyr Phe Cys Ile Tyr His Thr Tyr Pro Asp Gly Thr Tyr Thr Gly
                85                  90                  95

Arg Ile Phe Leu Glu Val Leu Glu Ser Ser Val Ala Glu His Gly Ala
            100                 105                 110

Arg Phe Gln Ile Pro Glu Pro Lys Ser Ser Asp Lys Thr His Thr Cys
        115                 120                 125

Pro Pro Cys Pro Ala Pro Glu Ala Glu Gly Ala Pro Ser Val Phe Leu
    130                 135                 140

Phe Pro Pro Lys Pro Lys Asp Thr Leu Met Ile Ser Arg Thr Pro Glu
145                 150                 155                 160

Val Thr Cys Val Val Val Asp Val Ser His Glu Asp Pro Glu Val Lys
                165                 170                 175

Phe Asn Trp Tyr Val Asp Gly Val Glu Val His Asn Ala Lys Thr Lys
            180                 185                 190

Pro Arg Glu Glu Gln Tyr Asn Ser Thr Tyr Arg Val Val Ser Val Leu
        195                 200                 205

Thr Val Leu His Gln Asp Trp Leu Asn Gly Lys Glu Tyr Lys Cys Lys
    210                 215                 220

Val Ser Asn Lys Ala Leu Pro Ser Ser Ile Glu Lys Thr Ile Ser Lys
225                 230                 235                 240

Ala Lys Gly Gln Pro Arg Glu Pro Gln Val Tyr Thr Leu Pro Pro Ser
                245                 250                 255

Arg Asp Glu Leu Thr Lys Asn Gln Val Ser Leu Thr Cys Leu Val Lys
            260                 265                 270

Gly Phe Tyr Pro Ser Asp Ile Ala Val Glu Trp Glu Ser Asn Gly Gln
        275                 280                 285

Pro Glu Asn Asn Tyr Lys Thr Thr Pro Pro Val Leu Asp Ser Asp Gly
    290                 295                 300

Ser Phe Phe Leu Tyr Ser Lys Leu Thr Val Asp Lys Ser Arg Trp Gln
305                 310                 315                 320

Gln Gly Asn Val Phe Ser Cys Ser Val Met His Glu Ala Leu His Asn
                325                 330                 335

His Tyr Thr Gln Lys Ser Leu Ser Leu Ser Pro Gly Lys
            340                 345
```

-continued

```
<210> SEQ ID NO 81
<211> LENGTH: 173
<212> TYPE: PRT
<213> ORGANISM: Artificial
<220> FEATURE:
<223> OTHER INFORMATION: B7R1-VASP

<400> SEQUENCE: 81

Met Met Thr Gly Thr Ile Glu Thr Thr Gly Asn Ile Ser Ala Glu Lys
1               5                   10                  15

Gly Gly Ser Ile Ile Leu Gln Cys His Leu Ser Ser Thr Thr Ala Gln
            20                  25                  30

Val Thr Gln Val Asn Trp Glu Gln Gln Asp Gln Leu Leu Ala Ile Cys
        35                  40                  45

Asn Ala Asp Leu Gly Trp His Ile Ser Pro Ser Phe Lys Asp Arg Val
    50                  55                  60

Ala Pro Gly Pro Gly Leu Gly Leu Thr Leu Gln Ser Leu Thr Val Asn
65                  70                  75                  80

Asp Thr Gly Glu Tyr Phe Cys Ile Tyr His Thr Tyr Pro Asp Gly Thr
                85                  90                  95

Tyr Thr Gly Arg Ile Phe Leu Glu Val Leu Glu Ser Ser Val Ala Glu
            100                 105                 110

His Gly Ala Arg Phe Gln Ile Pro Arg Ser Gly Ser Gly Gly Ser Gly
        115                 120                 125

Gly Ser Asp Leu Gln Arg Val Lys Gln Glu Leu Leu Glu Glu Val Lys
    130                 135                 140

Lys Glu Leu Gln Lys Val Lys Glu Glu Ile Ile Glu Ala Phe Val Gln
145                 150                 155                 160

Glu Leu Arg Gly Ser Gly Gly His His His His His His
                165                 170
```